US009023793B2

(12) United States Patent
Leonard et al.

(10) Patent No.: US 9,023,793 B2
(45) Date of Patent: *May 5, 2015

(54) INTRANASAL CARBETOCIN FORMULATIONS AND METHODS FOR THE TREATMENT OF AUTISM

(75) Inventors: Alexis Kays Leonard, Maple Valley, WA (US); Joshua Orion Sestak, Lawrence, KS (US); Henry R. Costantino, Woodinville, WA (US); Anthony P. Sileno, Mendham, NJ (US); Lalit Raj Peddakota, San Diego, CA (US); Kayvon Emile Sharghi, Chevy Chase, MD (US); Garland M. Bellamy, Santa Fe, NM (US); Jason Philip Gesty, Seattle, WA (US); Steven C. Quay, Seattle, WA (US)

(73) Assignee: Retrophin, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/204,485

(22) Filed: Aug. 5, 2011
(Under 37 CFR 1.47)

(65) Prior Publication Data

US 2012/0172304 A1 Jul. 5, 2012

Related U.S. Application Data

(63) Continuation-in-part of application No. 12/599,267, filed as application No. PCT/US2007/079994 on Sep. 28, 2007, now abandoned, application No. 13/204,485, which is a continuation-in-part of application No. 11/537,468, filed on Sep. 29, 2006.

(60) Provisional application No. 60/942,607, filed on Jun. 7, 2007.

(51) Int. Cl.
A61K 38/11 (2006.01)
A61P 5/10 (2006.01)
A61K 9/00 (2006.01)
A61K 45/06 (2006.01)
A61K 31/337 (2006.01)
A61K 9/08 (2006.01)

(52) U.S. Cl.
CPC .............. *A61K 9/0043* (2013.01); *A61K 45/06* (2013.01); *A61K 31/337* (2013.01); *A61K 9/08* (2013.01)

(58) Field of Classification Search
None
See application file for complete search history.

(56) References Cited

U.S. PATENT DOCUMENTS

| 6,333,313 | B1  |   | 12/2001 | Copland, III et al. |
|-----------|-----|---|---------|---------------------|
| 6,894,026 | B1  | * | 5/2005  | Quay .......................... 514/11.6 |
| 2004/0037809 | A1 | * | 2/2004 | Quay et al. ................... 424/85.6 |

| 2004/0077540 | A1 | 4/2004  | Quay |
|--------------|----|---------|------|
| 2004/0235956 | A1 | 11/2004 | Quay |
| 2006/0062758 | A1 | 3/2006  | Cui et al. |
| 2007/0032410 | A1 | 2/2007  | Quay et al. |

FOREIGN PATENT DOCUMENTS

| EP | 0463653 A1 | 1/1992 |
| EP | 709099 A2 * | 5/1996 |
| WO | WO 9201440 A1 * | 2/1992 |
| WO | 9501185 A1 | 1/1995 |
| WO | WO 9856406 A1 * | 12/1998 |

OTHER PUBLICATIONS

Atke and Vilhardt, Uterotonic activity and myometrial receptor affinity of 1-deamino-1-carba-2-tyrosine(O-methyl)-oxytocin. Acta Endocrinol (Copenh). May 1987;115(1):155-160.

Boucher et al., Double-Blind, Randomized Comparison of the Effect of Carbetocin and Oxytocin on Intraoperative Blood Loss and Uterine Tone of Patients Undergoing Cesarean Section. J Perinatol. May-Jun. 1998;18(3):202-207.

Carvalho et al., Changes in the biogenic amine content of the prefrontal cortex, amygdala, dorsal hippocampus, and nucleus accumbens of rats submitted to single and repeated sessions of the elevated plus-maze test. Braz J Med Biol Res. Dec. 2005;38(12):1857-1866.

Holmes et al., Behavioral Characterization of Dopamine D5 Receptor Null Mutant Mice. Behav Neurosci. Oct. 2001;115(5):1129-1144.

Hunter et al., Effect of carbetocin, a long-acting oxytocin analog on the postpartum uterus. Clin Pharmacol Ther. Jul. 1992;52(1):60-67.

Insel et al., Oxytocin, vasopressin, and autism: is there a connection? Biol Psychiatry. Jan. 15, 1999;45(2):145-157.

Langen et al., Characterization in Rats of the Anxiolytic Potential of ELB139 [1-(4-Chlorophenyl)-4-piperidin-1-yl-1,5-dihydro-imidazol-2-on], a New Agonist at the Benzodiazepine Binding Site of the GABAA Receptor. J Pharmacol Exp Ther. Aug. 2005;314(2):717-724.

(Continued)

*Primary Examiner* — Wu-Cheng Winston Shen
*Assistant Examiner* — Jean Cornet
(74) *Attorney, Agent, or Firm* — Cooley LLP

(57) ABSTRACT

Methods and compositions containing oxytocin or an oxytocin analog, such as carbetocin, are provided for the prevention and treatment of autism spectrum disorders, related disorders and symptoms of such disorders. The methods and compositions of this disclosure are effective in the treatment of social withdrawal, eye contact avoidance, repetitive behaviors, anxiety, attention deficit, hyperactivity, depression, loss of speech, verbal communication difficulties, aversion to touch, visual difficulties, comprehension difficulties, and sound and light sensitivity. Additional compositions and methods are provided which employ oxytocin or an oxytocin analog in combination with a secondary or adjunctive therapeutic agent to yield more effective treatment tools against autism spectrum disorders and related disorders.

23 Claims, 4 Drawing Sheets

(56) References Cited

OTHER PUBLICATIONS

Leckman et al., Elevated Cerebrospinal Fluid Levels of Oxytocin in Obsessive-compulsive Disorder Comparison With Tourette's Syndrome and Healthy Controls. Arch Gen Psychiatry. Oct. 1994;51(10):782-792.

Leckman et al., The Role of Central Oxytocin in Obsessive Compulsive Disorder and Related Normal Behavior. Psychoneuroendocrinology. 1994;19(8):723-749.

Martin et al., Cerebrospinal Fluid Levels of Oxytocin in Prader-Willi Syndrome: A Preliminary Report. Biol Psychiatry. Dec. 15, 1998:44(12):1349-1352.

Modahl et al., Plasma oxytocin levels in autistic children. Biol Psychiatry. Feb. 15, 1998;43(4):270-277.

Norstrom et al., Contractile effect of oxytocin and 1-deamino-1-carba-2-tyrosine (0-methyl)-oxytocin in myometrial tissue from non-pregnant and term pregnant women. Acta Endocrinol (Copenh). May 1990:122(5):566-568.

Sahuque et al., Anxiogenic and aversive effects of corticotropin-releasing factor (CRF) in the bed nucleus of the stria terminalis in the rat: role of CRF receptor subtypes. Psychopharmacology (Berl). May 2006;186(1):122-132.

Silcox et al., Transfer of Carbetocin into Human Breast Milk. Obstet Gynecol. Sep. 1993;82(3):456-459.

Vilhardt, et al., Interaction of Chymotrypsin with Carbetocin ([1-deamino-1-monocarba-2-O-methyltyrosine]-oxytocin). Pharmacol Toxicol. Sep. 1997;81(3):147-150.

Office Action issued by SIPO in Application No. 200780053262.2 dated Jun. 10, 2011—English Translation only.

Lu, New dosage form for oral, nasal, pulmonary and rectal drug administration. Jul. 2005;2:647-655—includes English translation.

Final Office Action issued by SIPO in Application No. 200780053262.2 dated May 10, 2012—English Summary only.

Office Action issued in European Application No. 07843557.5 dated Jul. 25, 2013.

Jansen et al., Beta-cyclodextrins as vehicles in eye-drop formulations: an evaluation of their effects on rabbit corneal epithelium. Lens Eye Toxic Res. 1990;7(3-4):459-468 (abstract only).

CTD Inc. Webpage, Hydroxypropyl Beta Cyclodextrin. http://cyclodex.com/HydroxypropylBetaCyclodextrin.html. accessed Aug. 14, 2013.

Office Action issued by the United States Patent and Trademark Office in U.S. Appl. No. 11/537,468 dated Mar. 30, 2010.

Final Office Action issued by the United States Patent and Trademark Office in U.S. Appl. No. 11/537,468 dated Apr. 5, 2011.

Merkus et al., Classification of Cilia-Inhibiting Effects of Nasal Drugs. Larnyngoscope, 2001;111: 595-602.

Office Action issued by the United States Patent and Trademark Office in U.S. Appl. No. 12/599,267 dated Apr. 24, 2012.

Mayo Clinic Staff. "Autism: Prevention—MayoCiinic.com", http://www.mayoclinic.com/health/autism/DS00348/DSECTION=prevention, accessed Apr. 16, 2012.

WebMD. "What is Autism? Symptoms, Causes, Treatments and More", http://www.webmd.com/brain/autism/autism-topicoverview, accessed Apr. 16, 2012.

* cited by examiner

INTRANASAL CARBETOCIN FORMULATIONS AND METHODS FOR THE TREATMENT OF AUTISM

CROSS-REFERENCE TO RELATED APPLICATIONS

This application is a continuation-in-part and claims the benefit under 35 U.S.C. §120 of U.S. patent application Ser. No. 12/599,267, filed Jul. 7, 2010, now pending, which is a national stage entry of PCT/US2007/079994, filed Sep. 28, 2007, which claims the benefit of U.S. provisional patent application 60/942,607, filed Jun. 7, 2007. This application is also a continuation-in-part and claims the benefit under 35 U.S.C. §120 of U.S. patent application Ser. No. 11/537,468, filed Sep. 29, 2006, now pending. All above-cited applications are herein incorporated by reference in their entireties for all purposes.

TECHNICAL FIELD

The present disclosure relates to methods and compositions for the treatment of neurological and psychiatric disorders. In specific embodiments, this disclosure relates to the treatment of neurological and psychiatric disorders using carbetocin and related oxytocin analogs.

BACKGROUND

Autism spectrum disorders are a group of diseases characterized by varying degrees of impairment in communication skills, social interactions, and restricted, repetitive and stereotyped patterns of behavior. The difference in the diseases depends on the time of onset, the rate of symptom development, the severity of symptoms, and the exact nature of the symptoms. These disorders range from mild to severe impairment and include such diseases as autism, Asperger's syndrome, PDD-NOS, Rett's disorder, childhood disintegrative disorder, semantic communication disorder, non-verbal learning disabilities, high functioning autism, hyperlexia and some aspects of attention deficit hyperactivity disorder. While the exact number of children with autism spectrum disorders is unclear, rates in localized areas of the United States vary from 3.4 children per one thousand to 6.7 children per one thousand. Further, recent studies estimate that 15,000 children aged three through five years, and 78,000 children and young adults aged six through twenty-one years in the United States have autism. Rates in Europe and Asia are similar, with as many as six per one thousand children having at least one autism spectrum disorder. Additionally, there are a number of related disorders including anxiety disorders, obsessive-compulsive disorders, social deficit disorders, repetitive disorders and cognitive deficit disorders which exhibit symptoms similar to those displayed in autism spectrum disorders, greatly increasing the size of the affected population.

Characteristics of autism spectrum disorders include social withdrawal and averted gaze including an inability to make eye contact, repetitive behaviors and obsessions, stereotyped movements, anxiety, attention deficit, hyperactivity, depression, a reclusive personality, and the inability to understand feelings. Patients afflicted with autism spectrum disorders may have an aversion to physical affection or contact, ignore communication from others, or if socially engaged, demonstrate a marked inability to communicate or relate to others. Communication difficulties may manifest as a monotone voice, an inability to control the volume of their voice, echolalia or an inability to talk at all. Individuals with autism spectrum disorders may also suffer from visual difficulties, comprehension difficulties, sound and light sensitivity and mental retardation.

Children with autism spectrum disorders do not follow the typical patterns of child development. In some children, hints of future problems may be apparent from birth. In most cases, the problems in communication and social skills become more noticeable as the child lags further behind other children the same age. Some children initially develop normally and then begin to develop differences in the way they react to people and other unusual behaviors. Some parents report the change as being sudden, and that their children start to reject people, act strangely, and lose language and social skills they had previously acquired. In other cases, there is a plateau in development that becomes increasingly noticeable.

The underlying causes of autism spectrum and related disorders are unclear. Postmortem and MRI studies have implicated anomalies in many major brain structures including the cerebellum, cerebral cortex, limbic system, corpus callosum, basal ganglia, and brain stem. Other research is examining the role of neurotransmitters such as serotonin, dopamine, and epinephrine.

Currently, autism spectrum disorders are treated using applied behavior analysis or other behavior modification techniques; dietary modification such as a gluten or casein free diet, or large doses of vitamin B6 in combination with magnesium. Medications prescribed for autism address specific symptoms such as anxiety and depression and include agents such as fluoxetine, fluvoxamine, sertraline and clomipramine. Antipsychotic medications such as chlorpromazine, thioridazine, and haloperidol have been used to treat behavioral problems. Anticonvulsants such as arbamazepine, lamotrigine, topiramate, and valproic acid have been given to prevent seizures.

Results of a study (Hollander et al., American College of Neuropsychopharmacology Annual Meeting, December 2006) were reported to show that autistic adults who were given an intravenous doses of oxytocin had a statistically significant reduction in repetitive behaviors that are associated with autism.

Unfortunately, current treatments for autism spectrum and related disorders are mainly symptomatic and have proven unsuccessful in allowing such children and adults to become symptom, or disorder, free. There is therefore an unmet need in the art for alternative treatments for autism spectrum disorders and related pathologies.

SUMMARY OF THIS DISCLOSURE

It is an object of the present disclosure to provide methods and compositions for the treatment of neurological and psychiatric disorders.

It is an additional object of the present disclosure to provide methods and compositions for the treatment of autism spectrum disorders and disorders that include related symptoms such as developmental disorders, anxiety disorders, repetitive disorders, and cognitive deficit disorders.

It is another object of the present disclosure to provide novel formulations of oxytocin and related analogs including carbetocin for the treatment of autism spectrum disorders and related disorders.

It is a further object of the present disclosure to provide compositions and methods for treating and preventing symptoms of autism spectrum disorders and related disorders including, but not limited to, social withdrawal, eye contact avoidance, repetitive behaviors, anxiety, attention deficit, hyperactivity, depression, loss of speech, verbal communication difficulties, aversion to touch, visual difficulties, comprehension difficulties, and sound and light sensitivity. This disclosure achieves these objects and satisfies additional objects and advantages by providing novel and surprisingly effective methods and compositions for treating and/or preventing autism spectrum disorders, related disorders and symptoms of such disorders using oxytocin and oxytocin analogs.

Useful oxytocin and oxytocin analogs within the formulations and methods of this disclosure include, but are not limited to, 4-threonine-1-hydroxy-deaminooxytocin, 9-deamidooxytocin, an analog of oxytocin containing a glycine residue in place of the glycinamide residue; 7-D-proline-oxytocin and its deamino analog; (2,4-diisoleucine)-oxytocin, an analog of oxytocin with natriuretic and diuretic activities; deamino oxytocin analog; a long-acting oxytocin (OT) analog, 1-deamino-1-monocarba-E12-[Tyr(OMe)]-OT (dCOMOT); carbetocin, (1-butanoic acid-2-(O-methyl-L-tyrosine)-1-carbaoxytocin, or, alternatively, deamino-1 monocarba-(2-O-methyltyrosine)-oxytocin [d(COMOT)]); [Thr4-Gly7]-oxytocin (TG-OT); oxypressin; Ile-conopressin; atosiban; deamino-6-carba-oxytoxin (dC60), d[Lys(8)(5/6C-Fluorescein)]VT, d[Thr(4), Lys(8)(5/6C-Fluorescein)]VT, [HO(1)][Lys(8)(5/6C-Fluorescein)]VT, [HO(1)][Thr(4), Lys(8)(5/6C-Fluorescein)]VT, d[Om(8)(5/6C-Fluorescein)]VT, d[Thr(4), Om(8)(5/6C-Fluorescein)]VT, [HO(1)][Om(8)(5/6C-Fluorescein)]VT, [HO(1)][Thr(4), Om(8)(5/6C-Fluorescein)]VT, desmopressin, and 1-deamino-oxytocin in which the disulfide bridge between residues 1 and 6 is replaced by a thioether. Other useful forms of oxytocin or oxytocin analogs for use within this disclosure include other pharmaceutically acceptable active salts of said compounds, as well as active isomers, enantiomers, polymorphs, solvates, hydrates, and/or prodrugs of said compounds.

In exemplary embodiments, the compositions and methods of this disclosure employ oxytocin and/or an oxytocin analog to treat and/or prevent autism spectrum disorders, related disorders and symptoms of such disorders.

Mammalian subjects amenable for treatment using the compositions and methods of this disclosure include, but are not limited to, human and other mammalian subjects suffering from a psychiatric or neurological disorder including autism spectrum disorders such as autism, Asperger's syndrome, pervasive developmental disorder not otherwise specified, Rett's disorder, childhood disintegrative disorder, semantic pragmatic communication disorder, non-verbal learning disabilities, high functioning autism, hyperlexia, and attention deficit hyperactivity disorder (ADHD). Mammalian subjects amenable for treatment using the compositions and method of this disclosure additionally include, but are not limited to, human and other mammalian subjects suffering from related disorders including Landau-Kleffner Syndrome; multi-systems disorder; anxiety disorders including, but not limited to, social phobia, generalized anxiety disorder, panic disorder, posttraumatic stress disorder, phobia, agoraphobia, obsessive-compulsive disorders; social deficit disorders including, but not limited to, paranoid personality disorder, schizotypal personality disorder, schizoid personality disorder, avoidant personality disorder, conduct disorder, borderline personality disorder, histrionic personality disorder; repetitive disorders including, but not limited to, impulse control and addiction disorders, and eating disorders such as bulimia, anorexia nervosa, binge eating disorder; cognitive deficit disorders including, but not limited to, dementia, Alzheimer's, Creutzfeld-Jakob disease, attention deficit disorder, attention deficit hyperactivity disorder, mild cognitive decline, and cognitive disorder not otherwise specified.

These and other subjects are effectively treated, prophylactically and/or therapeutically, by administering to the subject an effective amount of an oxytocin or oxytocin analog compound sufficient to prevent or reduce the occurrence or symptoms of autism spectrum disorders and related disorders. Therapeutically useful methods and formulations of this disclosure will effectively use oxytocin and oxytocin analogs in a variety of forms, as noted above, including any active, pharmaceutically acceptable salt of said compounds, as well as active isomers, enantiomers, polymorphs, solvates, hydrates, prodrugs and/or combinations thereof. Carbetocin is employed as an illustrative embodiment of this disclosure within the examples herein below.

Within additional aspects of this disclosure, combinatorial formulations and methods are provided comprising an effective amount of oxytocin or an oxytocin analog including carbetocin in combination with one or more secondary adjunctive agent(s) that is/are combinatorially formulated or coordinately administered with the oxytocin or oxytocin analog to yield an effective response in an individual suffering from autism spectrum disorders and related disorders. Exemplary combinatorial formulations and coordinate treatment methods in this context employ the oxytocin or oxytocin analog in combination with one or more additional, secondary or adjunctive therapeutic agents. The secondary or adjunctive therapeutic agents used in combination with, for example, carbetocin, in these embodiments may possess direct or indirect anxiolytic activity alone or in combination with, for example, carbetocin. The secondary or adjunctive therapeutic agents used in combination with, for example, carbetocin, in these embodiments may possess direct or indirect antipsychotic activity alone or in combination with, for example, carbetocin. The secondary or adjunctive therapeutic agents used in combination with, for example, carbetocin, in these embodiments may possess direct or indirect anti-convulsant activity alone or in combination with, for example, carbetocin. The secondary or adjunctive therapeutic agents used in combination with, for example, carbetocin, in these embodiments may possess direct or indirect anti-viral activity alone or in combination with, for example, carbetocin. Useful adjunctive therapeutic agents in these combinatorial formulations and coordinate treatment methods include, for example, serotonin reuptake inhibitors, selective serotonin reuptake inhibitors including, but not limited to, fluoxetine, fluvoxamine, sertraline, clomipramin; antipsychotic medications including, but not limited to, haloperidol, thioridazine, fluphenazine, chlorpromazine, risperidone, olanzapine, ziprasidone; anti-convulsants, including, but not limited to, carbamazepine, lamotrigine, topiramate, valproic acid, stimulant medications including, but not limited to, methylphenidate, α2-adrenergic agonists, amantadine, and clonidine; antidepressants including, but not limited to, naltrexone, lithium, and benzodiazepines; anti-virals, including, but not limited to, valtrex; secretin; axiolytics including, but not limited to, buspirone; immunotherapy. Additional adjunctive therapeutic agents include vitamins including, but not limited to, B-vitamins (B6, B12, thiamin), vitamin A, and essential fatty acids. Adjunctive therapies may also include behavioral modification and changes in diet such as a gluten-casein free diet.

The present disclosure provides pharmaceutical formulations. In some embodiments, the pharmaceutical formulations are formulated for intranasal administration. In some embodiments, the pharmaceutical formulations comprise carbetocin. In some embodiments, the pharmaceutical formulations are for intranasal delivery of carbetocin. In some embodiments, the pharmaceutical formulations comprise carbetocin and/or analog thereof and at least one solubilizer. In some embodiments, the pharmaceutical formulations further comprise at least one chelator.

In some embodiments, the solubilizer is methyl-β-cyclodextrin or didecanoyl-L-α-phosphatidylcholine (DDPC). In some embodiments, the formulations have a pH from about 4 to about 6.

In some embodiments, the chelator is methyl-β-cyclodextrin (Me-β-CD), edetate disodium (EDTA), arginine, sorbitol, NaCl, methylparaben sodium (MP), propylparaben sodium (PP), chlorobutanol (CB), benzyl alcohol, zinc chloride, ethyl alcohol, didecanoyl L-α-phosphatidylcholine (DDPC), polysorbate, lactose, citrate, tartrate, acetate, or phosphate. In some embodiments, the chelator is ethylene diamine tetra acetate (EDTA).

In some embodiments, the pharmaceutical formulations further comprise at least one tonicifier. In some embodiments, the tonicifier is a salt. In some embodiments, the tonicifier is a sodium salt. For example, the tonicifier is sodium chloride.

In some embodiments, the pharmaceutical formulations further comprise at least one stabilizing agent (stabilizer). In some embodiments, the stabilizing agent is an amino acid or a salt thereof. In some embodiments, the stabilizing agent is an amino acid with positively charged side chain(s) or a salt thereof. In some embodiments, the stabilizing agent is arginine or a salt thereof.

In some embodiments, the pharmaceutical formulations further comprise at least one preservative. In some embodiments, the preservative is selected from the group consisting of benzalkonium chloride, chlorobutanol, methyl paraben, propyl paraben, and a combination thereof.

In some embodiments, the pharmaceutical formulations further comprise a buffer. In some embodiments, the buffer is selected from the group consisting of arginine, citrate, tartrate, acetate, phosphate, and a combination thereof.

In some embodiments, the pharmaceutical formulations further comprise at least one alkalizing agent and/or an acidifying agent. In some embodiments, the alkalizing agent is sodium hydroxide and the acidifying agent is hydrochloric acid.

In some embodiments, the pharmaceutical formulations further comprise at least one solvent. In some embodiments, the formulations comprise water as solvent.

In some embodiments, the pharmaceutical formulations have an osmolality from about 200 to about 250 mOsm/kgH$_2$O.

In some embodiments, the pharmaceutical formulations comprise carbetocin, methyl-β-cyclodextrin, EDTA, sodium chloride, arginine hydrochloride, chlorobutanol, a acetate buffer, sodium hydroxide, and hydrochloride acid; wherein the formulation has a pH from about 4 to about 6.

In some embodiments, the pharmaceutical formulations further comprise one or more adjunctive therapeutic agent. In some embodiments, the adjunctive therapeutic agent is selected from a serotonin reuptake inhibitor, a selective serotonin reuptake inhibitor, an antipsychotic medication, an anti-convulsant, a stimulant medication, an anti-viral medication, an axiolytic medication, a vitamin, an immunotherapeutic agent, and a combination thereof.

The present disclosure also provides methods for treating an autism or a symptom thereof in a subject in need thereof. In some embodiments, the subject is a mammalian subject, for example, a human. In some embodiments, the methods comprise administering a therapeutically effective amount of the pharmaceutical formulations described in the present disclosure. In some embodiments, the methods further comprise therapy of behavioral modification or diet modification.

In some embodiments, said symptom is selected from social withdrawal, eye contact avoidance, repetitive behaviors, anxiety, attention deficit, hyperactivity, depression, loss of speech, verbal communication difficulty, aversion to touch, visual difficulty, comprehension difficulty, sound sensitivity, light sensitivity, and a combination thereof.

The present disclosure also provides methods for treating an autism or a symptom thereof in a subject in need thereof. In some embodiments, the subject is a mammalian subject, for example, a human. In some embodiments, the methods comprise co-administering a therapeutically effective amount of the pharmaceutical formulation described in the present disclosure and one or more adjunctive therapeutic agent to the subject. In some embodiments, the methods further comprise therapy of behavioral modification or diet modification.

In some embodiments, said adjunctive therapeutic agent is selected from a group consisting of a serotonin reuptake inhibitor, a selective serotonin reuptake inhibitor, an antipsychotic medication, an anti-convulsant, a stimulant medication, an anti-viral medication, an axiolytic medication, a vitamin, an immunotherapeutic agent, and a combination thereof.

The forgoing objects and additional objects, features, aspects and advantages of the instant disclosure will become apparent from the following detailed description.

DETAILED DESCRIPTION OF THIS DISCLOSURE

Figure 1:
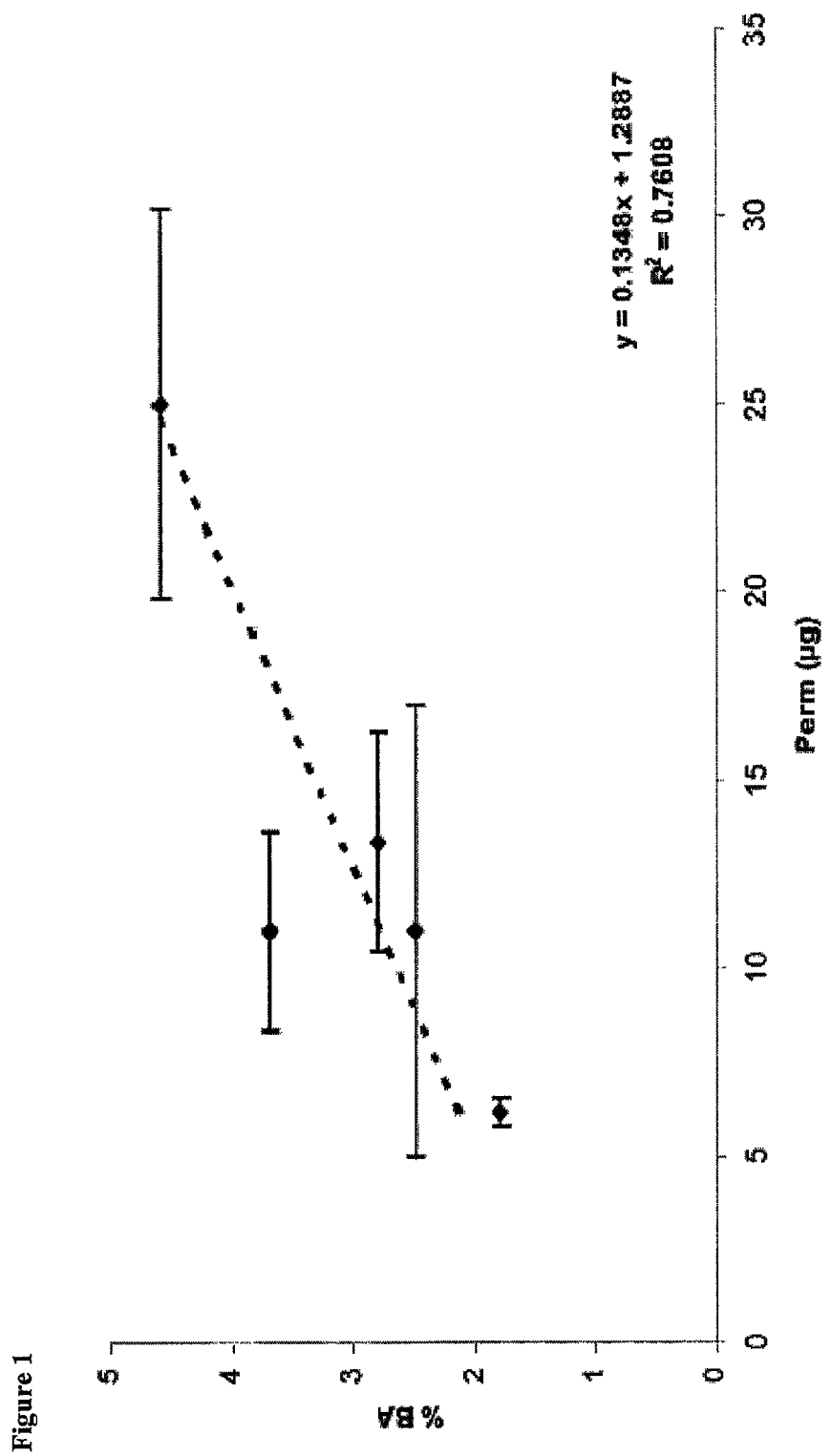
FIG. 1: Graph showing in vitro-in vivo correlation for pharmacokinetic study 1.

The instant disclosure provides novel methods and compositions for preventing and/or treating psychiatric and neurological disorders including autism spectrum disorders, related disorders and symptoms of such disorders in mammalian subjects. In various embodiments, the present disclosure uses oxytocin and oxytocin analogs including carbetocin to treat such psychiatric and neurological disorder.

As used herein, the term "analog" or "agonist" refers to any molecule that demonstrates activity similar to that of the parent molecule. Such a molecule may be a synthetic analog, fragment, pharmaceutically acceptable salt, or endogenous biological molecule capable of similar activity to the parent compound.

As used herein, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, "about" or "consisting essentially of" mean±20% of the indicated range, value, or structure, unless otherwise indicated. As used herein, the terms "include" and "comprise" are used synonymously. It should be understood that the terms "a" and "an" as used herein refer to "one or more" of the enumerated components. The use of the alternative (e.g., "or") should be understood to mean either one, both or any combination thereof of the alternatives.

The term "autism" is used interchangeably with "autism spectrum", "autism spectrum disorder", "autism spectrum conditions", and "pervasive developmental disorder".

As used herein, the term "treating" refers to preventing, ameliorating, relieving, improving, or curing the conditions, symptoms, or implications caused by or associated with autism.

The term "co-administration" or "coadministration" refers to administration of the present pharmaceutical formulation and the one or more adjunctive therapeutic agent together in a coordinated fashion. For example, the co-administration can be simultaneous administration, sequential administration, overlapping administration, interval administration, continuous administration, or a combination thereof. That is, the present pharmaceutical formulation and the one or more adjunctive therapeutic agent can be administered simultaneously, sequentially, or separately.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

Formulations for use in treating and preventing autism spectrum disorders, related disorders and symptoms of such disorders employ oxytocin or an oxytocin analog such as carbetocin, including all active pharmaceutically acceptable compounds of this description as well as various foreseen and readily provided complexes, derivatives, salts, solvates, isomers, enantiomers, polymorphs, and prodrugs of these compounds, and combinations thereof. Exemplary analogs for use within this disclosure include, as illustrative embodiments, 4-threonine-1-hydroxy-deaminooxytocin, 9-deamidooxytocin, an analog of oxytocin containing a glycine residue in place of the glycinamide residue; 7-D-proline-oxytocin and its deamino analog; (2,4-diisoleucine)-oxytocin, an analog of oxytocin with natriuretic and diuretic activities; deamino oxytocin analog; a long-acting oxytocin (OT) analog, 1-deamino-1-monocarba-E12-[Tyr(OMe)]-OT (dCOMOT); carbetocin, (1-butanoic acid-2-(O-methyl-L-tyrosine)-1-carbaoxytocin, or, alternatively, deamino-1 monocarba-(2-O-methyltyrosine)-oxytocin [d(COMOT)]); [Thr4-Gly7]-oxytocin (TG-OT); oxypressin; Ile-conopressin; atosiban; deamino-6-carba-oxytoxin (dC60), d[Lys(8)(5/6C-Fluorescein)]VT, d[Thr(4), Lys(8)(5/6C-Fluorescein)]VT, [HO(1)][Lys(8)(5/6C-Fluorescein)]VT, [HO(1)][Thr(4), Lys(8)(5/6CFluorescein)]VT, d[Om(8)(5/6C-Fluorescein)]VT, d[Thr(4), Om(8)(5/6C-Fluorescein)]VT, [HO(1)][Om(8)(5/6C-Fluorescein)]VT, [HO(1)][Thr(4), Om(8)(5/6C-Fluorescein)]VT, desmopressin, and 1-deamino-oxytocin in which the disulfide bridge between residues 1 and 6 is replaced by a thioether.

Within the formulations and methods, oxytocin or an oxytocin analog as disclosed herein is effectively used to treat autism spectrum disorders, related disorders and symptoms of such disorders in mammalian subjects suffering from autism spectrum disorders and/or related disorders and symptoms of such disorders including social withdrawal, eye contact avoidance, repetitive behaviors, anxiety, attention deficit, hyperactivity, depression, loss of speech, verbal communication difficulties, aversion to touch, visual difficulties, comprehension difficulties, and sound and light sensitivity.

A broad range of mammalian subjects, including human subjects, are amenable for treatment using the formulations and methods of this disclosure. These subjects include, but are not limited to, human and other mammalian subjects suffering from a psychiatric or neurological disorder including autism spectrum disorders such as autism, Asperger's syndrome, pervasive developmental disorder not otherwise specified, Rett's disorder, childhood disintegrative disorder, semantic pragmatic communication disorder, non-verbal learning disabilities, high functioning autism, hyperlexia, and ADHD. Mammalian subjects amenable for treatment using the compositions and methods of this disclosure additionally include, but are not limited to, human and other mammalian subjects suffering from related disorders including Landau-Kleffner Syndrome; multi-systems disorder; anxiety disorders including, but not limited to, social phobia, generalized anxiety disorder, panic disorder, posttraumatic stress disorder, phobia, agoraphobia, obsessive-compulsive disorders; social deficit disorders including, but not limited to, paranoid personality disorder, schizotypal personality disorder, schizoid personality disorder, avoidant personality disorder, conduct disorder, borderline personality disorder, histrionic personality disorder; repetitive disorders including, but not limited to, impulse control and addiction disorders, and eating disorders such as bulimia, anorexia nervosa, binge eating disorder; cognitive deficit disorders including, but not limited to, dementia, Alzheimer's, Creutzfeld-Jakob disease, attention deficit disorder, attention deficit hyperactivity disorder, mild cognitive decline, and cognitive disorder not otherwise specified.

Within the methods and compositions of this disclosure, one or more oxytocin analogs as disclosed herein is/are effectively formulated or administered as a psychiatric or neurologic treating agent effective for treating autism spectrum disorders, related disorders and symptoms of such disorders. In exemplary embodiments, carbetocin is used for illustrative purposes alone or in combination with one or more adjunctive therapeutic agent(s). The present disclosure further provides additional, pharmaceutically acceptable oxytocin analogs in the form of a native or synthetic compound, including complexes, derivatives, salts, solvates, isomers, enantiomers, polymorphs, and prodrugs of the compounds disclosed herein, and combinations thereof, which are effective as autism spectrum disorders and related disorder treating agents within the methods and compositions of this disclosure.

Autism spectrum disorders are defined by specific behaviors that can range from mild to severe. Symptoms include deficits in social interaction, verbal and nonverbal communication and repetitive behaviors and interests. The development of impairments in autistic persons is varied and characteristically uneven, resulting in good skills in some areas and poor skills in others. Echolalia is a common feature of language impairment that, when present, may cause language skills to appear better than they really are. There may also be deficiencies in symbolic thinking, stereotypic behaviors (e.g., repetitive nonproductive movements of hands and fingers, rocking, meaningless vocalizations), self-stimulation, self-injury behaviors, and seizures. No single cause has been identified for the development of autism though genetic origins are suggested by studies of twins and a higher incidence of recurrence among siblings. In addition, an increased frequency of autism is found in individuals with genetic conditions such as fragile X syndrome and tuberous sclerosis.

Possible contributing factors in the development of autism include infections, errors in metabolism, immunology, lead poisoning, and fetal alcohol syndrome. The compositions and methods of the present disclosure are effective in the treatment of all types of autism spectrum disorders, regardless of cause.

Oxytocin is a mammalian hormone secreted by the pituitary gland that acts as a neurotransmitter and is known to stimulate uterine contractions and milk let down. It is a nine amino acid peptide with the sequence Cys-Tyr-Ile-Gln-Asn-Cys-Pro-Leu-Gly (SEQ ID NO: 1). Based on a review of evidence from animal studies demonstrating that the nonapeptides, oxytocin and vasopressin (Cys-Tyr-Phe-Gln-Asn-Cys-Pro-Arg-Gly (SEQ ID NO: 2)), have unique effects on the normal expression of species-typical social behavior, communication and rituals, it was proposed that oxytocin or vasopressin neurotransmission may account for several features associated with autism. (Insel, et al., *Biol. Psychiatry* 45:145-157, 1999). A study on autistic children reported that such children had significantly lower levels of plasma oxytocin than normal children. Elevated oxytocin levels were associated with higher scores on social and developmental tests in non-autistic children, but associated with lower scores in autistic children, suggesting that altered oxytocin levels may be associated with autism in children (Modahl, et al., *Biol. Psychiatric* 43:270-277, 1998). Elevated levels of oxytocin have additionally been implicated in certain obsessive-compulsive behaviors such as excessive worrying, sexual compulsions and/or compulsive washing and cleaning. (Leckman, et al., *Psychoneuroendocrinology* 19:723-749, 1994; Leckman, et al., *Arch Gen Psychiatry* 51:782-92, 1994). Elevated levels of oxytocin have also been implicated in Prader-Willi syndrome, a genetic disorder associated with mental retardation, appetite dysregulation and a risk of developing obsessive compulsive disorder (Martin, et al., *Biol. Psychiatric* 44:1349-1352, 1998).

A number of oxytocin analogs have been evaluated as possible substitute agents for inducing uterine contraction and milk let-down in mammalian patients with the goal of minimizing oxytocin's side effects. One such analog, carbetocin (1-butanoic acid-2-(O-methyl-L-tyrosine)-1-carbaoxytocin, or, alternatively, deamino-1 monocarba-(2-O-methyl-tyrosine)-oxytocin [d(COMOT)]) is a long-acting synthetic oxytocin analog which exhibits both uterotonic and milk let-down inducing activities (Atke, et al., *Acta Endocrinol.* 115:155-160, 1987; Norstrom, et al., *Acta Endocrinol.* 122:566-568, 1990; Hunter, et al., *Clin. Pharmacol. Ther.* 52:60-67, 1992; Silcox, et al., *Obstet. Gynecol.* 82:456-459, 1993; Vilhardt, et al., *Pharmacol. Toxicol.* 81:147-150, 1997; Boucher, et al., *J. Perinatology* 18:202-207, 1998). Whereas the 9 amino acid oxytocin contains a disulfide bond between the cysteines in the first and sixth positions, carbetocin's ring structure is derived from a C—S bond between a butyric acid at the N-terminus and the cysteine in the fifth position, Butyryl-Tyr(Me)-Ile-Gln-Asn-Cys-Pro-Leu-Gly-NH$_2$ (SEQ ID NO: 3). The structure of carbetocin is shown below.

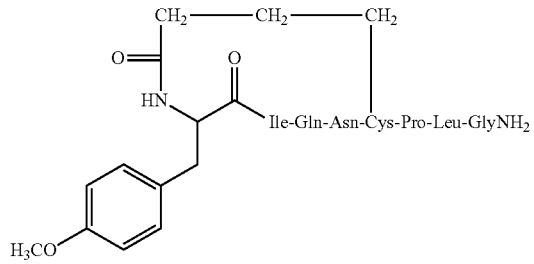

The half-life of carbetocin is reportedly 4 to 10 times longer than that of oxytocin, which is reflected in substantial prolongation of the uterotonic and milk let-down inducing activities of this analog. This apparent increase in metabolic stability is attributed to N-terminal desamination and replacement of a 1-6 disulfide bridge by a methylene group in carbetocin, which modifications are thought to protect this analog from aminopeptidase and disulfidase cleavage (Hunter, et al., *Clin. Pharmacol. Ther.* 52:60-67, 1992). It is thought with its increased half-life, carbetocin may be a potential therapeutic treatment for social disorders such as anxiety disorder and autism spectrum disorder. The methods and compositions of the present disclosure comprise the use of oxytocin and oxytocin analogs in novel formulations for the treatment of neurological and psychiatric disorders including autism spectrum disorders and related disorders such as obsessive compulsive disorders.

The compositions and methods of the instant disclosure represented by carbetocin are effective for treating or preventing psychiatric and neurological disorders in mammals. In particular, the compositions and methods of this disclosure can be administered to mammalian subjects to measurably alleviate or prevent one or more symptoms of an autism spectrum disorder or a related condition, selected from symptoms including, but not limited to, social withdrawal, eye contact avoidance, repetitive behaviors, anxiety, attention deficit, hyperactivity, depression, loss of speech, verbal communication difficulties, aversion to touch, visual difficulties, comprehension difficulties, and sound and light sensitivity.

Compositions comprising carbetocin or other oxytocin analogs for the treatment of autism spectrum disorders, related disorders and symptoms of such disorders, comprise an amount of carbetocin or other oxytocin analog which is effective for prophylaxis and/or treatment of autism spectrum disorders, related disorders and symptoms of such disorders in a mammalian subject. Typically an effective amount of the carbetocin or other oxytocin analog will comprise an amount of the active compound which is therapeutically effective, in a single or multiple dosage form, over a specified period of therapeutic intervention, to measurably alleviate one or more symptoms of autism spectrum disorders and/or related disorders in the subject. Within exemplary embodiments, these compositions are effective within in vivo treatment methods to alleviate autism spectrum disorders and related disorders.

Autism spectrum and related disorder treating compositions of this disclosure typically comprise an effective amount or unit dosage of oxytocin or an oxytocin analog which may be formulated with one or more pharmaceutically acceptable carriers, excipients, vehicles, emulsifiers, stabilizers, preservatives, buffers, and/or other additives that may enhance stability, delivery, absorption, half-life, efficacy, pharmacokinetics, and/or pharmacodynamics, reduce adverse side effects, or provide other advantages for pharmaceutical use. Exemplary excipients include solubilizers, surfactants and chelators, for example formulations may include, methyl-β-cyclodextrin (Me-β-CD) as a solubilizing agent, edetate disodium (EDTA) as a chelating agent, arginine, sorbitol, NaCl, methylparaben sodium (MP), propylparaben sodium (PP), chlorobutanol (CB), benzyl alcohol, zinc chloride, ethyl alcohol, didecanoyl L-α-phosphatidylcholine (DDPC), polysorbate, lactose, citrate, tartrate, acetate, and or phosphate. Effective amounts of oxytocin or an oxytocin analog such as carbetocin for the treatment of neurological and psychiatric disorders (e.g., a unit dose comprising an effective concentration/amount of carbetocin, or of a selected pharmaceutically acceptable salt, isomer, enantiomer, solvate, polymorph and/or prodrug of carbetocin) will be readily determined by those of ordinary skill in the art, depending on clinical and patient-specific factors. Suitable effective unit dosage amounts of the active compounds for administration to mammalian subjects, including humans, may range from 10 to 1500 µg, 20 to 1000 µg, 25 to 750 µg, 50 to 500 µg, or 150 to 500 µg, 10 to 1500 mg, 20 to 1000 mg, 25 to 750 mg, 50 to 500 mg, or 150 to 500 mg. In certain embodiments, the effective dosage of oxytocin or an oxytocin analog may be selected within narrower ranges of, for example, 10 to 25 µg, 30-50 µg, 75 to 100 µg, 100 to 250 µg, or 250 to 500 µg, 10 to 25 mg, 30-50 mg, 75 to 100 mg, 100 to 250 mg, or 250 to 500 mg. These and other effective unit dosage amounts may be administered in a single dose, or in the form of multiple daily, weekly or monthly doses, for example in a dosing regimen comprising from 1 to 5, or 2-3, doses administered per day, per week, or per month. In one exemplary embodiment, dosages of 10 to 25 mg, 30-50 mg, 75 to 100 mg, 100 to 250 mg, or 250 to 500 mg, are administered one, two, three, four, or five times per day. In more detailed embodiments, dosages of 50-75 mg, 100-200 mg, 250-400 mg, or 400-600 mg are administered once or twice daily. In alternate embodiments, dosages are calculated based on body weight, and may be administered, for example, in amounts from about 0.5 mg/kg to about 100 mg/kg per day, 1 mg/kg to about 75 mg/kg per day, 1 mg/kg to about 50 mg/kg per day, 2 mg/kg to about 50 mg/kg per day, 2 mg/kg to about 30 mg/kg per day or 3 mg/kg to about 30 mg/kg per day.

The amount, timing and mode of delivery of compositions of this disclosure comprising an effective amount of carbetocin or other oxytocin analog will routinely be adjusted on an individual basis, depending on such factors as weight, age, gender, and condition of the individual, the acuteness of the autism spectrum disorders, related disorders and/or symptoms of such disorders, whether the administration is prophylactic or therapeutic, and on the basis of other factors known to effect drug delivery, absorption, pharmacokinetics, including half-life, and efficacy.

An effective dose or multi-dose treatment regimen for the instant formulations will ordinarily be selected to approximate a minimal dosing regimen that is necessary and sufficient to substantially prevent or alleviate autism spectrum disorders, related disorders and/or symptoms of such disorders in the subject. A dosage and administration protocol will often include repeated dosing therapy over a course of several days or even one or more weeks or years. An effective treatment regime may also involve prophylactic dosage administered on a day or multi-dose per day basis lasting over the course of days, weeks, months or even years.

Various assays and model systems can be readily employed to determine the therapeutic effectiveness of oxytocin or an oxytocin analog in the treatment of autism spectrum disorders and related disorders. The effectiveness of the compositions for these and related conditions can be routinely demonstrated according to a variety of methods, including, for example, by measuring markers such as those measured in the Checklist of Autism in Toddlers (CHAT), the modified Checklist for Autism in Toddlers (M-CHAT), the Screening Tool for Autism in Two-Year-Olds (STAT), the Social Communication Questionnaire (SCQ), the Autism Spectrum Screening Questionnaire (ASSQ), the Australian Scale for Asperger's Syndrome, the Childhood Asperger Syndrome Test (CAST), the Autism Diagnosis Interview-Revised (ADI-R), the Autism Diagnostic Observation Schedule (ADOS-G), the Childhood Autism Rating Scale (CARS), audiologic hearing evaluation, Administered PTSD Scale, the Eysenck Personality Inventory, the Hamilton Anxiety Scale, or in various animal models such as the well-known Vogel (thirsty rat conflict) test, or the elevated plus maze test. Effective amounts of a compound of oxytocin or an oxytocin analog will measurably prevent, decrease the severity of, or delay the onset or duration of, one or more of the foregoing autism spectrum disorders, related disorders of symptoms of such disorders in a mammalian subject.

Administration of an effective amount of oxytocin or an oxytocin analog such as carbetocin to a subject presenting with one or more of the foregoing symptom(s) will detectably decrease, eliminate, or prevent the subject symptom(s). In exemplary embodiments, administration of a compound of carbetocin to a suitable test subject will yield a reduction in one or more target symptom(s) associated with a neurological or psychiatric disorder by at least 10%, 20%, 30%, 50% or greater, up to a 75-90%, or 95% or greater, reduction in the one or more target symptom(s) or disorders, compared to placebo-treated or other suitable control subjects. Comparable levels of efficacy are contemplated for the entire range of neurological and psychiatric disorders identified herein for treatment or prevention using the compositions and methods of this disclosure. Within additional aspects of this disclosure, combinatorial formulations and coordinate administration methods are provided which employ an effective amount of oxytocin or an oxytocin analog such as carbetocin and one or more secondary or adjunctive agent(s) that is/are combinatorially formulated or coordinately administered with the oxytocin or oxytocin analog to yield a combined, multi-active agent or coordinate treatment method. Exemplary combinatorial formulations and coordinate treatment methods in this context employ the oxytocin or oxytocin analog in combination with one or more secondary psychiatric or neurological agent(s) or with one or more adjunctive therapeutic agent(s) that is/are useful for treatment or prophylaxis of the targeted disease, condition and/or symptom(s) in the selected combinatorial formulation or coordinate treatment regimen. For most combinatorial formulations and coordinate treatment methods of this disclosure, oxytocin or a related analog is formulated, or coordinately administered, in combination with one or more secondary or adjunctive therapeutic agent(s) to yield a combined formulation or coordinate treatment method that is combinatorially effective or coordinately useful to treat autism spectrum disorders or related disorders and/or one or more symptom(s) of such disorders. Exemplary combinatorial formulations and coordinate treatment methods in this context employ oxytocin or an oxytocin analog in combination with one or more secondary or adjunctive therapeutic agents selected from, for example, serotonin reuptake inhibitors, selective serotonin reuptake inhibitors including, but not limited to, fluoxetine, fluvoxamine, sertraline, clomipramin; antipsychotic medications including, but not limited to, haloperidol, thioridazine, fluphenazine, chlorpromazine, risperidone, olanzapine, and ziprasidone; anti-convulsants, including, but not limited to, carbamazepine, lamotrigine, topiramate, and valproic acid, stimulant medications including, but not limited to, methylphenidate, α2-adrenergic agonists, amantadine, and clonidine; antidepressants including, but not limited to monoamine oxidase inhibitors, including phenelzine and isocarboxazide, tricyclic antidepressants, including amitriptaline, clomipramine, desipramine, and nortriptyline, atypical antidepressants (non-SSRIs), including Bupropion (Wellbutrin), Velafaxine (Effexor), and SSRIs such as Citalopram, Fluoxetine, Fluvoxamine, Paroxetine, and Sertraline; axiolytics including, but not limited to benzodiazepine and buspirone. Additional adjunctive therapeutic agents include vitamins including but not limited to, B-vitamins (B6, B12, thiamin), vitamin A, and essential fatty acids.

Adjunctive therapies may include behavioral modification and changes in diet such as a gluten-casein free diet.

Within additional aspects of this disclosure, combinatorial formulations and coordinate administration methods are provided which employ an effective amount of one or more compounds of oxytocin or an oxytocin analog, and one or more additional active agent(s) that is/are combinatorially formulated or coordinately administered with the oxytocin or oxytocin analog yielding an effective formulation or method to treat autism spectrum disorders, related disorders and symptoms of such disorders, and/or to alleviate or prevent one or more symptom(s) of a neurological or psychiatric disorder in a mammalian subject. Exemplary combinatorial formulations and coordinate treatment methods in this context employ oxytocin or an oxytocin analog in combination with one or more additional or adjunctive anxiolytic, antidepressant, anticonvulsant, nootropic, antipsychotic, stimulant, anti-viral, immunotherapeutic, anesthetic, hypnotic or muscle relaxant agent(s). In additional combinatorial formulations and coordinate treatment methods, oxytocin or an oxytocin analog is formulated or co-administered in combination with one or more secondary therapeutic agents used to treat symptoms which may accompany the psychiatric or neurological conditions listed above.

To practice the coordinate administration methods of this disclosure, oxytocin or an oxytocin analog is administered, simultaneously or sequentially, in a coordinate treatment protocol with one or more of the secondary or adjunctive therapeutic agents contemplated herein. The coordinate administration may be done simultaneously or sequentially in either order, and there may be a time period while only one or both (or all) active therapeutic agents, individually and/or collectively, exert their biological activities. A distinguishing aspect of all such coordinate treatment methods is that the oxytocin or oxytocin analog such as carbetocin exerts at least some detectable therapeutic activity, and/or elicits a favorable clinical response, which may or may not be in conjunction with a secondary clinical response provided by the secondary therapeutic agent. Often, the coordinate administration of oxytocin or an oxytocin analog such as carbetocin with a secondary therapeutic agent as contemplated herein will yield an enhanced therapeutic response beyond the therapeutic response elicited by either or both the oxytocin analog and/or secondary therapeutic agent alone.

Within exemplary embodiments, oxytocin, or an oxytocin analog will be coordinately administered (simultaneously or sequentially, in combined or separate formulation(s)), with one or more secondary agents or other indicated therapeutic agents, for example, selected from, for example, serotonin reuptake inhibitors, selective serotonin reuptake inhibitors including, but not limited to, fluoxetine, fluvoxamine, sertraline, clomipramin; .antipsychotic medications including, but not limited to, haloperidol, thioridazine, fluphenazine, chlorpromazine, risperidone, olanzapine, ziprasidone; anti-convulsants, including, but not limited to, carbamazepine, lamotrigine, topiramate, valproic acid, stimulant medications including, but not limited to, methylphenidate, α2-adrenergic agonists, amantadine, and clonidine; antidepressants including, but not limited to, naltrexone, lithium, and benzodiazepines; anti-virals, including, but not limited to valtrex; secretin; axiolytics including, but not limited to buspirone; immunotherapy. Additional adjunctive therapeutic agents include vitamins including but not limited to, B-vitamins (B6, B12, thiamin), vitamin A, and essential fatty acids. Adjunctive therapies may include behavioral modification and changes in diet such as a gluten-casein free diet.

In certain embodiments, this disclosure provides combinatorial neurological and psychiatric treating formulations comprising oxytocin and one or more adjunctive agent(s) having effective activity for the treatment of autism spectrum disorders and related disorders. Within such combinatorial formulations, oxytocin and oxytocin analogs and the adjunctive agent(s) will be present in a combined formulation in effective amounts, alone or in combination. In exemplary embodiments, oxytocin or an oxytocin analog such as carbetocin will be present in an effective amount. Alternatively, the combinatorial formulation may comprise one or both of the active agents in sub-therapeutic singular dosage amount(s), wherein the combinatorial formulation comprising both agents features a combined dosage of both agents that is collectively effective in eliciting a desired response. Thus, one or both of the oxytocin or oxytocin analog and additional agents may be present in the formulation, or administered in a coordinate administration protocol, at a sub-therapeutic dose, but collectively in the formulation or method they elicit a detectable response in the subject.

As noted above, in all of the various embodiments of this disclosure contemplated herein, the formulations may employ oxytocin or an oxytocin analog in any of a variety of forms, including any one or combination of the subject compound's pharmaceutically acceptable salts, isomers, enantiomers, polymorphs, solvates, hydrates, and/or prodrugs. In exemplary embodiments of this disclosure, berberine is employed within the therapeutic formulations and methods for illustrative purposes.

The pharmaceutical compositions of the present disclosure may be administered by any means that achieves their intended therapeutic or prophylactic purpose. Suitable routes of administration include, but are not limited to, oral, buccal, nasal, aerosol, topical, transdermal, mucosal, injectable, slow release, controlled release, iontophoresis, sonophoresis, and other conventional delivery routes, devices and methods. Injectable delivery methods are also contemplated, including but not limited to, intravenous, intramuscular, intraperitoneal, intraspinal, intrathecal, intracerebroventricular, intraarterial, and subcutaneous injection.

Pharmaceutical dosage forms of the oxytocin analog of the present disclosure include excipients recognized in the art of pharmaceutical compounding as being suitable for the preparation of dosage units as discussed above. Such excipients include, without intended limitation, binders, fillers, lubricants, emulsifiers, suspending agents, sweeteners, flavorings, preservatives, buffers, wetting agents, disintegrants, tonicifiers, effervescent agents and other conventional excipients and additives.

A "buffer" is generally used to maintain the pH of a solution at a nearly constant value. A buffer maintains the pH of a solution, even when small amounts of strong acid or strong base are added to the solution, by preventing or neutralizing large changes in concentrations of hydrogen and hydroxide ions. A buffer generally consists of a weak acid and its appropriate salt (or a weak base and its appropriate salt). The appropriate salt for a weak acid contains the same negative ion as present in the weak acid (see Lagowski, *Macmillan Encyclopedia of Chemistry*, Vol. 1, Simon & Schuster, New York, 1997, p. 273-4). The Henderson-Hasselbach Equation, $pH=pKa+\log 10 [A-]/[HA]$, is used to describe a buffer, and is based on the standard equation for weak acid dissociation, $HA \leftrightharpoons H^+ + A^-$. Examples of commonly used buffer sources include the following: glutamate, acetate, citrate, glycine, histidine, arginine, lysine, methionine, lactate, formate, glycolate, tartrate, phosphate and mixtures thereof.

The "buffer capacity" means the amount of acid or base that can be added to a buffer solution before a significant pH change will occur. If the pH lies within the range of pK−1 and pK+1 of the weak acid the buffer capacity is appreciable, but outside this range it falls off to such an extent as to be of little value. Therefore, a given system only has a useful buffer action in a range of one pH unit on either side of the pK of the weak acid (or weak base) (see Dawson, *Data for Biochemical Research*, Third Edition, Oxford Science Publications, 1986, p. 419). Generally, suitable concentrations are chosen so that the pH of the solution is close to the pKa of the weak acid (or weak base) (see Lide, *CRC Handbook of Chemistry and Physics*, 86th Edition, Taylor & Francis Group, 2005-2006, p. 2-41). Further, solutions of strong acids and bases are not normally classified as buffer solutions, and they do not display buffer capacity between pH values 2.4 to 11.6.

In one embodiment, carbetocin or other oxytocin analog will be combined with a solubilizer, surfactant, tonicifiers, preservatives, buffers, and chelator. Such excipients include, but are not limited to, methyl-β-cyclodextrin (Me-β-CD), edetate disodium (EDTA), arginine, sorbitol, NaCl, methylparaben sodium (MP), propylparaben sodum (PP), chlorobutanol (CB), benzyl alcohol, zinc chloride, ethyl alcohol, didecanoyl L-α-phosphatidylcholine (DDPC), polysorbate, lactose, citrate, tartrate, acetate, and or phosphate. Exemplary surfactants additionally include, but are not limited to, DMSO, Tween™ (including but not limited to, Tween 80 (polysorbate 80) and Tween 20 (polysorbate 20), Pluronics™ and other pluronic acids, including but not limited to, pluronic acid F68 (poloxamer 188), PEG; polyethers based upon poly (ethylene oxide)-poly(propylene oxide)-poly(ethylene oxide), i.e. (PEO-PPO-PEO), or poly(propylene oxide)-poly (ethylene oxide)-poly(propylene oxide), i.e. (PPO-PEO-PPO), or a combination thereof. In another embodiment, the composition contains a solubilizer in combination with carbetocin or other oxytocin analog. In a further embodiment, the composition contains a surfactant in combination with carbetocin or other oxytocin analog. In yet another embodiment, the composition contains a chelator in combination with carbetocin or other oxytocin analog. Compositions of the present disclosure may further contain combinations of solubilizers, surfactants and chelators. For example, the composition of the present disclosure may contain methyl-β-cyclodextrin and edetate disodium in combination with carbetocin or other oxytocin analog.

As the active ingredient of the pharmaceutical formulation, carbetocin is highly soluble in aqueous solutions. For example, its concentration in an aqueous solution can as high as about 90 mg/mL. In one embodiment, the present pharmaceutical formulation is an aqueous solution. That is, the pharmaceutical formulation has water as the solvent. In one embodiment of the pharmaceutical formulation, the solubilizer is at such a concentration that it enhances the intranasal delivery of carbetocin. In other embodiments of the pharmaceutical formulation, the solubilizer in combination with one or more other ingredients, such as chelating agent (a.k.a. chelator), stabilizing agent, tonicifier, preservative, buffer, and/or alkalizing or acidifying agent, enhance the intranasal delivery of carbetocin.

Inasmuch as the solubilizer, optionally in combination with one or more other ingredients, enhances the intranasal delivery of carbetocin, in one embodiment of the present invention, the pharmaceutical composition does not contain a permeabilizing agent which can enhance mucosal delivery of an active ingredient, such as carbetocin. The permeabilizing agent reversibly enhances mucosal epithelial paracellular transport, typically by modulating epithelial junctional structure and/or physiology at a mucosal epithelial surface in the subject. This effect typically involves inhibition by the permeabilizing agent of homotypic or heterotypic binding between epithelial membrane adhesive proteins of neighboring epithelial cells. Target proteins for this blockade of homotypic or heterotypic binding can be selected from various related junctional adhesion molecules (JAMs), occludins, or claudins. The permeabilizing agent is typically a peptide or peptide analog or mimetic, often selected or derived from an extracellular domain of a mammalian JAM, occludin or claudin protein.

The active ingredient of the pharmaceutical formulation, such as carbetocin, is mostly stable at a pH from about 4 to about 6. In some embodiments of the present invention, the pH of the pharmaceutical formulation is from about 4.5 to about 5.5, about 4.5±3; 5.0±3; or 5.5±3.

The compositions of this disclosure for treating neurological and psychiatric disorders including autism spectrum disorders and related disorders can thus include any one or combination of the following: a pharmaceutically acceptable carrier or excipient; other medicinal agent(s); pharmaceutical agent(s); adjuvants; buffers; solubilizers, surfactants, chelators, preservatives; diluents; and various other pharmaceutical additives and agents known to those skilled in the art. These additional formulation additives and agents will often be biologically inactive and can be administered to patients without causing deleterious side effects or interactions with the active agent.

If desired, the oxytocin analogs of this disclosure can be administered in a controlled release form by use of a slow release carrier, such as a hydrophilic, slow release polymer. Exemplary controlled release agents in this context include, but are not limited to, hydroxypropyl methyl cellulose, having a viscosity in the range of about 100 cps to about 100,000 cps.

Viscosity enhancing or suspending agents may affect the rate of release of a drug from the dosage formulation and absorption. Some examples of the materials which can serve as pharmaceutically acceptable viscosity enhancing agents are methylcellulose (MC); hydroxypropylmethylcellulose (HPMC); carboxymethylcellulose (CMC); cellulose; gelatin; starch; heta starch; poloxamers; pluronics; sodium CMC; sorbitol; acacia; povidone; carbopol; polycarbophil; chitosan; chitosan microspheres; alginate microspheres; chitosan glutamate; amberlite resin; hyaluronan; ethyl cellulose; maltodextrin DE; drum-dried way maize starch (DDWM); degradable starch microspheres (DSM); deoxyglycocholate (GDC); hydroxyethyl cellulose (HEC); hydroxypropyl cellulose (HPC); microcrystalline cellulose (MCC); polymethacrylic acid and polyethylene glycol; sulfobutylether B cyclodextrin; cross-linked eldexomer starch biospheres; sodiumtaurodihydrofusidate (STDHF); N-trimethyl chitosan chloride (TMC); degraded starch microspheres; amberlite resin; chistosan nanoparticles; spray-dried crospovidone; spray-dried dextran microspheres; spray-dried microcrystalline cellulose; and cross-linked eldexomer starch microspheres.

Oxytocin or oxytocin analog compositions of this disclosure will often be formulated and administered in an oral dosage form, optionally in combination with a carrier or other additive(s). Suitable carriers common to pharmaceutical formulation technology include, but are not limited to, microcrystalline cellulose, lactose, sucrose, fructose, glucose dextrose, or other sugars, di-basic calcium phosphate, calcium sulfate, cellulose, methylcellulose, cellulose derivatives, kaolin, mannitol, lactitol, maltitol, xylitol, sorbitol, or other sugar alcohols, dry starch, dextrin, maltodextrin or other polysaccharides, inositol, or mixtures thereof. Exemplary unit oral dosage forms for use in this disclosure include tablets, which may be prepared by any conventional method of preparing pharmaceutical oral unit dosage forms can be utilized in preparing oral unit dosage forms. Oral unit dosage forms, such as tablets, may contain one or more conventional additional formulation ingredients, including, but are not limited to, release modifying agents, glidants, compression aides, dis integrants, lubricants, binders, flavors, flavor enhancers, sweeteners and/or preservatives. Suitable lubricants include stearic acid, magnesium stearate, talc, calcium stearate, hydrogenated vegetable oils, sodium benzoate, leucine carbowax, magnesium lauryl sulfate, colloidal silicon dioxide and glyceryl monostearate. Suitable glidants include colloidal silica, fumed silicon dioxide, silica, talc, fumed silica, gypsum and glyceryl monostearate. Substances which may be used for coating include hydroxypropyl cellulose, titanium oxide, talc, sweeteners and colorants. The aforementioned effervescent agents and disintegrants are useful in the formulation of rapidly disintegrating tablets known to those skilled in the art. These typically disintegrate in the mouth in less than one minute, and preferably in less than thirty seconds. By effervescent agent is meant a couple, typically an organic acid and a carbonate or bicarbonate. Such rapidly acting dosage forms would be useful, for example, in the prevention or treatment of acute attacks of panic disorder.

Additional oxytocin or oxytocin analog compositions of this disclosure can be prepared and administered in any of a variety of inhalation or nasal delivery forms known in the art. Devices capable of depositing aerosolized oxytocin formulations in the sinus cavity or pulmonary alveoli of a patient include metered dose inhalers, nebulizers, dry powder generators, sprayers, and the like. Pulmonary delivery to the lungs for rapid transit across the alveolar epithelium into the blood stream may be particularly useful in treating impending episodes of seizures or panic disorder. Methods and compositions suitable for pulmonary delivery of drugs for systemic effect are well known in the art. Suitable formulations, wherein the carrier is a liquid, for administration, as for example, a nasal spray or as nasal drops, may include aqueous or oily solutions of oxytocin or oxytocin analogs and any additional active or inactive ingredient(s).

Intranasal delivery permits the passage of such a compound to the blood stream directly after administering an effective amount of the compound to the nose, without requiring the product to be deposited in the lung. In addition, intranasal delivery can achieve direct, or enhanced, delivery of the active compound to the central nervous system. In these and other embodiments, intranasal administration of the compounds of this disclosure may be advantageous for treating sudden onset anxiety disorders, such as panic disorder. Typically, the individual suffering from generalized anxiety disorder and prone to attacks of panic disorder is able to sense when such an attack is imminent. At such times, it is particularly desirable to be able to administer compounds of this disclosure in a form that is convenient even in a public setting, and that yields rapid absorption and central nervous system delivery.

For intranasal and pulmonary administration, a liquid aerosol formulation will often contain an active compound of this disclosure combined with a dispersing agent and/or a physiologically acceptable diluent. Alternative, dry powder aerosol formulations may contain a finely divided solid form of the subject compound and a dispersing agent allowing for the ready dispersal of the dry powder particles. With either liquid or dry powder aerosol formulations, the formulation must be aerosolized into small, liquid or solid particles in order to ensure that the aerosolized dose reaches the mucous membranes of the nasal passages or the lung. The term "aerosol particle" is used herein to describe a liquid or solid particle suitable of a sufficiently small particle diameter for nasal (in a range of from about 10 microns) or pulmonary (in a range of from about 2-5 microns) distribution to targeted mucous or alveolar membranes. Other considerations include the construction of the delivery device, additional components in the formulation, and particle characteristics. These aspects of nasal or pulmonary administration of drugs are well known in the art, and manipulation of formulations, aerosolization means, and construction of delivery devices, is within the level of ordinary skill in the art.

Yet additional compositions and methods of this disclosure are provided for topical administration of oxytocin or oxytocin analogs for treating neurological and psychiatric disorders including autism spectrum disorders, related disorders and symptoms of such disorders.

Topical compositions may comprise oxytocin or oxytocin analogs and any other active or inactive component(s) incorporated in a dermatological or mucosal acceptable carrier, including in the form of aerosol sprays, powders, dermal patches, sticks, granules, creams, pastes, gels, lotions, syrups, ointments, impregnated sponges, cotton applicators, or as a solution or suspension in an aqueous liquid, non-aqueous liquid, oil-in-water emulsion, or water-in-oil liquid emulsion. These topical compositions may comprise oxytocin or oxytocin analogs dissolved or dispersed in a portion of a water or other solvent or liquid to be incorporated in the topical composition or delivery device. It can be readily appreciated that the transdermal route of administration may be enhanced by the use of a dermal penetration enhancer known to those skilled in the art. Formulations suitable for such dosage forms incorporate excipients commonly utilized therein, particularly means, for example, structure or matrix, for sustaining the absorption of the drug over an extended period of time, for example 24 hours. A once-daily transdermal patch is particularly useful for a patient suffering from generalized anxiety disorder.

Yet additional oxytocin or oxytocin analogs are provided for parenteral administration, including aqueous and non-aqueous sterile injection solutions which may optionally contain anti-oxidants, buffers, bacteriostats and/or solutes which render the formulation isotonic with the blood of the mammalian subject; and aqueous and non-aqueous sterile suspensions which may include suspending agents and/or thickening agents. The formulations may be presented in unit-dose or multi-dose containers. Oxytocin or oxytocin analogs may also include polymers for extended release following parenteral administration. Extemporaneous injection solutions, emulsions and suspensions may be prepared from sterile powders, granules and tablets of the kind previously described. Preferred unit dosage formulations are those containing a daily dose or unit, daily sub-dose, as described herein above, or an appropriate fraction thereof, of the active ingredient(s).

In more detailed embodiments, oxytocin or oxytocin analogs may be encapsulated for delivery in microcapsules, microparticles, or microspheres, prepared, for example, by coacervation techniques or by interfacial polymerization, for example, hydroxymethylcellulose or gelatin-microcapsules and poly(methylmethacylate) microcapsules, respectively, in colloidal drug delivery systems (e.g., liposomes, albumin microspheres, microemulsions, nano-particles and nanocapsules) or in macroemulsions.

As noted above, in certain embodiments the methods and compositions of this disclosure may employ pharmaceutically acceptable salts, for example, acid addition or base salts of the above-described oxytocin or oxytocin analog. Examples of pharmaceutically acceptable addition salts include inorganic and organic acid addition salts. Suitable acid addition salts are formed from acids which form non-toxic salts, for example, hydrochloride, hydrobromide, hydroiodide, sulphate, hydrogen sulphate, nitrate, phosphate, and hydrogen phosphate salts. Additional pharmaceutically acceptable salts include, but are not limited to, metal salts such as sodium salts, potassium salts, cesium salts and the like; alkaline earth metals such as calcium salts, magnesium salts and the like; organic amine salts such as triethylamine salts, pyridine salts, picoline salts, ethanolamine salts, triethanolamine salts, dicyclohexylamine salts, N,N'-dibenzylethylenediamine salts and the like; organic acid salts such as acetate, citrate, lactate, succinate, tartrate, maleate, fumarate, mandelate, acetate, dichloroacetate, trifluoroacetate, oxalate, and formate salts; sulfonates such as methanesulfonate, benzenesulfonate, and p-toluenesulfonate salts; and amino acid salts such as arginate, asparginate, glutamate, tartrate, and gluconate salts. Suitable base salts are formed from bases that form non-toxic salts, for example, aluminum, calcium, lithium, magnesium, potassium, sodium, zinc and diethanolamine salts.

The pharmaceutical agents of this disclosure may be administered parenterally, for example, intravenously, intramuscularly, subcutaneously or intraperitoneally. The parenteral preparations may be solutions, dispersions or emulsions suitable for such administration. The subject agents may also be formulated into polymers for extended release following parenteral administration. Pharmaceutically acceptable formulations and ingredients will typically be sterile or readily sterilizable, biologically inert, and easily administered. Such polymeric materials are well known to those of ordinary skill in the pharmaceutical compounding arts. Parenteral preparations typically contain buffering agents and preservatives, and may be lyophilized to be reconstituted at the time of administration.

This disclosure will also be understood to encompass methods and compositions comprising oxytocin or oxytocin analogs using in vivo metabolic products of the said compounds (either generated in vivo after administration of the subject precursor compound, or directly administered in the form of the metabolic product itself). Such products may result, for example, from the oxidation, reduction, hydrolysis, amidation, esterification, glycosylation and the like of the administered compound, primarily due to enzymatic processes. Accordingly, this disclosure includes methods and compositions of this disclosure employing compounds produced by a process comprising contacting a berberine related or derivative compound of oxytocin or oxytocin analogs with a mammalian subject for a period of time sufficient to yield a metabolic product thereof. Such products typically are identified by preparing a radiolabeled compound of this disclosure, administering it parenterally in a detectable dose to an animal such as rat, mouse, guinea pig, monkey, or to man, allowing sufficient time for metabolism to occur and isolating its conversion products from the urine, blood or other biological samples.

The intranasal formulations of the present invention can be administered using any spray bottle or syringe. An example of a nasal spray bottle is the, "Nasal Spray Pump w/ Safety Clip," Pfeiffer SAP No. 60548, which delivers a dose of 0.1 mL per squirt and has a diptube length of 36.05 mm. It can be purchased from Pfeiffer of America of Princeton, N.J. Intranasal doses of an oxytocin or an oxytocin analog (e.g., carbetocin) can range from about 50 µg to about 500 µg, including, for example, doses of about 150 µg and about 300 µg. When administered in as an intranasal spray, the particle size of the spray may be between 10-100 µm (microns) in size, for example 20-100 µm in size.

As disclosed herein, an oxytocin, an oxytocin analog (e.g., carbetocin) can be administered intranasally using a nasal spray or aerosol. In this regard, the following definitions are useful:

Aerosol—A product that is packaged under pressure and contains therapeutically active ingredients that are released upon activation of an appropriate valve system.

Metered aerosol—A pressurized dosage form comprised of metered dose valves, which allows for the delivery of a uniform quantity of spray upon each activation.

Powder aerosol—A product that is packaged under pressure and contains therapeutically active ingredients in the form of a powder, which are released upon activation of an appropriate valve system.

Spray aerosol—An aerosol product that utilizes a compressed gas as the propellant to provide the force necessary to expel the product as a wet spray; it is generally applicable to solutions of medicinal agents in pharmaceutically acceptable aqueous solvents.

Spray—A liquid minutely divided as by a jet of air or steam. Nasal spray drug products contain therapeutically active ingredients dissolved or suspended in pharmaceutically acceptable solutions or mixtures of excipients in non-pressurized dispensers.

Metered spray—A non-pressurized dosage form consisting of valves that allow the dispensing of a specified quantity of spray (pharmaceutically acceptable) upon each activation.

Suspension spray—A pharmaceutically acceptable liquid preparation containing solid particles dispersed in a liquid vehicle and in the form of course droplets or as finely divided solids.

The fluid dynamic characterization of the pharmaceutically acceptable aerosol spray emitted by metered nasal spray pumps as a drug delivery device ("DDD"). Spray characterization is an integral part of the regulatory submissions necessary for Food and Drug Administration ("FDA") approval of research and development, quality assurance and stability testing procedures for new and existing nasal spray pumps.

Thorough characterization of the spray's geometry has been found to be the best indicator of the overall performance of nasal spray pumps. In particular, measurements of the spray's divergence angle (plume geometry) as it exits the device; the spray's cross-sectional ellipticity, uniformity and particle/droplet distribution (spray pattern); and the time evolution of the developing spray have been found to be the most representative performance quantities in the characterization of a nasal spray pump. During quality assurance and stability testing, plume geometry and spray pattern measurements are key identifiers for verifying consistency and conformity with the approved data criteria for the nasal spray pumps. In this regard, the following definitions are considered:

Plume Height—the measurement from the actuator tip to the point at which the plume angle becomes non-linear because of the breakdown of linear flow. Based on a visual examination of digital images, and to establish a measurement point for width that is consistent with the farthest measurement point of spray pattern, a height of 30 mm is defined for this study.

Major Axis—the largest chord that can be drawn within the fitted spray pattern that crosses the COMw in base units (mm).

Minor Axis—the smallest chord that can be drawn within the fitted spray pattern that crosses the COMw in base units (mm).

Ellipticity Ratio—the ratio of the major axis to the minor axis.

$D_{10}$—the diameter of droplet for which 10% of the total liquid volume of sample consists of droplets of a smaller diameter (μm).

$D_{50}$—the diameter of droplet for which 50% of the total liquid volume of sample consists of droplets of a smaller diameter (μm), also known as the mass median diameter.

$D_{90}$—the diameter of droplet for which 90% of the total liquid volume of sample consists of droplets of a smaller diameter (μm).

Span—measurement of the width of the distribution, the smaller the value, the narrower the distribution. Span is calculated as $$\frac{(D_{90} - D_{10})}{D_{50}}.$$

% RSD—percent relative standard deviation, the standard deviation divided by the mean of the series and multiplied by 100, also known as % CV.

A nasal spray device can be selected according to what is customary in the industry or acceptable by the regulatory health authorities. One example of a suitable device is described in described in U.S. application Ser. No. 10/869,649 (S. Quay and G. Brandt: Compositions and methods for enhanced mucosal delivery of Y2 receptor-binding peptides and methods for treating and preventing obesity, filed Jun. 16, 2004).

This disclosure herein will also be understood to encompass diagnostic compositions for diagnosing the risk level, presence, severity, or treatment indicia of, or otherwise managing oxytocin or oxytocin analogs in a mammalian subject, comprising contacting a labeled (e.g., isotopically labeled, fluorescent labeled or otherwise labeled to permit detection of the labeled compound using conventional methods) oxytocin or oxytocin analog to a mammalian subject (e.g., to a cell, tissue, organ, or individual) at risk or presenting with one or more symptom(s) of autism spectrum disorders or related disorders, and thereafter detecting the presence, location, metabolism, and/or binding state of the labeled compound using any of a broad array of known assays and labeling/detection methods.

In exemplary embodiments, oxytocin or an oxytocin analog such as carbetocin is isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2H$, $^3H$, $^{13}C$, $^{14}C$, $^{13}N$, $^{18}O$, $^{17}O$, $^{31}P$, $^{32}P$, $^{35}S$, $^{18}F$, and $^{36}Cl$, respectively. The isotopically-labeled compound is then administered to an individual or other subject and subsequently detected as described above, yielding useful diagnostic and/or therapeutic management data, according to conventional techniques.

EXAMPLES

The following examples are provided by way of illustration, not limitation.

Example 1

Permeation of Carbetocin Formulations

Permeation studies on varying formulations of carbetocin were completed using tracheal/bronchial epithelial cell membrane inserts. Samples were evaluated for appearance, color, clarity, pH, osmolality, cell viability using an MTT assay, cytotoxicity using an LDH assay, and transepithelial resistance (TER) and permeation.

Samples were prepared according to the formulations in Table 1. Abbreviations used for the tested excipients included: Me-β-CD is Methyl β cyclodextrin (Wacker, Munich, Germany), DDPC is didecanoyl L-α-phosphoatidylcholine (NOF Corp., White Plains, N.Y.), EDTA is edetate disodium (JTBaker, Phillipsburg, N.J.), MP/PP is methyl paraben sodium/propyl paraben sodium (Spectrum, Gardena, Calif.), CB is chlorobutanol, and Arg is arginine.

TABLE 1

Sample Composition of Carbetocin Formulations

| # | Carbetocin (mg/ml) | Me-β-CD (mg/ml) | DDPC (mg/ml) | EDTA (mg/ml) | Polysorbate 80 (mg/ml) | NaCl (mg/mL) and *values in mM | Sorbitol (mM) | Lactose (mM) | Chlorobutanol (mg/mL) | MP/PP (mg/ml) | ZnCl2 (mM) | EtOH mg/ml and *values in mM | Buffer | pH |
|---|---|---|---|---|---|---|---|---|---|---|---|---|---|---|
| 1 | 10 | 45 | 1 | 1 | 0 | 0 | 100 | 25 | 0 | 0 | 0 | 0 | 10 mM Arg | 4.00 |
| 2 | 10 | 30 | 1.7 | 2 | 0 | 4 | 0 | 0 | 0 | 0 | 0 | 0 | 0 | 4.00 |
| 3 | 10 | 0 | 0 | 2.5 | 1 | 0 | 131 | 0 | 0 | 0 | 0 | 0 | 0 | 4.00 |
| 4 | 10 | 45 | 0 | 1 | 10 | 3.5 | 0 | 0 | 0 | 0 | 0 | 0 | 10 mM Arg | 5.00 |
| 5 | 10 | 80 | 0 | 5 | 0 | 1.5 | 0 | 0 | 0 | 0 | 0 | 0 | 2.8 mM Arg | 5.25 |
| 6 | 10 | 0 | 0 | 0 | 0 | 8.75 | 0 | 0 | 0 | 0 | 0 | 0 | 10 mM acetate | 5.00 |
| 7 | 10 | 0 | 0 | 2.5 | 0 | 0 | 131 | 0 | 5 | 0 | 0 | 0 | 10 mM acetate | 4.00 |
| 8 | 10 | 0 | 0 | 5 | 0 | 0 | 90 | 0 | 5 | 0 | 0 | 0 | 10 mM Arg | 4.00 |
| 9 | 10 | 40 | 0 | 5 | 0 | 1.8 | 0 | 0 | 5 | 0 | 0 | 0 | 10 mM Arg | 5.25 |
| 10 | 2 | 0 | 0 | 2.5 | 0 | 0 | 131 | 0 | 0 | 0 | 0 | 0 | 0 | 3.7 +/- 0.2 |
| 11 | 2 | 20 | 0.5 | 5 | 0 | 0 | 0 | 0 | 0 | 0 | 0 | 0 | 0 | 3.7 +/- 0.2 |
| 12 | 2 | 40 | 0 | 5 | 0 | 0 | 0 | 0 | 5 | 0 | 0 | 0 | 0 | 3.7 +/- 0.2 |
| 13 | 2 | 0 | 0 | 5 | 0 | 0 | 0 | 0 | 0 | 0 | 0 | 0 | 0 | 3.7 +/- 0.2 |
| 14 | 2 | 10 | 0 | 5 | 0 | 0 | 131 | 0 | 5 | 0 | 0 | 0 | 0 | 3.7 +/- 0.2 |
| 15 | 2 | 0 | 0 | 2.5 | 0 | 0 | 0 | 0 | 0 | 0 | 0 | 0 | 0 | 3.7 +/- 0.2 |
| 16 | 2 | 0 | 0 | 2.5 | 0 | 0 | 0 | 0 | 0 | 0 | 0 | 0 | 0 | 3.7 +/- 0.2 |
| 17 | 2 | 40 | 1 | 5 | 0 | 0 | 0 | 0 | 0 | 0 | 0 | 0 | 0 | 3.7 +/- 0.2 |
| 18 | 2 | 40 | 0.25 | 2.5 | 0 | 0 | 0 | 0 | 0 | 0 | 0 | 0 | 0 | 3.7 +/- 0.2 |
| 19 | 2 | 10 | 0 | 0 | 0 | 0 | 0 | 0 | 0 | 0 | 0 | 0 | 0 | 3.7 +/- 0.2 |
| 20 | 2 | 40 | 0 | 5 | 0 | 0 | 0 | 0 | 5 | 0 | 0 | 0 | 0 | 3.7 +/- 0.2 |
| 21 | 2 | 40 | 0 | 5 | 0 | 40* | 0 | 0 | 0 | 0 | 0 | 0 | 10 mM Arg | 3.7 +/- 0.2 |
| 22 | 2 | 30 | 0 | 2.5 | 0 | 0 | 0 | 0 | 5 | 0 | 0 | 0 | 0 | 3.7 +/- 0.2 |
| 23 | 2 | 20 | 0.5 | 5 | 0 | 0 | 0 | 0 | 0 | 0 | 0 | 0 | 0 | 3.7 +/- 0.2 |
| 24 | 2 | 40 | 0 | 0 | 0 | 0 | 0 | 0 | 0 | 0 | 0 | 0 | 0 | 3.7 +/- 0.2 |
| 25 | 2 | 30 | 0.5 | 2.5 | 0 | 0 | 0 | 0 | 0 | 0 | 0 | 0 | 0 | 3.7 +/- 0.2 |
| 26 | 2 | 40 | 1 | 2.5 | 0 | 0 | 0 | 0 | 5 | 0 | 0 | 0 | 0 | 3.7 +/- 0.2 |
| 27 | 2 | 40 | 0 | 5 | 0 | 0 | 131 | 0 | 0 | 0 | 0 | 0 | 0 | 3.7 +/- 0.2 |
| 28 | 2 | 40 | 0.25 | 5 | 0 | 40* | 0 | 0 | 0 | 0 | 0 | 0 | 10 mM Arg | 3.7 +/- 0.2 |
| 29 | 2 | 20 | 0 | 5 | 0 | 0 | 0 | 0 | 5 | 0 | 0 | 0 | 0 | 3.7 +/- 0.2 |
| 30 | 2 | 0 | 0 | 0 | 0 | 0 | 0 | 0 | 0 | 0 | 0 | 0 | 0 | 3.7 +/- 0.2 |
| 31 | 2 | 20 | 0.25 | 0 | 0 | 0 | 0 | 0 | 0 | 0 | 0 | 0 | 0 | 3.7 +/- 0.2 |
| 32 | 2 | 10 | 0 | 3.75 | 0 | 0 | 0 | 0 | 0 | 0 | 0 | 0 | 0 | 3.7 +/- 0.2 |
| 33 | 2 | 10 | 0.25 | 2.5 | 0 | 0 | 0 | 0 | 5 | 0 | 0 | 0 | 0 | 3.7 +/- 0.2 |
| 34 | 2 | 30 | 0 | 5 | 0 | 0 | 0 | 0 | 0 | 0 | 0 | 0 | 0 | 3.7 +/- 0.2 |
| 35 | 2 | 20 | 0.5 | 5 | 0 | 0 | 0 | 0 | 5 | 0 | 0 | 0 | 0 | 3.7 +/- 0.2 |
| 36 | 2 | 40 | 0.5 | 0 | 0 | 0 | 0 | 0 | 0 | 0 | 0 | 0 | 0 | 3.7 +/- 0.2 |
| 37 | 2 | 40 | 0 | 2.5 | 0 | 0 | 0 | 0 | 0 | 0 | 0 | 0 | 0 | 3.7 +/- 0.2 |
| 38 | 2 | 5 | 0 | 5 | 0 | 57* | 0 | 0 | 5 | 0 | 0 | 0 | 0 | 3.7 +/- 0.2 |
| 39 | 2 | 30 | 1 | 5 | 0 | 52* | 0 | 0 | 5 | 0 | 0 | 0 | 0 | 3.7 +/- 0.2 |
| 40 | 2 | 0 | 0 | 3.5 | 0 | 0 | 0 | 0 | 5 | 0 | 0 | 0 | 10 mM Arg | 4.00 |
| 41 | 2 | 10 | 0 | 3.5 | 0 | 0 | 0 | 0 | 5 | 0 | 0 | 0 | 10 mM Arg | 4.00 |
| 42 | 2 | 10 | 0 | 3.5 | 0 | 0 | 104 | 0 | 0 | 0 | 0 | 0 | 10 mM Arg | 4.00 |
| 43 | 2 | 20 | 0 | 3.5 | 0 | 50* | 0 | 0 | 5 | 0 | 0 | 0 | 10 mM Arg | 4.00 |

TABLE 1-continued

Sample Composition of Carbetocin Formulations

| # | Carbetocin (mg/ml) | Me-β-CD (mg/ml) | DDPC (mg/ml) | EDTA (mg/ml) | Polysorbate 80 (mg/ml) | NaCl (mg/mL) and *values in mM | Sorbitol (mM) | Lactose (mM) | Chlorobutanol (mg/mL) | MP/PP (mg/ml) | ZnCl2 (mM) | EtOH mg/ml and *values in mM | Buffer | pH |
|---|---|---|---|---|---|---|---|---|---|---|---|---|---|---|
| 44 | 4 | 10 | 0 | 3.5 | 0 | 52* | 0 | 0 | 5 | 0 | 0 | 0 | 10 mM Arg | 4.00 |
| 45 | 3 | 10 | 0 | 3.5 | 0 | 65* | 0 | 0 | 0 | 0.33/0.17 | 0 | 0 | 10 mM Arg | 4.00 |
| 46 | 3 | 10 | 0 | 3.5 | 0 | 60* | 0 | 0 | 2.5 | 0 | 0 | 0 | 10 mM Arg | 4.00 |
| 47 | 3 | 10 | 0 | 3.5 | 0 | 52* | 0 | 0 | 5 | 0 | 0 | 0 | 10 mM Arg | 4.00 |
| 48 | 3 | 10 | 0 | 3.5 | 0 | 50* | 0 | 0 | 5 | 0.33/0.17 | 0 | 0 | 10 mM Arg | 4.00 |
| 49 | 3 | 0 | 0 | 3.5 | 0 | 70* | 0 | 0 | 0 | 0.33/0.17 | 0 | 0 | 10 mM Arg | 4.00 |
| 50 | 3 | 20 | 0 | 3.5 | 0 | 60* | 0 | 0 | 0 | 0.33/0.17 | 0 | 0 | 10 mM Arg | 4.00 |
| 51 | 2 | 40 | 0 | 5 | 0 | 40* | 0 | 0 | 5 | 0 | 0 | 0 | 10 mM Arg | 4.50 |
| 52 | 2 | 0 | 0 | 0 | 0 | 0 | 0 | 0 | 0 | 0 | 0 | 0 | 10 mM Arg | 7.00 |
| 53 | 2 | 10 | 0 | 0 | 0 | 60* | 0 | 0 | 0 | 0 | 2 | 1 | 5 mM Arg | 4.0 |
| 54 | 2 | 10 | 0 | 2.5 | 0 | 50* | 0 | 0 | 0 | 0 | 2 | 1 | 5 mM Arg | 4.0 |
| 55 | 2 | 10 | 0 | 2.5 | 0 | 40* | 0 | 0 | 0 | 0 | 2 | 1 | 15 mM Arg | 4.0 |
| 56 | 2 | 20 | 0 | 3.75 | 0 | 65* | 0 | 0 | 0 | 0 | 0 | 0 | 10 mM Arg | 4.0 |
| 57 | 2 | 0 | 0 | 3.75 | 0 | 25* | 0 | 0 | 0 | 0 | 4 | 2 | 0 | 4.0 |
| 58 | 2 | 0 | 0 | 0 | 0 | 45* | 0 | 0 | 0 | 0 | 0 | 2 | 0 | 4.0 |
| 59 | 2 | 0 | 0 | 0 | 0 | 85* | 0 | 0 | 0 | 0 | 0 | 0 | 0 | 4.0 |
| 60 | 2 | 20 | 0 | 3.75 | 0 | 10* | 0 | 0 | 0 | 0 | 4 | 2 | 10 mM Arg | 4.0 |
| 61 | 2 | 0 | 0 | 0 | 0 | 30* | 0 | 0 | 0 | 0 | 4 | 2 | 10 mM Arg | 4.0 |
| 62 | 2 | 10 | 0 | 4 | 0 | 45* | 0 | 0 | 0 | 0 | 0 | 1 | 5 mM Arg | 4.0 |
| 63 | 2 | 0 | 0 | 3.75 | 0 | 70* | 0 | 0 | 0 | 0 | 4 | 0 | 10 mM Arg | 4.0 |
| 64 | 2 | 20 | 0 | 0 | 0 | 80* | 0 | 0 | 0 | 0 | 4 | 2 | 10 mM Arg | 4.0 |
| 65 | 2 | 10 | 0 | 3.5 | 0 | 45* | 0 | 0 | 0 | 0 | 0 | 0 | 5 mM Arg | 4.0 |
| 66 | 2 | 10 | 0 | 2.5 | 0 | 80* | 0 | 0 | 0 | 0 | 0 | 1 | 5 mM Arg | 4.0 |
| 67 | 2 | 10 | 0 | 2.5 | 0 | 50* | 0 | 0 | 0 | 0 | 2 | 0 | 5 mM Arg | 4.0 |
| 68 | 2 | 10 | 0 | 2.5 | 0 | 55* | 0 | 0 | 0 | 0 | 2 | 1 | 5 mM Arg | 4.0 |
| 69 | 2 | 0 | 0 | 0 | 0 | 90* | 0 | 0 | 0 | 0 | 0 | 1 | 0 | 4.0 |
| 70 | 2 | 0 | 0 | 3.75 | 0 | 20* | 0 | 0 | 0 | 0 | 0 | 2 | 10 mM Arg | 4.0 |
| 71 | 2 | 0 | 0 | 3.75 | 0 | 85* | 0 | 0 | 0 | 0 | 0 | 2 | 10 mM Arg | 4.0 |
| 72 | 2 | 20 | 0 | 0 | 0 | 35* | 0 | 0 | 0 | 0 | 4 | 0 | 0 | 4.0 |
| 73 | 2 | 20 | 0 | 3.75 | 0 | 20* | 0 | 0 | 0 | 0 | 0 | 2 | 0 | 4.0 |
| 74 | 2 | 20 | 0 | 0 | 0 | 25* | 0 | 0 | 0 | 0 | 0 | 2 | 10 mM Arg | 4.0 |
| 75 | 2 | 10 | 0 | 2.5 | 0 | 65* | 0 | 0 | 0 | 0 | 0 | 0.5 | 5 mM Arg | 4.0 |
| 76 | 2 | 0 | 0 | 2.5 | 0 | 55* | 0 | 0 | 0 | 0 | 2 | 1 | 5 mM Arg | 4.0 |
| 77 | 2 | 0 | 0 | 2.5 | 0 | 55* | 0 | 0 | 0 | 0 | 0 | 1 | 5 mM Arg | 4.0 |
| 78 | 2 | 20 | 0 | 3.75 | 0 | 75* | 0 | 0 | 0 | 0 | 2 | 0 | 0 | 4.0 |
| 79 | 2 | 20 | 0 | 0 | 0 | 85* | 0 | 0 | 0 | 0 | 0 | 0 | 0 | 4.0 |
| 80 | 2 | 40 | 0 | 5 | 0 | 40* | 0 | 0 | 5 | 0 | 4 | 0 | 10 mM Arg | 4.0 |
| 81 | 2 | 0 | 0 | 0 | 0 | 95* | 0 | 0 | 0 | 0 | 0 | 0 | 0 | 4.0 | pH was measured using a Cole Parmer semi-micro NMR tube glass pH probe with Orion 520Aplus pH meter (Thermo Electron Corp, Waltham, Mass.). The pH was adjusted using 2N HCL or 2N NaOH as necessary to meet the parameters specified in the formulation.

Osmolality was measured with an advanced multichannel osmometer, Model 2020 (Advanced Instruments, Inc., Norwood, Mass.).

Tracheal/bronchial epithelial cell membrane inserts (Epi-Airway, MatTek Corp., Ashland, Mass.) were received the day before the experiment. Each tissue insert was placed in a well of a 6 well plate which contained 0.9 ml of serum free media and cultured at 37° C. for 24 hours to allow the tissues to equilibrate. The day of the experiment, transepithelial electrical resistance measurements were taken for each insert using a Tissue Resistance Measurement Chamber connected to an Epithelial Voltohmeter (World Precision Instruments, Inc., Sarasota, Fla.).

After the background transepithelial electrical resistance was determined, 1 ml of media was placed in the bottom of each well in a six well plate. The inserts were inverted and drained and placed into new wells with fresh media. For samples 1-12, 100 µl of the formulation to be tested was then added to an insert. For Samples 13-92, 25 µl of the formulation was added to each insert. The inserts were placed in a shaking incubator at 100 rpm and 37° C. for one hour. The tissue inserts were then removed from the incubator. 200 µl of fresh media was placed in each well of a 24 well plate and the inserts were transferred. The basolateral solution remaining in the six well plate after removal of the insert was harvested and stored at 2-8° C. until it was assayed by ETA (Oxytocin Enzyme Immunoassay Kit: High Sensitivity, Peninsula Laboratories Inc, San Carlos, Calif.). Formulation 5 had a permeation of 21.2%. Formulations 1, 2, 3, and 4 had permeations of 15.7%, 14.4%, 9.6% and 17.9%, respectively. These permeation levels are a significant increase over the permeation of carbetocin without enhancer excipients. The permeation of carbetocin alone (in just buffer and salt) is less than 1.0%.

200 μl of fresh media was gently added to each tissue insert in the 24 well plate and the plate was placed no a shaker table at room temperature for 5 minutes. 150 μl of apical solution was removed from each insert and reserved for a lactase dehydrogenase assay. The inserts were then washed with 300 μl of media; 300 μl of new media was added to each insert, the inserts were incubated for 20 minutes at room temperature and the transepithelial electrical resistance was measured.

The inserts are then transferred into a new 24 well plate containing no media and the appropriate amount of media was added to the apical surface in order to total 300 μl. The inserts were then shaken for five minutes at 100 RPM at room temperature. 50-100 μl of the apical media were then removed, placed in 0.5 to 1.5 tubes and kept at 2-8° C. until needed.

The samples were then centrifuged at 1000 rpm for 5 minutes. 2 μl of the supernatant was removed and added to a 96 well plate. 48 μl of media was then used to dilute the supernatant to make a 25× dilution and each sample was assayed in triplicate for LDH loss using a CytoTox 96 Cytotoixcity Assay Kit (Promega Corp., Madison, Wis.).

For analysis of the basolateral media, 50 μl of the reserved 150 μl solution was loaded into a 96 well assay plate and assayed in triplicate.

Cell viability was assessed using an MTT assay kit (MatTek Corp., Ashland, Mass.). MTT concentrate was thawed and diluted with media at a ratio of 2 ml MTT:8 ml media. 300 μl MTT-media mix was added to each well of a 24 well plate. Tissue culture inserts were drained and transferred to the MTT containing well and incubated at 37° C. in the dark for three hours. After incubation, each insert was removed from the plate, and then immersed in the wells of a fresh 24-well plate containing 2 ml extractant solution. The plate was then covered and incubated overnight at room temperature in the dark. The liquid in each insert was then decanted back into the well from which it was taken and the insert was discarded. 50 μl of the exractant solution from each well was then pipetted in triplicate into a 96 well plate and diluted with the addition of 150 μl of fresh extractant solution. The optical density of the samples was then measured at 550 nm on a Spectramax plate reader (Molecular Devices, Sunnyvale, Calif.) using SpectraPro software.

The permeation results show that EDTA was a significant factor in increasing permeation and sorbitol appeared to reduce permeation of carbetocin. The optimal formulations as predicted by DOE included EDTA and Me-β-CD. Additionally, EDTA was the most significant factor in cytotoxicity. In combination with Me-β-CD and EDTA, ethanol also enhanced permeation.

Example 2

First Pharmacokinetic Study in Rabbits

Rabbits were treated with carbetocin by intranasal administration of pharmaceutical compositions. Table 2 shows the formulations that were tested:

TABLE 2

PK Study Carbetocin Formulations

| Group # | Carbetocin (mg/ml) | Me-β-CD (mg/ml) | EDTA (mg/ml) | Arg (mM) | Sorbitol (mM) | NaCl (mM) | CB (mg/ml) | pH | Carbetocin % Label Claim |
|---|---|---|---|---|---|---|---|---|---|
| 1 | 0.03 | 0 | 0 | 10 | 0 | 150 | 0 | 7 | 87.1 |
| 2 | 2 | 0 | 3.5 | 10 | 0 | 57 | 5 | 4 | 101.2 |
| 3 | 2 | 10 | 3.5 | 10 | 0 | 52 | 5 | 4 | 110.2 |
| 4 | 2 | 10 | 3.5 | 10 | 104 | 0 | 5 | 4 | 103.0 |
| 5 | 2 | 20 | 3.5 | 10 | 0 | 50 | 5 | 4 | 102.0 |
| 6 | 4 | 10 | 3.5 | 10 | 0 | 52 | 5 | 4 | 99.2 |

Results for PK Data, % Bioavailability (% BA), and % CV are shown in Table 3, Table 4, and Table 6, respectively. The following results were obtained from measurements of mean blood levels:

TABLE 3

PK Results for Carbetocin in Rabbits

| Group # | Formulation | Dose (µg/kg) | Tmax (min) | Cmax (pg/mL) | $AUC_{last}$ (min*pg/mL) |
|---|---|---|---|---|---|
| 1 | IM | 3 | 9 | 5070.40 | 184237.00 |
| 2 | IN | 30 | 29 | 1244.80 | 46724.50 |
| 3 | IN | 30 | 27 | 1098.80 | 67283.50 |
| 4 | IN | 30 | 30 | 692.80 | 32378.00 |
| 5 | IN | 30 | 27 | 1678.20 | 51911.50 |
| 6 | IN | 60 | 30 | 3090.40 | 169038.00 |

TABLE 4

Percent Bioavailability for Carbetocin in Rabbits

| Group # | Formulation | Dose (µg/kg) | $AUC_{last}$ (min*pg/mL) | % BA |
|---|---|---|---|---|
| 1 | IM | 3 | 184237.00 | N/A |
| 2 | IN | 30 | 46724.50 | 2.54 |
| 3 | IN | 30 | 67283.50 | 3.65 |
| 4 | IN | 30 | 32378.00 | 1.76 |
| 5 | IN | 30 | 51911.50 | 2.82 |
| 6 | IN | 60 | 169038.00 | 4.59 |

The formulation (Group No. 6) "10 Me-β-CD, hi dose" produced the highest carbetocin exposure, as well as the highest relative bioavailability (about 4.6% rel BA). In this case the higher dose was achieved by maintaining dose volume constant and increasing drug concentration. All other formulations exhibited relative bioavailability in the range of from about 1.8 to about 3.7%.

A comparison of Me-β-CD concentrations of 0 and 20 mg/ml (Group Nos. 2 and 5, respectively) revealed an increase in $C_{max}$ (1245 and 1678 pg/ml, respectively) and $AUC_{last}$ (46725 and 51912 min*pg/ml, respectively) with higher concentrations of Me-β-CD. However, the sample with the mid-concentration of Me-β-CD (Group #3), "10 Me-β-CD", resulted in the lowest $C_{max}$ (1099 pg/ml) and highest $AUC_{last}$ (67284 min*pg/ml) when compared to the "0 Me-β-CD" and "20 Me-β-CD".

Formulations containing sorbitol were observed in vitro to decrease carbetocin permeation compared to salt-containing formulations (see results presented in Table 5). These in vitro studies were performed as disclosed in Example 1. This unexpected tonicifier effect was also observed in the current in vivo study. Specifically, a comparison of Groups 3 and 4 reveals that the salt-tonicified formulation produced a higher $AUC_{last}$ and $C_{max}$ (67284 min*pg/ml and 1099 pg/ml, respectively) than the sorbitol-containing formulation (32378 min*pg/ml and 693 pg/ml, respectively).

TABLE 5

In Vitro Permeation Studies

| | TER | | Permeation | | MTT | | Apical LDH | |
|---|---|---|---|---|---|---|---|---|
| Group | T = 0 | T = 60 min | % | % std dev | % | % std dev | % | % std dev |
| 2 | 579.5 | 18.2 | 22.0% | 12.0% | 102.5 | 12.6 | 13.42 | 6.1 |
| 3 | 662.2 | 23.3 | 21.9% | 5.3% | 101.0 | 12.3 | 10.63 | 1.4 |
| 4 | 596.2 | 16.7 | 12.3% | 0.8% | 96.6 | 14.6 | 9.45 | 1.4 |
| 5 | 696.7 | 19.8 | 26.7% | 5.8% | 104.6 | 13.0 | 10.12 | 1.4 |
| 6 | 647.0 | 21.5 | 25.0% | 10.4% | 102.7 | 14.0 | 9.58 | 1.4 |

As the carbetocin concentration was increased from 2 to 4 mg/ml, a dose response was observed, with an $AUC_{last}$ increase from 67284 min*pg/ml (Group 3) to 169038 min*pg/ml (Group 6). This corresponded to a slight increase in relative BA from about 3.7 to about 4.8%. In addition, increasing the dose allowed the IN carbetocin formulation to match the $AUC_{last}$ of the IM dose (169038 vs. 184237 min*pg/ml, respectively). It was also observed that the $T_{max}$ for the IN formulations was longer ($T_{max}$=27-30 min in this study compared to ~15 min for typical IN dosing).

TABLE 6

% CV for Carbetocin in Rabbits

| Group # | Formulation | Dose (µg/kg) | Tmax (min) | Cmax (pg/ml) | $AUC_{last}$ (min*pg/ml) |
|---|---|---|---|---|---|
| 1 | IM | 3 | 46.48 | 27.04 | 12.73 |
| 2 | IN | 30 | 42.93 | 101.09 | 67.41 |
| 3 | IN | 30 | 24.85 | 30.94 | 42.83 |
| 4 | IN | 30 | 0.00 | 27.25 | 33.13 |
| 5 | IN | 30 | 24.85 | 46.69 | 51.75 |
| 6 | IN | 60 | 35.36 | 27.64 | 15.86 |

Statistical analysis of the in vivo data showed that all formulations except the "10 Me-β-CD, hi dose" were statistically different from the IM control for $AUC_{last}$. Additionally, all IN formulations dosed at 2 mg/mL carbetocin were statistically different from the IM control and not statistically different from each other for $C_{max}$, $AUC_{last}$, and $T_{max}$. The "high dose," 4 mg/mL carbetocin formulation was statistically similar to the IM control and not statistically different from all other formulations for $T_{max}$. For example, the P-value for $AUC_{last}$ and $C_{max}$ for Groups 2-5 was 0.0001 and for Group 6 was 0.8119 and 0.0091 respectively. The P-value for $T_{max}$ of Group 2 was 0.0023, Group 2 was 0.0062, Group 3 was 0.0014, Group 5 was 0.0062 and Group 6 was 0.0014. The formulation #6 had the highest bioavailablity (about 5%). The results show a carbetocin bioavailabily of about 4-5% can be achieved by the intranasal pharmaceutical formulations of this disclosure.

The in vivo data presented in Tables 3, 4 and 6 was evaluated in context with the in vitro data presented in Table 5 for a possible in vivo-in vitro correlation (IVIVC), shown graphically in FIG. 1. A correlation was observed between in vivo bioavailability and in vitro permeation of carbetocin (R=0.7608, FIG. 1). In addition, a strong IVIVC was observed comparing either in vivo $AUC_{last}$ or $C_{max}$ with in vitro carbetocin permeation ($R^2$=0.9236 and 0.9881, respectively). These correlations suggest the in vitro permeation observed in this study was predictive of the exposure observed in vivo in rabbits. Significantly, the non-obvious effect of tonicifier (salt vs. sugar) influencing permeation in vitro was also predictive of the tonicifier effect observed in vivo; formulations with sodium chloride produced a higher permeation in vitro and greater exposure in vivo.

Example 3

Second Pharmacokinetic Study for Intramuscular and Intranasal Administration of Carbetocin in Rabbits A second rabbit PK study was performed in order to repeat testing of the formulations evaluated in our first human clinical study, to test the effect of increasing the amount of Me-β-CD (from about 10 to about 40 mg/ml), evaluate carbetocin bioavailability in the presence of tonicity adjusting agents sorbitol and NaCl, test the impact of increasing osmolality (from about 170 to about 220 mOsm/kgH$_2$O), and test the effect of ethanol on % BA. In this study, the dosing concentration of carbetocin was also increased to 60 µg/kg (i.e., 4 µg/ml carbetocin). The formulations tested are shown in Table 7.

Prior to initiating this second in vivo study, we evaluated the formulations presented in Table 7 in vitro for the ability to reduce transepithelial resistance (TER), as well as their impact on cell viability, cytotoxicity and permeation using the tracheal/bronchial epithelial cell membrane system (EpiAirway, MatTek Corp., Ashland, Mass.), in accordance with procedures presented in Example 1.

The results from this epithelial cell in vitro study indicated that all formulations significantly reduced TER with high levels of cell viability, low levels of cytotoxicity, and carbetocin permeation levels between about 2.5% to about 24%. For example, regarding percent permeation, the formulation containing 10 mg/ml Me-β-CD plus CMC (Sample No. 8) was the best performer with a percent permeation at about 24%. The formulation designated 10 mg/ml Me-β-CD (Sample No. 2) showed a percent permeation of about 9%, the formulation designated 10 mg/ml Me-β-CD plus sorbitol (Sample No. 3) provided about 5% permeation, the formulations designated 20 mg/ml Me-β-CD (Sample No. 4) and 40 mg/ml Me-β-CD (Sample No. 5) provided about 12%, the formulation designated 10 mg/ml Me-β-CD hi osm about 4% (Sample No. 6), and the formulation designated EDTA plus EtOH (Sample No. 7) provided about 15% permeation. In this experiment, the negative control provided a percent permeation of about 2%. The results from this experiment indicate that high osmolality and tonicifier both appear to reduce permeation relative to the formulation used in our first human clinical study presented herein (see Example 8).

For this second rabbit PK study, New Zealand White Rabbits were treated with carbetocin by intramuscular (IM) or intranasal (IN) administration of pharmaceutical compositions. The study was a randomized, single treatment parallel study in eight groups of five fasted male rabbits. All animals were fasted the day before dosing by removing any remaining food in the afternoon of Day 0, and remained in the fasted state through study conclusion. All animals in the intranasal groups (Groups 2-8) were dosed with 60 µg/kg carbetocin (a dose concentration of 4.0 mg/ml and a dose volume of 0.015 ml/kg). The intramuscular group (Group 1) was dosed with 3.0 µg/kg carbetocin (a dose concentration of 0.03 mg/ml and a dose volume of 0.10 ml/kg).

25 mL of each IN formulation was prepared. All groups contained 10 mM Arginine. Groups 2-8 contain 5 mg/mL chlorobutanol (CB). IN formulations were stored in 1 cc amber glass bottles. The IM formulation was prepared and stored in 3 cc clear glass bottles. All formulations (except No. 1) also contained 5 mg/ml chlorobutanol, and were stored at 2-8° C. Table 7 shows the formulations that were tested (abbreviations: PG=propylene glycol; CMC LV=carboxymethylcellulose sodium (low viscosity, 10-50 cps); ethanol=EtOH).

TABLE 7

PK Study Carbetocin Formulations

| # | ID | Carbetocin (mg/ml) | Me-β-CD (mg/ml) | EDTA (mg/ml) | CMC LV (mg/ml) | Sorbitol (mM) | NaCl (mM) | EtOH (mg/ml) | PG (mg/ml) | pH |
|---|---|---|---|---|---|---|---|---|---|---|
| 1 | IM | 0.03 | 0 | 0 | 0 | 0 | 150 | 0 | 0 | 7.0 |
| 2 | 1% MBCD | 4 | 10 | 3.5 | 0 | 0 | 52 | 0 | 0 | 4.0 |
| 3 | 1% MBCD-Sorbitol | 4 | 10 | 3.5 | 0 | 104 | 0 | 0 | 0 | 4.0 |
| 4 | 2% MBCD | 4 | 20 | 3.5 | 0 | 0 | 50 | 0 | 0 | 4.0 |
| 5 | 4% MBCD | 4 | 40 | 3.5 | 0 | 0 | 40 | 0 | 0 | 4.0 |
| 6 | 1% MBCD | 4 | 10 | 3.5 | 0 | 0 | 86 | 0 | 0 | 4.0 |
| 7 | 0% MBCD-0.2% ETOH | 4 | 0 | 3.75 | 0 | 0 | 50 | 2 | 0 | 4.0 |
| 8 | 1% MBCD-0.1% CMCLV | 4 | 10 | 3.5 | 1.0 | 0 | 0 | 0 | 10 | 4.0 |

The Group 1 formulation was administered as a single bolus injection into one hind limb. The fur around the site of needle insertion was clipped and the skin was wiped with 70% isopropyl alcohol prior to insertion. The needle was inserted into the muscle mass over the posterior femur laterally and directed caudally to avoid the sciatic nerve. Each animal was dosed with its own needle/syringe. Tare and final weights of the dosing syringe were obtained and a net weight of the dose administered was calculated.

Groups 2-8 were administered into the left nare using a pipetteman and disposable plastic tip. The head of the animal was tilted back slightly as the dose was delivered. Dosing was made by coinciding dose administration with inspiration allowing capillary action to draw the solution into the nare. Fresh pipette tips were used between each dosing or attempted dosing. Following intranasal dose administration, the head of the animal was restrained in a tilted back position for approximately 15 seconds to prevent the loss of test article formulation from the left nare.

Following dose administration, eleven serial blood samples were obtained by direct venipuncture of a marginal ear vein at 0 (pre-dose), 5, 10, 15, 30, 45, 60, 120, and 240 minutes post-dosing. 50 µl of an aprotinin solution was added to each blood sample that contained K2 EDTA as an anticoagulant. For the IM dose group, a pre-dose, 5 minute, and 1 hour post-dose gross visual observation of the injection site was performed. For the IN dose groups, a pre-dose, 5 minute, and 1 hour post-dose examination of both nostrils was performed. PK plasma levels of carbetocin after administration of different carbetocin formulations were assayed.

A summary of the PK results for carbetocin administered to rabbits in this second PK study are shown in Table 8. IN % Bioavailability results are shown in Table 9. The following results were obtained from measurements of mean blood levels:

TABLE 8

PK Results Summary for Carbetocin in Rabbits

| Parameter | Formulation ID | No. Obs | Mean (STD) | Median | Range | CV (%) |
|---|---|---|---|---|---|---|
| AUCinf (min * pg/mL) | IM | 5 | 142393 (19607.88) | 138920 | (121680-173400.6) | 13.77 |
| | 1% MBCD | 5 | 140363.3 (75055.11) | 110774.4 | (92990.2-273337.4) | 53.47 |
| | 1% MBCD-Sorbitol | 3 | 101175.1 (40816.59) | 79138.3 | (76113.3-148273.7) | 40.34 |
| | 2% MBCD | 4 | 398767.4 (277545.41) | 354820.4 | (109565.2-775863.8) | 69.60 |
| | 4% MBCD | 5 | 182847.7 (89881.53) | 202467.9 | (56431.6-263761.4) | 49.16 |
| | 1% MBCD | 5 | 152980.5 (59363.49) | 156198.7 | (85466.5-217339.4) | 38.80 |
| | 0% MBCD-0.2% ETOH | 5 | 137436.2 (79285.95) | 151533.5 | (44080.2-223647.4) | 57.69 |
| | 1% MBCD-0.1% CMCLV | 5 | 267524.7 (257835.72) | 195123.4 | (68559.9-713829.8) | 96.38 |
| $AUC_{last}$ (min * pg/mL) | IM | 5 | 138324 (18875.93) | 136967.5 | (114945-166632.5) | 13.65 |
| | 1% MBCD | 5 | 133581 (75529) | 98692.5 | (88840-267310) | 56.54 |
| | 1% MBCD-Sorbitol | 4 | 155472.5 (119604.55) | 111097.5 | (71617.5-328077.5) | 76.93 |
| | 2% MBCD | 5 | 216248 (117463.71) | 239155 | (81542.5-334190) | 54.32 |
| | 4% MBCD | 5 | 169762 (78456.6) | 199710 | (56392.5-236257.5) | 46.22 |
| | 1% MBCD | 5 | 146853.5 (57136.36) | 150340 | (82572.5-203460) | 38.91 |
| | 0% MBCD-0.2% ETOH | 5 | 133916 (78288.02) | 150162.5 | (39725-221157.5) | 58.46 |
| | 1% MBCD-0.1% CMCLV | 5 | 259976.5 (254979.86) | 189120 | (67955-700310) | 98.08 |
| Cmax (pg/mL) | IM | 5 | 3625 (1195.63) | 3577 | (2230-5355) | 32.98 |
| | 1% MBCD | 5 | 2946.2 (2673.56) | 1462 | (1334-7558) | 90.75 |
| | 1% MBCD-Sorbitol | 4 | 1928.3 (507.11) | 1907.5 | (1459-2439) | 26.30 |
| | 2% MBCD | 5 | 4185 (3771.23) | 2861 | (1167-10428) | 90.11 |
| | 4% MBCD | 5 | 2885 (1157.06) | 3041 | (1272-4264) | 40.11 |
| | 1% MBCD | 5 | 4527.8 (4167.31) | 3133 | (2003-11880) | 92.04 |
| | 0% MBCD-0.2% ETOH | 5 | 3078.6 (1759.24) | 3558 | (1072-5351) | 57.14 |
| | 1% MBCD-0.1% CMCLV | 5 | 4508.8 (3495.99) | 3374 | (1848-10416) | 77.54 |
| Tmax (min) | IM | 5 | 6 (2.24) | 5 | (5-10) | 37.27 |
| | 1% MBCD | 5 | 30 (0) | 30 | (30-30) | 0.00 |
| | 1% MBCD-Sorbitol | 4 | 52.5 (46.64) | 37.5 | (15-120) | 88.83 |
| | 2% MBCD | 5 | 47 (42.66) | 30 | (10-120) | 90.77 |
| | 4% MBCD | 5 | 25 (15.41) | 30 | (5-45) | 61.64 |
| | 1% MBCD | 5 | 36 (8.22) | 30 | (30-45) | 22.82 |
| | 0% MBCD-0.2% ETOH | 5 | 30 (0) | 30 | (30-30) | 0.00 |
| | 1% MBCD-0.1% CMCLV | 5 | 33 (6.71) | 30 | (30-45) | 20.33 |
| Log $AUC_{last}$ | IM | 5 | 11.8 (0.13) | 11.8 | (11.7-12) | 1.14 |
| | 1% MBCD | 5 | 11.7 (0.45) | 11.5 | (11.4-12.5) | 3.87 |
| | 1% MBCD-Sorbitol | 4 | 11.8 (0.7) | 11.6 | (11.2-12.7) | 5.97 |
| | 2% MBCD | 5 | 12.1 (0.65) | 12.4 | (11.3-12.7) | 5.35 |
| | 4% MBCD | 5 | 11.9 (0.61) | 12.2 | (10.9-12.4) | 5.12 |
| | 1% MBCD | 5 | 11.8 (0.42) | 11.9 | (11.3-12.2) | 3.54 |
| | 0% MBCD-0.2% ETOH | 5 | 11.6 (0.74) | 11.9 | (10.6-12.3) | 6.34 |
| | 1% MBCD-0.1% CMCLV | 5 | 12.1 (0.89) | 12.2 | (11.1-13.5) | 7.31 |
| Log Cmax | IM | 5 | 8.2 (0.33) | 8.2 | (7.7-8.6) | 4.10 |
| | 1% MBCD | 5 | 7.7 (0.75) | 7.3 | (7.2-8.9) | 9.74 |
| | 1% MBCD-Sorbitol | 4 | 7.5 (0.27) | 7.5 | (7.3-7.8) | 3.54 |
| | 2% MBCD | 5 | 8 (0.87) | 8 | (7.1-9.3) | 10.89 |
| | 4% MBCD | 5 | 7.9 (0.47) | 8 | (7.1-8.4) | 5.99 |
| | 1% MBCD | 5 | 8.2 (0.73) | 8 | (7.6-9.4) | 8.89 |
| | 0% MBCD-0.2% ETOH | 5 | 7.9 (0.68) | 8.2 | (7-8.6) | 8.60 |
| | 1% MBCD-0.1% CMCLV | 5 | 8.2 (0.69) | 8.1 | (7.5-9.3) | 8.44 |
| Cl (mL/min) | IM | 5 | 21.4 (2.75) | 21.6 | (17.3-24.7) | 12.87 |
| | 1% MBCD | 5 | 496.3 (164.29) | 541.6 | (219.5-645.2) | 33.10 |
| | 1% MBCD-Sorbitol | 3 | 650.4 (213.33) | 758.2 | (404.7-788.3) | 32.80 |
| | 2% MBCD | 4 | 241.3 (209.12) | 170 | (77.3-547.6) | 86.68 |
| | 4% MBCD | 5 | 456.4 (353.04) | 296.3 | (227.5-1063.2) | 77.35 |

TABLE 8-continued

PK Results Summary for Carbetocin in Rabbits

| Parameter | Formulation ID | No. Obs | Mean (STD) | Median | Range | CV (%) |
|---|---|---|---|---|---|---|
| | 1% MBCD | 5 | 449.8 (189.37) | 384.1 | (276.1-702) | 42.10 |
| | 0% MBCD-0.2% ETOH | 5 | 642.2 (472.78) | 396 | (268.3-1361.2) | 73.62 |
| | 1% MBCD-0.1% CMCLV | 5 | 401.7 (301.59) | 307.5 | (84.1-875.1) | 75.07 |
| $T_{1/2}$ (min) | IM | 5 | 44.3 (17.05) | 48.1 | (16.1-62.5) | 38.46 |
| | 1% MBCD | 5 | 33.6 (13.41) | 32.2 | (18.3-47.4) | 39.90 |
| | 1% MBCD-Sorbitol | 3 | 27.3 (11.93) | 24.7 | (16.9-40.3) | 43.66 |
| | 2% MBCD | 4 | 151.8 (253.49) | 28.4 | (18.5-531.8) | 167.02 |
| | 4% MBCD | 5 | 37.1 (22.54) | 34.8 | (9-61.9) | 60.74 |
| | 1% MBCD | 5 | 44.8 (14.66) | 46.1 | (22.3-59.4) | 32.75 |
| | 0% MBCD-0.2% ETOH | 5 | 23.9 (13.73) | 15.4 | (13.4-45.1) | 57.44 |
| | 1% MBCD-0.1% CMCLV | 5 | 39 (18.67) | 37.2 | (16.1-64.9) | 47.85 |
| Kel (l/min) | IM | 5 | 0.02 (0.013) | 0.0144 | (0.011-0.043) | 67.77 |
| | 1% MBCD | 5 | 0.024 (0.01) | 0.0215 | (0.015-0.038) | 42.53 |
| | 1% MBCD-Sorbitol | 3 | 0.029 (0.012) | 0.028 | (0.017-0.041) | 41.51 |
| | 2% MBCD | 4 | 0.023 (0.017) | 0.0272 | (0.001-0.037) | 72.97 |
| | 4% MBCD | 5 | 0.03 (0.027) | 0.0199 | (0.011-0.077) | 90.15 |
| | 1% MBCD | 5 | 0.017 (0.008) | 0.015 | (0.012-0.031) | 45.28 |
| | 0% MBCD-0.2% ETOH | 5 | 0.036 (0.016) | 0.045 | (0.015-0.052) | 44.52 |
| | 1% MBCD-0.1% CMCLV | 5 | 0.022 (0.013) | 0.0186 | (0.011-0.043) | 57.18 |

TABLE 9

Percent Bioavailability for Carbetocin in Rabbits

| Formulation | Dose (μg/kg) | % Bioavailability |
|---|---|---|
| 1% MBCD | 60 | 4.83 |
| 1% MBCD-Sorbitol | 60 | 5.62 |
| 2% MBCD | 60 | 7.82 |
| 4% MBCD | 60 | 6.14 |
| 1% MBCD | 60 | 5.31 |
| 0% MBCD-0.2% ETOH | 60 | 4.84 |
| 1% MBCD-0.1% CMCLV | 60 | 9.40 |

These results show a carbetocin bioavailabily of about 4 to about 9% was achieved by the intranasal pharmaceutical formulations of this disclosure.

In this second rabbit PK study, the results (i.e., $T_{max}$, $C_{max}$, $AUC_{last}$ and % Bioavailability) obtained from measurements of mean blood levels from rabbits administered formulations modulating the concentration of Me-β-CD concentration are also shown in Table 10, including results concerning the effect of tonicifier, modulating osmolality, and results of new formulations.

TABLE 10

Pharmacokinetic Study 2 Results

| # | Formation | Dose (μg/kg) | Tmax (min) | % CV | Cmax (pg/ML) | % CV | $AUC_{last}$ (min * pg/mL) | % CV | BA % |
|---|---|---|---|---|---|---|---|---|---|
| 1 | IM dose | 3 | 6 | 37 | 3630 | 33 | 138300 | 14 | |
| 2 | 10 Me-β-CD | 60 | 30 | 0 | 2950 | 91 | 133600 | 57 | 4.8 |
| 3 | 10 Me-β-CD, sorbitol | 60 | 53 | 89 | 1930 | 26 | 155500 | 77 | 5.6 |
| 4 | 20 Me-β-CD | 60 | 47 | 91 | 4190 | 90 | 216300 | 54 | 7.8 |
| 5 | 40 Me-β-CD | 60 | 25 | 62 | 2890 | 40 | 169800 | 46 | 6.1 |
| 6 | 10 Me-β-CD, hi osm | 60 | 36 | 23 | 4530 | 92 | 146900 | 39 | 5.3 |
| 7 | EDTA + EtOH | 60 | 30 | 0 | 3080 | 57 | 133900 | 59 | 4.8 |
| 8 | 10 Me-β-CD + CMC + PG | 60 | 33 | 20 | 4510 | 78 | 260000 | 98 | 9.4 |

The data presented in Table 10 indicate that there does not appear a significant effect on BA when the concentration of Me-β-CD is varied, and that there does not appear to be a significant effect on BA when the tonicifier (NaCl or sorbitol) is varied, and that there is a slight increase in BA when increasing osmolality, and that there is no significant increase in BA when using these new formulations; as one rabbit within the CMC plus PG group may be considered as an outlier.

In more detail, the clinical control ("10 Me-β-CD"), and "10 Me-β-CD, sorbitol" were repeated and the data showed that each produced similar carbetocin exposure levels to those observed in the first PK study. The "10 Me-β-CD" clinical formulation produced a 4.8% relative BA (compared to 4.6% in the first PK study), while "10 Me-β-CD, sorbitol" decreased the $C_{max}$ relative to "10 Me-β-CD." Though the $AUC_{last}$ value for "10 Me-β-CD, sorbitol" (155500 min*pg/mL) is slightly higher than that for the "10 Me-β-CD" (133600 min*pg/mL), this outcome is largely due to a lone data point (from a single animal at 120 min in the former dose group). An initial analysis of the PK data suggested that the best performing formulations were "10 Me-β-CD+CMC+PG" (9.4% relative BA) and "20 Me-β-CD" (7.8% relative BA). Due to elevated values at 30 and 240 min, the individual animal data for the formulation containing 20 Me-β-CD were analyzed. These values were found to be a result of one animal as a high responder at 30 min and another animal as a high responder at 240 min time point. Additionally, when the individual results for the "10 Me-β-CD+CMC+PG" were analyzed, the increased exposure was attributed to one high responder animal. When the results for the "10 Me-β-CD+CMC+PG" formulation were re-calculated after removing the one animal, the relative BA decreased from an initial value of 9.4% to 5.4%, which is comparable to other formulations.

The data also showed similar trending consistent with the first PK study with increasing Me-β-CD from low (10 mg/ml) to high level (40 mg/ml) giving increased relative BA (4.8 and 6.1% respectively), $AUC_{last}$ (133600 and 169800 min*pg/mL, respectively), and $C_{ma}$, (2950, 4190, 2890 pg/ml, respectively). However, the mid level dose (20 mg/ml) provided the highest levels for relative BA (7.8%), $AUC_{last}$ (216200 min*pg/ml), and $C_{max}$ (4190 pg/ml). Even with this increase, all results were shown to be statistically similar. Increasing the osmolality of the formulation slightly increased relative BA (5.3 vs. 4.8%), $AUC_{last}$ (133600 vs. 146900 min*pg/mL), and $C_{max}$ (2950 vs. 4530 pg/ml). This result was in contrast to the trend observed for in vitro permeation as a function of formulation osmolality. The "EDTA+EtOH" formulation produced a carbetocin exposure similar to that of "10 mg/mL Me-β-CD" (4.8% rel BA).

Statistical analysis of the in vivo data showed that all formulations were statistically no different from the IM control for $AUC_{last}$ and $C_{max}$ $AUC_{last}$ and $C_{max}$. For example, the P-value for $AUC_{last}$ from groups 2, 3 6 and 7 were 1.0000, 0.8408 for Group 4, 0.9985 for Group 5 and 0.4516 for Group 8. Similarly, the P-value for $C_{max}$ for Group 2 was 0.9989, Group 3 was 0.8914, Group 4 was 0.9997, Group 5 was 0.9981, Group 6 was 0.9939, Group 7 was 0.9997 and Group 8 was 0.9946.

The data from this second in vivo PK study, summarized in Table 10, and in vitro permeation study disclosed in this Example 3, were examined for the possibility of an in vitro-in vivo correlation (IVIVC). A slight correlation may be suggested when comparing both in vivo bioavailability and $AUC_{last}$ with carbetocin permeation in vitro ($R^2$=0.4939 and 0.4973, respectively). A poor IVIVC was observed between in vivo $C_{max}$ and in vitro permeation of carbetocin ($R^2$=0.1185). The lack of correlation between any of the in vivo parameters with in vitro permeation suggests the permeation observed in vitro was not completely predictive of the exposure observed in vivo in rabbits.

IM and IN administration of all test article formulations was well tolerated in rabbits. No adverse clinical signs were observed following IM administration (Group 1) or the IN administrations (Groups 2-8). Observations of the injection site taken at 5 minutes and 1 hour post-intramuscular dose were normal for all animals in Group 1. Nasal observations taken at 5 minutes and 1 hour post-intranasal dose were normal for all rabbits in Groups 2-8; nasal irritation and/or precipitation of the respective formulation was not observed in the nare of any rabbit.

When taken together, as disclosed in this study, it is noted that we did not observe a significant correlation between in vitro results and in vivo results. In this study, our in vitro studies with carbetocin were not predictive of results obtained in vivo.

Example 4

Anxiolytic Effect of Carbetocin and Oxytocin in Rats

The anxiolytic effect of carbetocin and oxytocin was tested using the elevated plus-maze assay in rats as described in Holmes, A., et al., *Behav. Neurosci.* 115(5):1129-44, 2001. See also Sahuque, L., et al., *Psychopharmacology* 186(1): 122-132, Berl, 2006; Carvalho, M. C., et al., *Braz. Med. Biol. Res.* 38(12):1857-66, 2005; and Langen, B., et al., *J. Pharmacol. Exp. Ther.* 314:717-724, 2005. Alprazolam, a known anxiety drug, was also included in the study. Sixty male, 6-10 week old experimentally naïve rats obtained from the Charles River laboratories were divided into six groups of ten animals each. All animals were maintained in compliance with the standards of the National Research Council and were fed certified rodent diet (Teklad, Madison, Wis.) and water ad libitum. The animals were housed in a dedicated study room with 12 hour light/12 hour dark at RT 18 to 26° C. and 30-70% humidity. Study animals were acclimated to their housing for at least 5 days prior to the first day of dosing. Routes of administration included intracerebroventricular (ICV), intraperitoneal (IP), or intramuscular (IM).

For the anxiolytic study, all groups were dosed by injection with formulations that contained the appropriate API in 0.9% saline solution. Alprazolam was an oral solution dosage form and diluted to the desired concentration in 0.9% saline for the anxiolytic study, Alprazolam Intensol™ Oral Solution (Concentrate) 1 mg/ml (each ml contains 1 mg Alprazolam). The Alprazolam was alcohol free and contained the following inactive ingredients: propylene glycol, succinic acid, succinic acid disodium salt and water. The animal treatment groups with the API and its concentration in formulation are shown in Table 11.

TABLE 11

Group Assignments and Dose Levels

| Group | Route | Treatment API | Dose (mg/kg) | Volume (mL/kg) | Conc. (mg/ml) |
|---|---|---|---|---|---|
| 1 | ICV | Vehicle | 0 | 0.03 | 0 |
| 2 | IP | Alprazolam | 0.5 | 5 | 0.1 |
| 3 | ICV | Oxytocin | 0.05 | 0.03 | 1.7 |
| 4 | IM | Oxytocin | 1.0 | 0.2 | 5 |
| 5 | ICV | Carbetocin | 0.25 | 0.03 | 8.3 |
| 6 | IM | Carbetocin | 5 | 0.2 | 25 |

The dosing preparations were administered once to each rat as a bolus. In the ICV administration group, test doses were administered into the lateral ventricle through a port in the already implanted ICV cannula. Testing was conducted 20 minutes after ICV and 30 minutes after IM and IP. The animals were tested for 15 minutes on the maze immediately following transport from the home cage.

The elevated plus maze consisted of a platform with 4 arms, two open and two closed (50×10×50 cm enclosed with an open roof). Rats were tested two at a time and placed by hand in the center of the platform of two separate mazes, at the crossroad of the 4 arms, facing one of the open arms. After fifteen minutes, the first rat was left for a few seconds until the second rat's fifteen minutes was completed. The rats were monitored remotely.

Prior to each rat's test, the plus-maze surfaces and closed sides were cleaned. Rats were handled by gloved hands. The time from removal from the home cage to start of testing was less than 15 seconds. Rats were gently removed from the home cage and placed onto the center square between the open and closed arms, and facing the opposite open arm. The rats were facing away from the experimenter. The experimenter moved away from the maze to an area not visible to the rat(s) and viewed the rat(s) via television monitor. At the end of the test the recorder was stopped and the rat(s) removed from the maze.

Time spent in the open arm suggested low anxiety while time spent in the closed arm suggested higher anxiety. The rats were evaluated for time spent in open arm exploration (Open Time), time spent in closed arm exploration (Closed Time) and scored for anxiety according to the percent of time spent in open arm exploration ([time spent in open arms/time spent in open arms+time spent in closed arms×100]) (Open Time %); the absolute time spent in open arm exploration; and the percent of open arm entries ([number of open arm entries/number of open arm entries+number of closed arm entries]× 100). The number of total arm entries was used as a measure of overall locomotor activity. The scores were compared to the vehicle controls and to the baseline using one-way ANOVA followed by the appropriate post-hoc test (Bonferroni/Dunnets) and a $p<0.05$ was considered to be statistically significant. The results of the anxiolytic study are shown in Table 12.

TABLE 12

Anxiolytic Study Maze Time Results

| Group | Route | Treatment | Open Time | Closed Time | Open Time (%) | SD |
|---|---|---|---|---|---|---|
| 1 | ICV | Vehicle | 38.78 | 124.41 | 24 | 13.5 |
| 2 | IP | Alprazolam | 46.07 | 116.55 | 27.9 | 25 |
| 3 | ICV | Oxytocin | 17.89 | 158.42 | 11.3 | 31 |
| 4 | IM | Oxytocin | 14.54 | 159.47 | 8.6 | 11.1 |
| 5 | ICV | Carbetocin | 64.68 | 113.49 | 36 | 36.6 |
| 6 | IM | Carbetocin | 34.31 | 117.57 | 23.6 | 14.3 |

The results for the time spent in open arm exploration (Open Time) and percent time spent in open arm exploration (Open Time %) showed that ICV administration of carbetocin reduced anxiety in rats compared to oxytocin using the elevated plus-maze assay.

Example 5

Manufacture of Carbetocin Nasal Spray

Carbetocin Nasal Spray was prepared by adding the following ingredients (in order) to sterile water for irrigation or purified water: L-arginine hydrochloride, edetate disodium (EDTA), methyl-β-cyclodextrin (M-β-CD), sodium chloride (NaCl), and chlorobutanol (CB). Each ingredient was stirred until visual confirmation of dissolution was achieved. All ingredients except M-β-CD and CB achieved dissolution within 10 min or less. Once all ingredients were dissolved, the pH was adjusted to 4.0±0.3 with sodium hydroxide or hydrochloric acid, if necessary. The solution was brought to volume (target weight) with sterile water for irrigation or purified water to produce "diluent" for the Carbetocin Nasal Spray. An appropriate amount of carbetocin was then dissolved in ~85% of the diluent, brought to volume (target weight) with diluent to produce Carbetocin Nasal Spray, and the pH was adjusted with sodium hydroxide or hydrochloric acid, if necessary.

A description of possible packaging components for the Carbetocin Nasal Spray is shown in Table 13.

TABLE 13

Packaging Components for Carbetocin Nasal Spray

| Component | Supplier |
|---|---|
| Clear 3-cc Type I glass bottle | SGD |
| White Polypropylene Cap. Fine-RIB with A 0.040 Tri foil ® WP217 liner | O'Berk |
| Nasal spray pump w/safety clip, 0.1 mL delivery volume Lot: 2085N-01390-3 | Pfieffer |

Carbetocin Nasal Spray was stored at 5° C. The shelf life for the Carbetocin Nasal Spray was at least 9 months at 5° C. and projected to be stable for more than 2 years at 5° C. and 25° C.

Example 6

Carbetocin Nasal Spray Stability

Carbetocin IN Formulation Stability

A stability study was performed to identify stable carbetocin formulations that had already shown enhanced carbetocin permeation. All formulations contained a final concentration of 10 mg/ml carbetocin. The formulations tested are shown in Table 14.

TABLE 14

Formulations Tested in Stability Study

| # | Carbetocin (mg/ml) | Me-β-CD (mg/ml) | EDTA (mg/ml) | DDPC (mg/ml) | NaCl (mM) | Sorbitol (mM) | Arginine (mM) | Chlorobutanol (mg/ml) | pH |
|---|---|---|---|---|---|---|---|---|---|
| 1 | 10 | 40 | 5 | 0 | 40 | 0 | 10 | 5 | 4.5 |
| 2 | 10 | 0 | 2.5 | 0 | 0 | 131 | 0 | 5 | 4 |
| 3 | 10 | 30 | 2 | 1 | 70 | 0 | 10 | 0 | 4 |

At temperatures 5° C., 25° C. and 40° C. and 1 day, 4 day, 2 week, 1 month, 2 month, 3 month, and 6 month timepoints, the following data was collected: appearance, pH, osmolality, peptide content, purity, and chlorobutanol content.

Summary of Results:

At 5° C.: appearance, pH, osmolality, peptide content, purity, and chlorobutanol content did not vary significantly at refrigerated conditions. All samples remained clear. Total peptide impurities were 1.0-1.1% at t=0 and 1.1-1.3% at t=6 months.

At 25° C.: appearance, pH, osmolality, peptide content and chlorobutanol content did not vary significantly at 25° C. A slight increase in total peptide impurities, up to 1.9%, was observed for pH 4.5 formulation (No. 1) and 2.9-3.0% for pH 4.0 formulations (Nos. 2, 3).

At 40° C.: all formulations remained clear. Formulation #1 at pH 4.5 maintained pH, peptide content and chlorobutanol content. Osmolality increased ~10% from 183 to 202 mOsm/kg H2O. Formulation No. 1 total peptide impurities increased the least of all samples to 5.7% at t=6 months, and chlorobutanol content and peptide content did not change significantly. Formulation #2 at pH 4.0 showed the largest change, with a pH drift of approximately −0.4 pH units (pH 4.0 to 3.6), an increase in osmolality of approximately 20% (197 to 239 mOsm/kg H2O), and an increase in total peptide impurities to 17.5%. Formulation No. 3, also at pH 4.0, showed some change with a slight drift in pH from pH 4.1 to 4.2, a 26% increase in osmolality (204 to 257 mOsm/kg H2O), and an increase in total peptide related impurities to 10.3%, and peptide content appeared unchanged while chlorobutanol content decreased slightly.

Formulation No. 1 had the least total peptide impurities at 25° C. and 40° C. for all time points. Projections based on 25° C. data suggest that Formulation No. 1 at pH 4.5 could have a shelf life of >4 years (assuming 10% total impurities) and Formulation Nos. 2 and 3 at pH 4.0 could have a shelf life of >2 years at room temperature conditions.

Preservative-containing Carbetocin IN Formulation Stability

A further stability study was performed to monitor stability of preservative-containing formulations. The base formulations (without preservative) are listed in Table 15. All formulations contained 3 mg/ml carbetocin.

TABLE 15

Base Formulations for Preservative Stability Study

| Group# | Me-β-CD (mg/ml) | EDTA (mg/ml) | Arginine (mM) | pH | Tonicifier |
|---|---|---|---|---|---|
| 1 | 0 | 3.5 | 10 | 4.0 | NaCl |
| 2 | 10 | 3.5 | 10 | 4.0 | NaCl |
| 3 | 10 | 3.5 | 10 | 4.0 | Sorbitol |
| 4 | 20 | 3.5 | 10 | 4.0 | NaCl |

Each formulation was prepared with the following different preservative systems: Methylparaben/Propylparaben (MP/PP), chlorobutanol (CB), and benzyl alcohol (BA) alone and in combination. The tested preservative levels are shown in Table 16:

TABLE 16

Preservative Levels and Combinations

| Preservative | Final Conc. In Formulation | Groups to be Tested |
|---|---|---|
| MP/PP 1 | 0.33 mg/mL MP/0.17 mg/mL PP | 1, 2, 3, 4 |
| CB 1 | 2.5 mg/mL | 1, 2, 3, 4 |
| CB 2 | 5 mg/mL | 1, 2, 3, 4 |
| MP/PP 1 + CB 2 | 0.33 mg/mL MP, 0.17 mg/mL PP, 5 mg/mL CB | 1, 2, 3, 4 |
| MP/PP 2 + BA | 2 mg/mL MP, 2 mg/mL PP, 5 mg/mL BA | 1, 4 |

Accordingly, a total of 18 active formulations and their placebos were prepared. The resulting formulations containing preservatives are shown in Table 17. The formulations that contained 5 mg/ml chlorobutanol only as preservative are marked with an asterisk.

TABLE 17

Preservative-containing Formulations for Stability Study

| # | Group # | Me-β-CD (mg/ml) | EDTA (mg/Ml) | Arg (mM) | pH | MP (mg/ml) | PP (mg/ml) | CB (mg/ml) | BA (mg/ml) | Sorbitol (mM) | NaCl (mM) |
|---|---|---|---|---|---|---|---|---|---|---|---|
| 1 | 1 | 0 | 3.5 | 10 | 4.0 | 0.3 | 0.17 | 0 | 0 | 0 | 70.0 |
| 2 | 1 | 0 | 3.5 | 10 | 4.0 | 0 | 0 | 2.5 | 0 | 0 | 65.0 |
| 3* | 1 | 0 | 3.5 | 10 | 4.0 | 0 | 0 | 5.0 | 0 | 0 | 57.0 |
| 4 | 1 | 0 | 3.5 | 10 | 4.0 | 0.3 | 0.17 | 5.0 | 0 | 0 | 55.0 |
| 5 | 1 | 0 | 3.5 | 10 | 4.0 | 2.0 | 2.00 | 0 | 5.0 | 0 | 25.0 |
| 6 | 2 | 10 | 3.5 | 10 | 4.0 | 0.3 | 0.17 | 0 | 0 | 0 | 65.0 |
| 7 | 2 | 10 | 3.5 | 10 | 4.0 | 0 | 0 | 2.5 | 0 | 0 | 60.0 |
| 8* | 2 | 10 | 3.5 | 10 | 4.0 | 0 | 0 | 5.0 | 0 | 0 | 52.0 |
| 9 | 2 | 10 | 3.5 | 10 | 4.0 | 0.3 | 0.17 | 5.0 | 0 | 0 | 50.0 |
| 10 | 3 | 10 | 3.5 | 10 | 4.0 | 0.3 | 0.17 | 0 | 0 | 130.0 | 0 |
| 11 | 3 | 10 | 3.5 | 10 | 4.0 | 0 | 0 | 2.5 | 0 | 120.0 | 0 |
| 12* | 3 | 10 | 3.5 | 10 | 4.0 | 0 | 0 | 5.0 | 0 | 104.0 | 0 |
| 13 | 3 | 10 | 3.5 | 10 | 4.0 | 0.3 | 0.17 | 5.0 | 0 | 100.0 | 0 |
| 14 | 4 | 20 | 3.5 | 10 | 4.0 | 0.3 | 0.17 | 0 | 0 | 0 | 60.0 |
| 15 | 4 | 20 | 3.5 | 10 | 4.0 | 0 | 0 | 2.5 | 0 | 0 | 55.0 |
| 16* | 4 | 20 | 3.5 | 10 | 4.0 | 0 | 0 | 5.0 | 0 | 0 | 50.0 |
| 17 | 4 | 20 | 3.5 | 10 | 4.0 | 0.3 | 0.17 | 5.0 | 0 | 0 | 47.0 |
| 18 | 4 | 20 | 3.5 | 10 | 4.0 | 2.0 | 2.00 | 0 | 5.0 | 0 | 20.0 |

The following data was collected at temperatures 5° C., 25° C. and 40° C. and time points 0 day, 2 week, 1 month, 1.5 month, 2 month, 3 month, and 6 month: appearance, pH, osmolality, peptide content and purity.

Summary of Results:

At 5° C.: all formulations remained clear with one exception. Formulation No. 18 (with MP/PP/BA) contained precipitate at t=3 and 6 months. All formulations maintained pH, osmolality, peptide content and purity to t=6 months. Total impurities at t=6 months were 1.2% to 1.3%.

At 25° C.: all formulations remained clear with one exception. Formulation No. 18 (with MP/PP/BA) contained precipitate at t=3 and 6 months. All formulations maintained pH, osmolality, and peptide content to t=6 months. Total impurities increased slightly to 3.1-3.9% at t=6 months.

At 40° C.: all formulations remained clear. Several of the formulations were beginning to show a pH drift of −0.1 pH units at t=2 months with the exception of formulations containing 2.5 mg/ml CB or the formulations containing 20 mg/mL Me-β-CD. Osmolality did not increase significantly. Peptide content decreased slightly for several formulations at t=2 months (96.2-103.1% peptide content). Total peptide related impurities increased to 5.0-7.2%, similar to formulations at pH 4.0 above (Table 12).

Based on 40° C. data, formulations with the MP/PP preservative system appear to have the best stability while formulations with 5 mg/mL CB and the combination of MP/PP/CB had the poorest stability. Still, the IN formulations with the lowest stability in this study should have a shelf life at 5° C. of >2 years and at room temperature of ≥1.5 years, based on data collected.

Buffer and pH Range Carbetocin IN Formulation Stability

A further stability study was performed to monitor stability of carbetocin formulations across the pH range of 3-10. All formulations contained 2 mg/ml carbetocin in 10 mM buffer in isotonic NaCl. The formulations tested are shown in Table 18. The following data was collected at temperatures 25° C., 40° C. and 50° C. and time points 0 day, 2 week, 1 month, 1.5 month, 2 month, and 3 month: pH, osmolality, appearance, carbetocin content and purity (by HPLC).

TABLE 18

Formulations Tested in pH Stability Study

| # | Formulation pH | Buffer | Buffer pK$_a$ |
|---|---|---|---|
| 1 | 3.0 | citrate | 3.12 (pK$_1$) |
| 2 | 3.0 | tartrate | 2.96 (pK$_1$) |
| 3 | 3.5 | citrate | 3.12 (pK$_1$) |
| 4 | 3.5 | tartrate | 2.96 (pK$_1$) |
| 5 | 4.0 | acetate | 4.74 |
| 6 | 4.0 | citrate | 4.76 (pK$_2$) |
| 7 | 4.5 | acetate | 4.74 |
| 8 | 4.5 | citrate | 4.76 (pK$_2$) |
| 9 | 5.0 | acetate | 4.74 |
| 10 | 5.0 | citrate | 4.76 (pK$_2$) |
| 11 | 6.0 | citrate | 6.40 (pK$_3$) |
| 12 | 6.0 | phosphate | 7.10 (pK$_2$) |
| 13 | 7.0 | citrate | 6.40 (pK$_3$) |
| 14 | 7.0 | phosphate | 7.10 (pK$_2$) |
| 15 | 8.0 | phosphate | 7.10 (pK$_2$) |
| 16 | 9.0 | arginine | 9.09 (pK$_2$) |
| 17 | 10.0 | arginine | 9.09 (pK$_2$) |

Summary of Results:

At 25° C.: all formulations remained clear and maintained pH and osmolality for all time points. Total peptide-related impurities increased at either extremes of the pH range. The best peptide purity was maintained across pH 4.5 to 6.0 (1.1 to 1.4% total peptide related impurities at t=3 months). At pH 4.0, peptide purity increased to 2.2% at t=3 months. Peptide content followed a similar trend. The buffer type also contributed to peptide stability; the fewer ionizable sites on the buffer, the better the stability of carbetocin (i.e., stability trended as follows: acetate>tartrate>citrate>phosphate).

A 40° C.: all formulations remained clear. Formulations below pH 7 maintained pH well, while formulations above pH 7 showed significant drift (>0.2 pH units) at t=1 months. Osmolality was maintained over the time points tested. The best peptide purity was maintained at pH 5.0 (1.9-2.1% total peptide-related impurities at t=3 months). Similar trends as those seen at 25° C. regarding pH effect and buffer effect on peptide purity were observed at 40° C.

At 50° C.: all formulations remained clear. Formulations below pH 7 maintained pH well, while formulations above pH 7 showed significant drift (>0.2 pH units) at t=1 month. Osmolality was maintained over the time points tested. The best peptide purity was maintained at pH 5.0 (2.9-3.1% total peptide-related impurities at t=1.5 months). The trends seen at 25° C. regarding pH effect and buffer effect on peptide purity were similar to those observed at 40° C.

Figure 2:
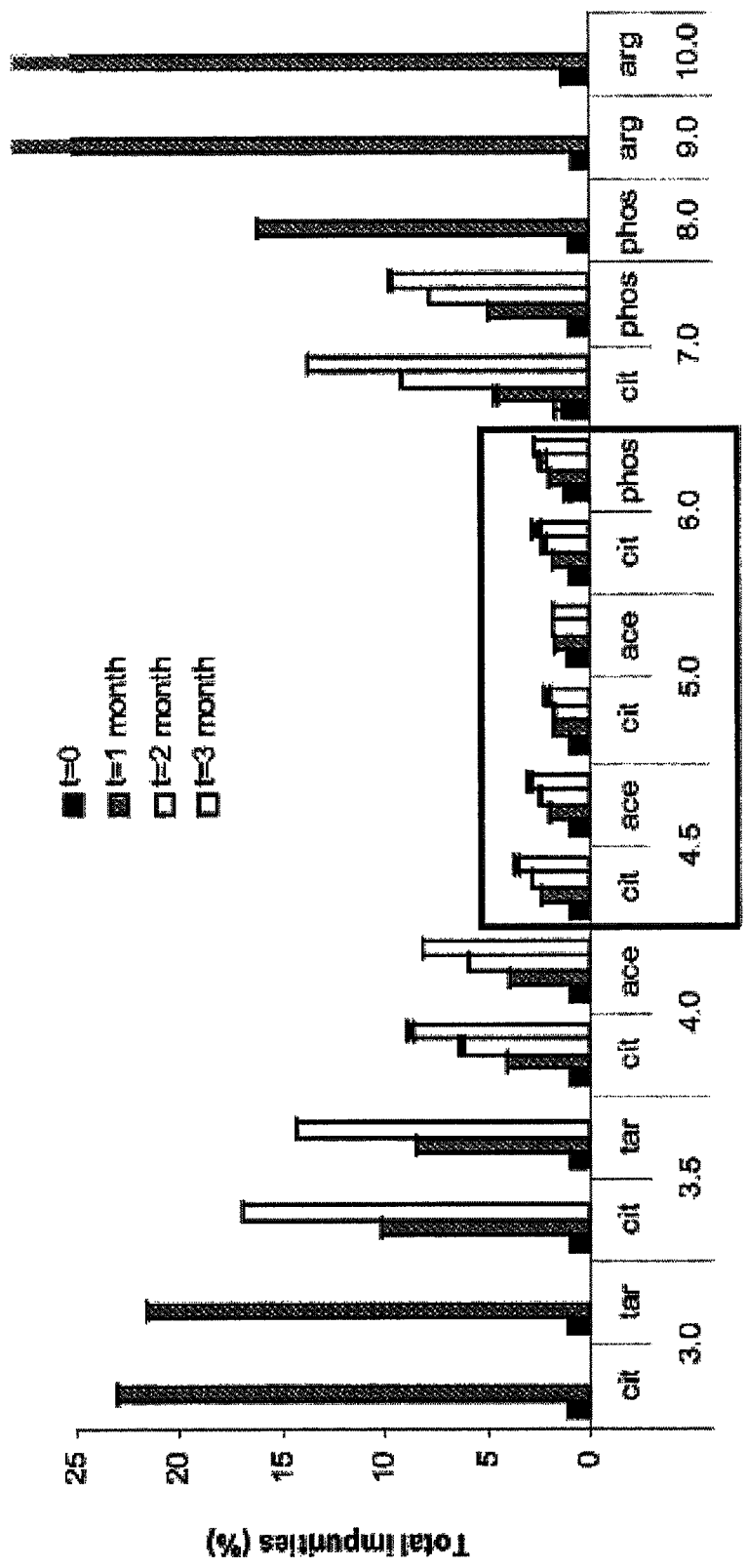
FIG. 2: A bar graph representing the total peptide related impurities for Carbetocin Nasal Spray formulations in different buffers (citrate, tartrate, acetate, phosphate, and arginine) and at different pH, ranging from 3.0 to 10.0, over time at 50° C.

FIG. 2 shows the total peptide related impurities for the pH stability study. The best peptide purity was maintained across pH 4.5 to 6.0. Peptide content followed a similar trend. The buffer type also contributed to peptide stability: the fewer ionizable sites on the buffer, the better the stability of carbetocin (stability trended as follows: stability in acetate>stability in tartrate>stability in citrate>stability in phosphate).

Duratocin® Stability

Duratocin® was stored in 1 ml ampoules (as sold) at 5° C., 25° C., and 40° C. The following data was collected at 0 day, 2 month, 3 month, 6 month, 12 month, and 24 month timepoints: pH, osmolality, appearance, and peptide content and purity (by HPLC).

At 25 and 40° C., the pH observed in Duratocin® has remained constant for up to 6 months (pH 4.2 at t=0, pH 4.2 at t=6 months at 25° C.). Stability has been observed up to 1 year; formulation pH has varied only slightly (pH 4.2 at t=0, pH 4.4 at t=12 months at 25° C.) and remains unchanged at 5° C. Osmolality and appearance were not changed up to 12 months. Total peptide-related impurities increased slightly from 1.2% initially to 2.5% at 25° C. and 4.6% at 40° C. at t=6 months, and to 3.4% at 25° C. and 4.6% at 40° C. at 12 months. Total impurities remain unchanged at 5° C., up to 12 months.

Carbetocin IN Formulation Stability

Stability of IN carbetocin formulations shown in Table 19 were tested for appearance, osmolality, peptide content, purity, and chlorobutanol content at 5° C., 25° C., and 40° C. and at 1 month, 2 month, 3 month and 6 month time points. All groups contained 10 mM Arginine. Groups 2-8 contain 5 mg/mL chlorobutanol. Group 8 contained CMC LV=carboxymethylcellulose sodium (low viscosity, 10-50 cps) and PG=propylene glycol.

TABLE 19

Formulations for IN Carbetocin Stability Study

| # | Carbetocin (mg/ml) | Me-β-CD (mg/ml) | EDTA (mg/ml) | CMC LV (mg/mL) | Sorbitol (mM) | NaCl (mM) | EtOH (mg/ml) | PG (mg/ml) | pH |
|---|---|---|---|---|---|---|---|---|---|
| 2 | 4 | 10 | 3.5 | 0 | 0 | 52 | 0 | 0 | 4.0 |
| 3 | 4 | 10 | 3.5 | 0 | 104 | 0 | 0 | 0 | 4.0 |
| 4 | 4 | 20 | 3.5 | 0 | 0 | 50 | 0 | 0 | 4.0 |
| 5 | 4 | 40 | 3.5 | 0 | 0 | 40 | 0 | 0 | 4.0 |
| 6 | 4 | 10 | 3.5 | 0 | 0 | 86 | 0 | 0 | 4.0 |
| 7 | 4 | 0 | 3.75 | 0 | 0 | 50 | 2 | 0 | 4.0 |
| 8 | 4 | 10 | 3.5 | 1.0 | 0 | 0 | 0 | 10 | 4.0 |

Summary of Results:

At 5° C.: all formulations remained clear to date. All formulations maintained pH and osmolality to t=6 months.

At 25° C.: all formulations remained clear to date. All formulations maintained pH and osmolality to t=6 months. Total impurities increased slightly to 2.8-3.3% at t=6 month. All formulations performed similarly.

At 40° C.: all formulations remained clear. Several of the formulations were beginning to show a pH drift off 0.1 pH units at t=3 months. Osmolality was not increased significantly at t=3 months. Peptide content decreased slightly for several formulations at t=2 months (97.4-102.1% peptide content). No decrease in content was detected at t=3 months. Total peptide related impurities increased to 6.8-9.1% at t=3 months, similar to or better than formulations at pH 4.0 from the preservative-containing study (Table 17).

Photostability of Carbetocin IN Formulations

The photostability (i.e., light and energy exposure) of Carbetocin Nasal Spray formulation within both amber and clear glass non-silanized vials was assayed. Samples were subjected to at least 1.2 million lux-hours and an integrated near ultraviolet energy of not less than 200 watt hours/m2 of light intensity on Carbetocin Nasal Spray. Effects of this exposure were determined by the purity-indicating HPLC assay. The formulations tested in the photostability study are shown in Table 20.

TABLE 20

Formulations Tested in Photostability Study

| Group # | Carbetocin (mg/ml) | Me-β-CD (mg/ml) | EDTA (mg/ml) | Arginine (mM) | NaCl (mM) | CB (mg/ml) | pH |
|---|---|---|---|---|---|---|---|
| 1 | 0 | 10 | 3.5 | 10 | 52 | 5 | 4.0 |
| 2 | 1.5 | 10 | 3.5 | 10 | 52 | 5 | 4.0 |
| 3 | 3.0 | 10 | 3.5 | 10 | 52 | 5 | 4.0 |
| 4 | 5.0 | 10 | 3.5 | 10 | 52 | 50 | 4.0 |

The effect of light on the product in the "As-Sold" configuration and in the horizontal (sideways) position was evaluated by the "Sun Test." The exposure of the samples was not less than 1.2 million lux-hours and integrated non-ultraviolet energy of 200 watt-hours/square meter. After exposure to the "I×ICH light" condition, the samples were removed from the sun box and allowed to equilibrate to room temperature conditions prior to testing. For each formulation, 5 sub-samples (A-E) were evaluated as described in Table 21.

TABLE 21

Photostability Sub-sample Groups

| Sub-sample | Description |
|---|---|
| A | 2.0 mL fill in a clear, non-silanized 3-cc vial |
| B | 2.0 mL fill in a clear, non-silanized 3-cc vial, covered in foil |
| C | 2.0 mL fill in a amber, non-silanized 3-cc vial |
| D | 2.0 mL fill in a amber, non-silanized 3-cc vial, covered in foil |
| E | UNTREATED CONTROL (not placed in lightbox) 2.0 mL fill in a clear, non-silanized 2-cc vial, |

Summary of Results:

After exposure to light in the different conditions peptide and chlorobutanol content were unchanged. Total peptide-related impurities were 1.2-1.7% for all samples in post-testing. The untreated control samples (E) had 1.2-1.3% total impurities for all formulations. Samples B, C, D showed no change in total impurities relative to the control (E) for all samples, however, samples A (in clear vials) showed a slight increase in total impurities to 1.5-1.7%.

Clinical Carbetocin Nasal Spray Formulation Stability

Carbetocin Nasal Spray was manufactured as described in Example 5. The configuration for Carbetocin Nasal Spray was a 2 ml fill into 3 cc clear Type-1 U-Save glass bottle with a trifoil-lined polypropylene cap. The product was formulated, filled into bottles and capped, stored at various temperature conditions for various times to study changes in concentration and purity of carbetocin (HPLC), chlorobutanol concentration (HPLC), and formulation pH, appearance, and osmolality. The formulations tested are shown in Table 22. The stability testing schedules for 5° C./ambient RH, 25° C./60% RH, and 40° C./75% RH includes testing at 1 month and 2 months.

TABLE 22

Clinical Carbetocin Nasal Spray Formulations

| Component | #1: | #2: | #3: | #4: Placebo |
|---|---|---|---|---|
| Carbetocin (mg/mL) | 1.5 | 3.0 | 5.0 | 0 |
| Methyl-β-cyclodextrin (Cavasol W7 M Pharma) (mg/mL) | 10 | 10 | 10 | 10 |
| Edetate Disodium, USP (mg/mL) | 3.5 | 3.5 | 3.5 | 3.5 |
| L-Arginine hydrochloride, USP (mM) | 10 | 10 | 10 | 10 |
| Sodium Chloride, USP (mM) | 52 | 52 | 52 | 52 |
| Chlorobutanol (anhydrous), NF (mg/mL) | 5.0 | 5.0 | 5.0 | 5.0 |
| Hydrochloric Acid, 10% diluted, NF (mg/mL) | TAP | TAP | TAP | TAP |
| Sodium Hydroxide, NF (mg/mL) | TAP | TAP | TAP | TAP |
| Nastech Purified Water | qs | qs | qs | qs |
| Target pH | 4.0 | 4.0 | 4.0 | 4.0 |

Summary of Results:

At t=6 months, formulations were performing comparable to or better than similar formulations in the previous preservative-containing stability study (Table 17) and carbetocin IN formulations stability study (Table 19). At 25° C., total impurities range from 2.7-3.4%. At 40° C., total impurities range from 6.4-8.7%. A summary of HPLC data is shown in Table 23.

vitro. The following excipients were varied: CMC LV, CMC MV, EtOH. Sodium chloride concentration was adjusted to keep the osmolality at ~200 mOsm/kg $H_2O$.

Me-β-CD (20 mg/ml), EDTA (3.5 mg/ml), and arginine (10 mM) concentrations were selected based on preliminary permeation results which showed 20 mg/ml Me-β-CD produced slightly improved permeation relative to 10 mg/ml

TABLE 23

Clinical Carbetocin Nasal Spray HPLC Data

| Stability Study # | Nominal [Carbetocin] (mg/mL) | Storage Condition | Storage Period (Months) | Peptide Recovery (%) | Largest Individual Impurity (%) | Total Unknown Impurities (%) | CB Recovery (%) |
|---|---|---|---|---|---|---|---|
| Placebo | 0 | Initial | — | — | — | — | 101.6 |
| #4 | | 25° C. | 6 | — | — | — | 98.7 |
| #1 | 1.5 | Initial | — | 102.3 | 0.3 | 1.3 | 99.7 |
| | | 25° C. | 6 | 101.2 | 1.2 | 3.4 | 97.9 |
| #2 | 3.0 | Initial | — | 103.2 | 0.2 | 1.3 | 99.8 |
| | | 25° C. | 6 | 100.7 | 1.0 | 3.0 | 97.1 |
| #3 | 5.0 | Initial | — | 102.5 | 0.3 | 1.4 | 98.8 |
| | | 25° C. | 6 | 100.2 | 0.8 | 2.7 | 96.7 |
| Current Specifications: | | | | 80.0-120.0 | ≤1.0 | ≤3.5 | 80.0-120.0 |

Example 7

Carbetocin Formulation Enhancing Excipients

Variations in excipient concentrations were tested to determine the effect on carbetocin permeation, MTT, and LDH in vitro.

Me-β-CD when other excipients were held constant. The pH for the DOE formulations was set at pH 4.5 based on stability data which indicated that carbetocin is more stable at pH 4.5 than at pH 4.0. Each formulation contained 4 mg/mL carbetocin and the load volume was 25 uL. The formulations tested in this study are shown in Table 24.

TABLE 24

Carbetocin Formulations

| # | Me-β-CD (mg/ml) | EDTA (mg/ml) | Arg (mM) | CMC LV (mg/ml) | CMC MV (mg/ml) | EtOH (mg/ml) | NaCl (mM) | Sorbitol (mM) | CB (mg/ml) | pH | Comments |
|---|---|---|---|---|---|---|---|---|---|---|---|
| 1 | 20 | 3.5 | 10 | 12.00 | 0 | 2.50 | 40 | 0 | 0 | 4.5 | |
| 2 | 20 | 3.5 | 10 | 10.24 | 0 | 4.27 | 20 | 0 | 0 | 4.5 | |
| 3 | 20 | 3.5 | 10 | 1.76 | 0 | 0.73 | 60 | 0 | 0 | 4.5 | |
| 4 | 20 | 3.5 | 10 | 6.00 | 0 | 0.00 | 70 | 0 | 0 | 4.5 | |
| 5 | 20 | 3.5 | 10 | 1.76 | 0 | 4.27 | 20 | 0 | 0 | 4.5 | |
| 6 | 20 | 3.5 | 10 | 6.00 | 0 | 5.00 | 15 | 0 | 0 | 4.5 | |
| 7 | 20 | 3.5 | 10 | 6.00 | 0 | 2.50 | 40 | 0 | 0 | 4.5 | |
| 8 | 20 | 3.5 | 10 | 0.00 | 0 | 2.50 | 40 | 0 | 0 | 4.5 | |
| 9 | 20 | 3.5 | 10 | 6.00 | 0 | 2.50 | 40 | 0 | 0 | 4.5 | |
| 10 | 20 | 3.5 | 10 | 10.24 | 0 | 0.73 | 60 | 0 | 0 | 4.5 | |
| 11 | 20 | 3.5 | 10 | 0 | 12.00 | 2.50 | 40 | 0 | 0 | 4.5 | |
| 12 | 20 | 3.5 | 10 | 0 | 10.24 | 4.27 | 20 | 0 | 0 | 4.5 | |
| 13 | 20 | 3.5 | 10 | 0 | 1.76 | 0.73 | 60 | 0 | 0 | 4.5 | |
| 14 | 20 | 3.5 | 10 | 0 | 6.00 | 0.00 | 70 | 0 | 0 | 4.5 | |
| 15 | 20 | 3.5 | 10 | 0 | 1.76 | 4.27 | 20 | 0 | 0 | 4.5 | |
| 16 | 20 | 3.5 | 10 | 0 | 6.00 | 5.00 | 15 | 0 | 0 | 4.5 | |
| 17 | 20 | 3.5 | 10 | 0 | 6.00 | 2.50 | 40 | 0 | 0 | 4.5 | |
| 18 | 20 | 3.5 | 10 | 0 | 0.00 | 2.50 | 40 | 0 | 0 | 4.5 | |
| 19 | 20 | 3.5 | 10 | 0 | 6.00 | 2.50 | 40 | 0 | 0 | 4.5 | |
| 20 | 20 | 3.5 | 10 | 0 | 10.24 | 0.73 | 60 | 0 | 0 | 4.5 | |
| 21 | 10 | 3.5 | 10 | 0 | 0 | 0 | 52 | 0 | 5 | 4.0 | Clinical Control |
| 22 | 40 | 5 | 10 | 0 | 0 | 0 | 40 | 0 | 5 | 4.5 | OEF w/CB |
| 23 | 0 | 2.5 | 0 | 0 | 0 | 0 | 0 | 181 | 5 | 4.0 | GRAS w/CB |
| 24 | 0 | 0 | 10 | 0 | 0 | 0 | 150 | 0 | 0 | 7.0 | ctrl no enh |
| 25 | | | | | Media | | | | | | |
| 25 | | | | | Triton X | | | | | | |

Results showed that all test formulations reduced TER (>90%), all formulations achieved >80% MTT, and all formulations achieved <20% percent LDH for both apical and basolateral LDH. The permeation results suggest that EtOH positively effects permeation. Sample #4 (no EtOH) had the lowest permeation (0.73 mg/mL EtOH), approximately 3%. Samples 2, 5, and 6 (all containing >4.0 mg/mL EtOH) showed increased permeation, >8%. No significant difference in permeation results was observed with the addition of CMC-LV.

A second study to determine the effect of variations on excipient concentrations was performed. The following excipients were varied: CMC-MV, HPMC, and EtOH. Sodium chloride concentration was adjusted to keep osmolality ~200 mOsm/kg $H_2O$. CMC-MV and EtOH concentrations were based on a predicted best formulation from the previous study, which predicted 1.8 mg/ml CMC-MV and 3.3 mg/ml EtOH. The central composite DOE was used here, which set the center point for these two excipients at the optimum predicted by the DOE software. For the HPMC and EtOH tests, a slightly wider range of EtOH concentrations were used and HPMC concentrations were based on 3.0 mg/ml as the center point for a central composite design.

Each formulation contained 4 mg/mL carbetocin and the load volume was 25 uL. All samples were tested for LDH, MTT, TER reduction, and carbetocin permeation. The formulations tested are shown in Table 25.

The results showed that all test formulations resulted in TER reduction (>90%). All formulations achieved >80% MTT. Formulations showed % LDH values in a range of from about 4% to about 39% for apical assay. Samples 1-6,9,11-14, 16, 17, 19 had less than 20% LDH. Samples 7, 8, 10, and 15 had ~20% LDH values. Samples 18 and 20 had % LDH values of 33% and 39% respectively. All formulations achieved ~0% LDH for the basolateral sample assay.

Samples 1-20 showed relatively high permeation (>20%) for all tested combinations of EtOH, CMC MV and HPMC. The permeation results are shown in Table 26.

TABLE 26

| Permeation Results | | |
|---|---|---|
| Sample | Avg % permeation | % std deviation |
| 1 | 45.3 | 14.1 |
| 2 | 39.9 | 5.5 |
| 3 | 26.9 | 3.0 |
| 4 | 21.4 | 6.8 |
| 5 | 28.8 | 11.1 |
| 6 | 21.5 | 6.7 |
| 7 | 22.9 | 6.5 |
| 8 | 26.2 | 10.7 |
| 9 | 20.7 | 3.8 |
| 10 | 18.3 | 5.9 |
| 11 | 22.6 | 5.9 |
| 12 | 52.4 | 3.1 |
| 13 | 32.8 | 5.4 |

TABLE 25

Carbetocin Formulations (Second Study)

| # | Me-β-CD (mg/ml) | EDTA (mg/ml) | Arg (mM) | HPMC (mg/ml) | CMC MV (mg/ml) | EtOH (mg/ml) | NaCl (mM) | Sorbitol (mM) | CB (mg/ml) | pH | Comments |
|---|---|---|---|---|---|---|---|---|---|---|---|
| 1 | 20 | 3.5 | 10 | 0.88 | 0 | 6.40 | 40 | 0 | 0 | 4.5 | |
| 2 | 20 | 3.5 | 10 | 6.00 | 0 | 3.75 | 20 | 0 | 0 | 4.5 | |
| 3 | 20 | 3.5 | 10 | 5.12 | 0 | 1.10 | 60 | 0 | 0 | 4.5 | |
| 4 | 20 | 3.5 | 10 | 3.00 | 0 | 7.50 | 70 | 0 | 0 | 4.5 | |
| 5 | 20 | 3.5 | 10 | 3.00 | 0 | 0.00 | 20 | 0 | 0 | 4.5 | |
| 6 | 20 | 3.5 | 10 | 0.00 | 0 | 3.75 | 15 | 0 | 0 | 4.5 | |
| 7 | 20 | 3.5 | 10 | 3.00 | 0 | 3.75 | 40 | 0 | 0 | 4.5 | |
| 8 | 20 | 3.5 | 10 | 3.00 | 0 | 3.75 | 40 | 0 | 0 | 4.5 | |
| 9 | 20 | 3.5 | 10 | 5.12 | 0 | 6.40 | 40 | 0 | 0 | 4.5 | |
| 10 | 20 | 3.5 | 10 | 0.88 | 0 | 1.10 | 60 | 0 | 0 | 4.5 | |
| 11 | 20 | 3.5 | 10 | 0 | 0.00 | 3.30 | 40 | 0 | 0 | 4.5 | |
| 12 | 20 | 3.5 | 10 | 0 | 0.70 | 0.97 | 20 | 0 | 0 | 4.5 | |
| 13 | 20 | 3.5 | 10 | 0 | 2.48 | 6.60 | 60 | 0 | 0 | 4.5 | |
| 14 | 20 | 3.5 | 10 | 0 | 0.70 | 5.63 | 70 | 0 | 0 | 4.5 | |
| 15 | 20 | 3.5 | 10 | 0 | 4.99 | 3.30 | 20 | 0 | 0 | 4.5 | |
| 16 | 20 | 3.5 | 10 | 0 | 4.25 | 0.97 | 15 | 0 | 0 | 4.5 | |
| 17 | 20 | 3.5 | 10 | 0 | 2.48 | 3.30 | 40 | 0 | 0 | 4.5 | |
| 18 | 20 | 3.5 | 10 | 0 | 2.48 | 0.00 | 40 | 0 | 0 | 4.5 | |
| 19 | 20 | 3.5 | 10 | 0 | 4.25 | 5.63 | 40 | 0 | 0 | 4.5 | |
| 20 | 20 | 3.5 | 10 | 0 | 2.48 | 3.30 | 60 | 0 | 0 | 4.5 | |
| 21 | 10 | 3.5 | 10 | 0 | 0 | 0 | 52 | 0 | 5 | 4.0 | Clinical Control |
| 22 | 40 | 5 | 10 | 0 | 0 | 0 | 40 | 0 | 5 | 4.5 | OEF w/CB |
| 23 | 0 | 2.5 | 0 | 0 | 0 | 0 | 0 | 181 | 5 | 4.0 | GRAS w/CB |
| 24 | 0 | 0 | 10 | 0 | 0 | 0 | 150 | 0 | 0 | 7.0 | ctrl no enh |
| 25 | | | | | | Media | | | | | |
| 25 | | | | | | Triton X | | | | | |

TABLE 26-continued

Permeation Results

| Sample | Avg % permeation | % std deviation |
|--------|------------------|-----------------|
| 14 | 39.8 | 15.1 |
| 15 | 24.8 | 10.7 |
| 16 | 25.3 | 2.4 |
| 17 | 27.0 | 13.5 |
| 18 | 18.7 | 5.9 |
| 19 | 27.2 | 16.5 |
| 20 | 21.2 | 3.2 |
| 21 | 13.3 | 4.3 |
| 22 | 32.6 | 5.6 |
| 23 | 20.0 | 3.2 |
| 24 | Out of range | Out of range |

Example 8

First Human Clinical Carbetocin Nasal Spray Formulation Pharmacokinetic Study Formulations for nasal spray administration containing various concentration of carbetocin for evaluation in human clinical studies were disclosed in Example 6, Table 22. In this Example, related formulations were administered to volunteer human subjects in a first (Phase 1) clinical study, as presented in Table 31.

Prior to initiating a first human clinical study, we tested IN carbetocin formulations containing a preservative for compliance with U.S. (i.e., USP) and European (EP) standards for antimicrobial testing. The USP Antimicrobial Effectiveness Testing (AET) requirements are shown in Table 27, test results are shown in Table 28. The EP Antimicrobial Effectiveness Testing (AET) requirements are shown in Table 29, test results are shown in Table 30.

TABLE 27

USP Testing Requirements

| | | Microorganism | | | | | | | | | |
|---|---|---|---|---|---|---|---|---|---|---|---|
| | | *P. acurginosa* | | *E. Coli* | | *S. aureus* | | *C. Albicans* | | *A. niger* | |
| | | Days | | | | | | | | | |
| | | 14 | 28 | 14 | 28 | 14 | 28 | 14 | 28 | 14 | 28 |
| USP | Log reduction (min) | 2.0 | No increase from day 14 | 2.0 | No increase from day 14 | 2.0 | No increase from day 14 | | No increase from day 14 | | No increase from day 14 |

TABLE 28

Results of USP AET

| | | Preservative combination | | | | |
|---|---|---|---|---|---|---|
| Me-β-CD (mg/ml) | Tonicifier | MP/PP (0.33/0.17 mg/ml) | CB (2.5 mg/ml) | CB (5 mg/ml) | MP/PP/CB (0.33/0.17/5.0 mg/ml) | MP/PP/BA (2.0/2.0/5.0 mg/ml) |
| 0 | NaCl | Pass | Pass | Pass | Pass | |
| 10 | NaCl | Pass | Pass | Pass | Pass | |
| 10 | Sorbitol | Pass | Pass | Pass | Pass | |
| 20 | NaCl | Pass Active only | Pass Active only | Pass | Pass | Pass |

The data presented in Table 30 indicate that formulations containing one or more preservatives meet USP criteria for AET.

TABLE 29

EP AET Testing Requirements

| | Microorganism | | | | | | | | |
|---|---|---|---|---|---|---|---|---|---|
| | *P. acurginosa* | | | *S. aureus* | | | *C. Albicans* | | *A. niger* | |
| | Days | | | | | | | | | |
| | 2 | 7 | 28 | 2 | 7 | 28 | 14 | 28 | 14 | 28 |
| Log reduction (Min) | 2.0 | 3.0 | No increase | 2.0 | 3.0 | No increase | 2.0 | No increase | 2.0 | No increase |

TABLE 30

Results of EP AET

| Me-β-CD (mg/ml) | Tonicifier | Preservative combination | | | | |
|---|---|---|---|---|---|---|
| | | MP/PP (0.33/0.17 mg/ml) | CB (2.5 mg/ml) | CB (5 mg/ml) | MP/PP/CB (0.33/0.17/5.0 mg/ml) | MP/PP/BA (2.0/2.0/5.0 mg/ml) |
| 0 | NaCl | Fail | Fail | Fail | Pass | |
| 10 | NaCl | Fail | Fail | Fail | Fail | |
| 10 | Sorbitol | Fail | Fail | Fail | Fail | |
| 20 | NaCl | Fail | Fail | Fail | Fail | Pass |

The data presented in Table 30 indicate that two formulations containing a combination of preservatives meet EP criteria for AET.

In a further study, we evaluated the formulations containing preservatives presented in Tables 27 and 30 for the ability to reduce transepithelial resistance (TER), as well as their impact on cell viability, cytotoxicity and permeation using the tracheal/bronchial epithelial cell membrane system (EpiAirway, MatTek Corp., Ashland, Mass.), as presented in Example 1.

The results from this epithelial cell in vitro study indicated that all formulations significantly reduced TER with high levels of cell viability, low levels of cytotoxicity, and carbetocin permeation levels from about 20% to about 44%. For example, the formulation containing MP/PP/Me-β-CD (10 mg/ml) provided about 22% permeation. Formulations containing high and low concentrations of CB in the presence of Me-β-CD (10 mg/ml) provided about 44% permeation, while the combination of MP/PP/CB/Me-β-CD (10 mg/ml) provided about 24% permeation. Formulations containing MP/PP without Me-β-CD or in the presence of 20 mg/ml Me-β-CD provided permeation levels at about 24%. In this experiment, the negative control showed very low levels of permeability (about 1.5%). The data from this experiment show that formulations containing CB provide the best permeation of carbetocin using the in vitro EpiAirway model system.

Based upon the first in vivo rabbit PK study presented in Example 2, and the results from AET testing (Tables 28 and 30) and permeation experiments, the formulation presented in Table 31 was manufactured and used in our first human clinical study (Phase 1).

TABLE 31

Human Clinical Nasal Spray Carbetocin Formulations

| | | Concentration | |
|---|---|---|---|
| Component | Compendial Status | (mg/mL) Depends on formulation potency required | (mM) |
| Methyl-β-cyclodextrin (Cavasol W7 M Pharma) | NA | 10.0 | ~7.4-7.5* |

TABLE 31-continued

Human Clinical Nasal Spray Carbetocin Formulations

| | | Concentration | |
|---|---|---|---|
| Component | Compendial Status | (mg/mL) Depends on formulation potency required | (mM) |
| Edetate Disodium | USP | 3.5 | 9.4 |
| L-Arginine hydrochloride | USP | 2.1 | 10.0 |
| Sodium Chloride | USP | 3.0 | 52.0 |
| Chlorobutanol (anhydrous) | NF | 5.0 | 28.2 |
| Hydrochloric Aicd, 10% diluted[1] | NF | As needed to achieve pH | |
| Sodium hydroxide[1] | NF | As needed to achieve pH | |
| Purified water or Sterile water for irrigation | USP | QS | |

[1]Added for pH adjustment to meet target pH of 4.0 + 0.3.
*Using an average MW of ~1317-1359 Da.

Figure 3:
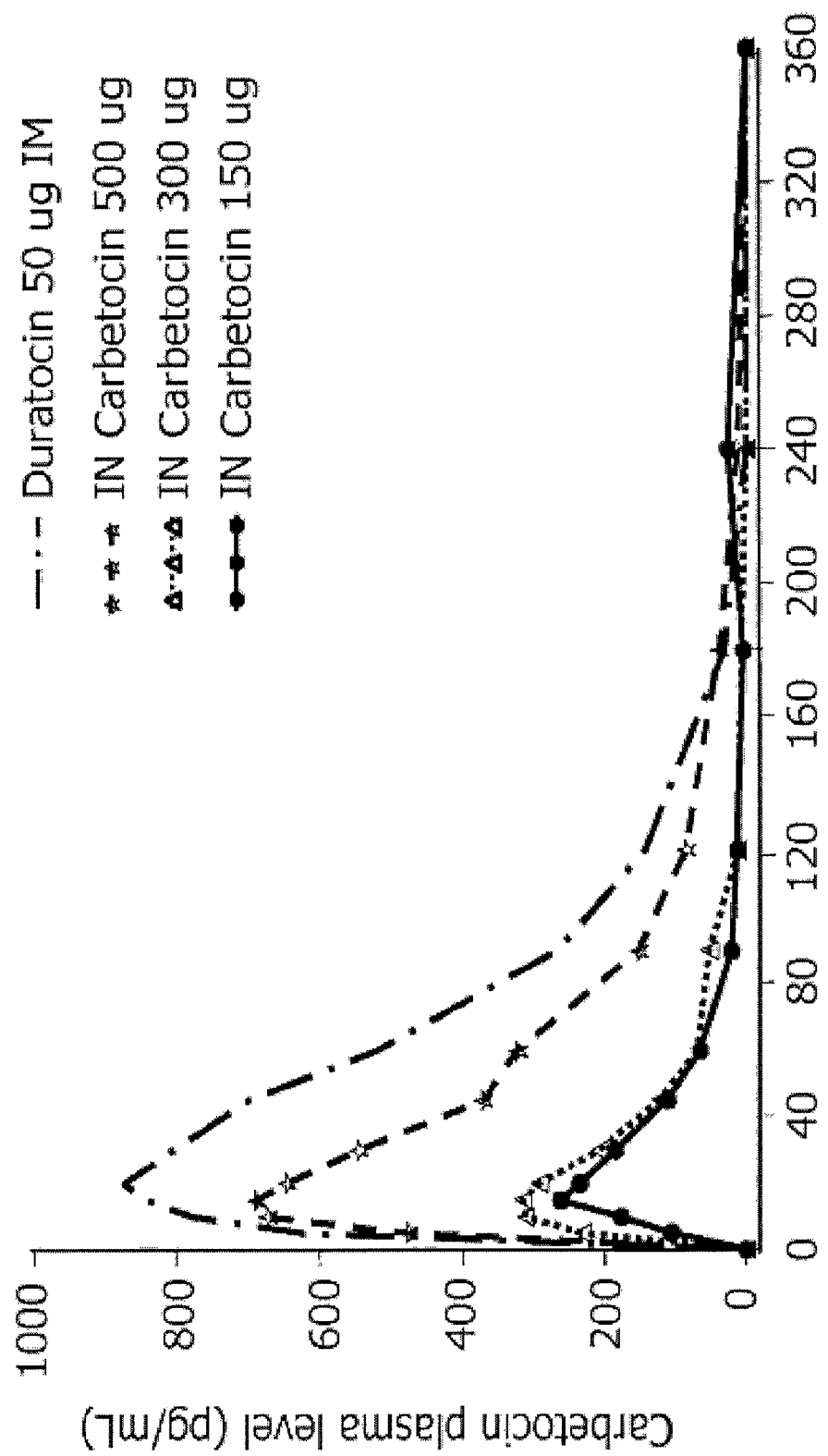
FIG. 3: Is a graph representing carbetocin plasma levels detected in subjects participating in a first human clinical study.

In this human clinical study (cross-over, dose escalating), the intranasal (IN) formulation of carbetocin was administered (a single dose) to 12 healthy human subjects (18-65 years old) at three strengths (150, 300, and 500 μg per dose) and compared to the 50 μg dose of Duratocin® administered by intramuscular injection (IM). Blood samples were taken periodically between t=0 (predose) and 6 hrs after dosing. The PK profile for IN and IM carbetocin is shown in FIG. 3. Significantly, as shown in FIG. 3, IN administered carbetocin formulations demonstrated a dose response for the systemic detection of carbetocin in plasma, the $C_{max}$ and $AUC_{last}$ both increased (see Table 32). Furthermore, it was also observed that variability, as described by the coefficient of variance (% CV), decreased with increasing absorption of drug. In this experiment, the bioavailability (BA) of the 500 μg dose was 7.0%. Unexpectedly, such a percent BA is greater than the 3-5% BA from detected in our first rabbit (i.e., pre-clinical) PK study.

TABLE 32

PK Prameters for Human Dosing of IN Carbetocin (% CV Shown in Parenthesis)

| Dose | $AUC_{last}$ (min * pg/ml) | Cmax (pg/ml) | Tmas (min) | T½ (min) | Kel (1/min) | Bioavailability |
|---|---|---|---|---|---|---|
| 50 μg IM | 64000 (17) | 930 (19) | 24 (54) | 35 (22) | 0.02 (24) | |
| 150 μg IN | 12000 (79) | 320 (89) | 38 (175) | 33 (83) | 0.03 (50) | 6 (74) |
| 300 μg IN | 15000 (75) | 430 (60) | 10 (47) | 46 (79) | 0.03 (69) | 4 (68) |
| 500 μg IN | 43000 (63) | 740 (40) | 18.6 (79) | 42 (56) | 0.02 (43) | 7 (72) |

In a further study, the stability of the IN administered formulations administered to human subjects were evaluated for stability at 5° C., 25° C. and 40° C., indicating that such formulations are expected to provide a 2 year shelf life at refrigerated conditions. No change in appearance, pH, or osmolality was detected at 5° C., 25° C. or 40° C. over a 6 month period of time. The data show that carbetocin remains stable over a 6 month period of time at both refrigerated and ambient conditions (i.e., 5° C. and 25° C., respectively). At the 6 month time point, total impurities have increased about 0.2% at refrigerated conditions and about 1.2% at ambient conditions (i.e., from the % impurities at T=0). There was a significant increase in total impurities for samples stored at 40° C. (from 6-9%). In addition, carbetocin stability was shown to increase with increasing carbetocin concentration.

Example 9

Rabbit PK Study 3, Improved Carbetocin Bioavailability

Figure 4:
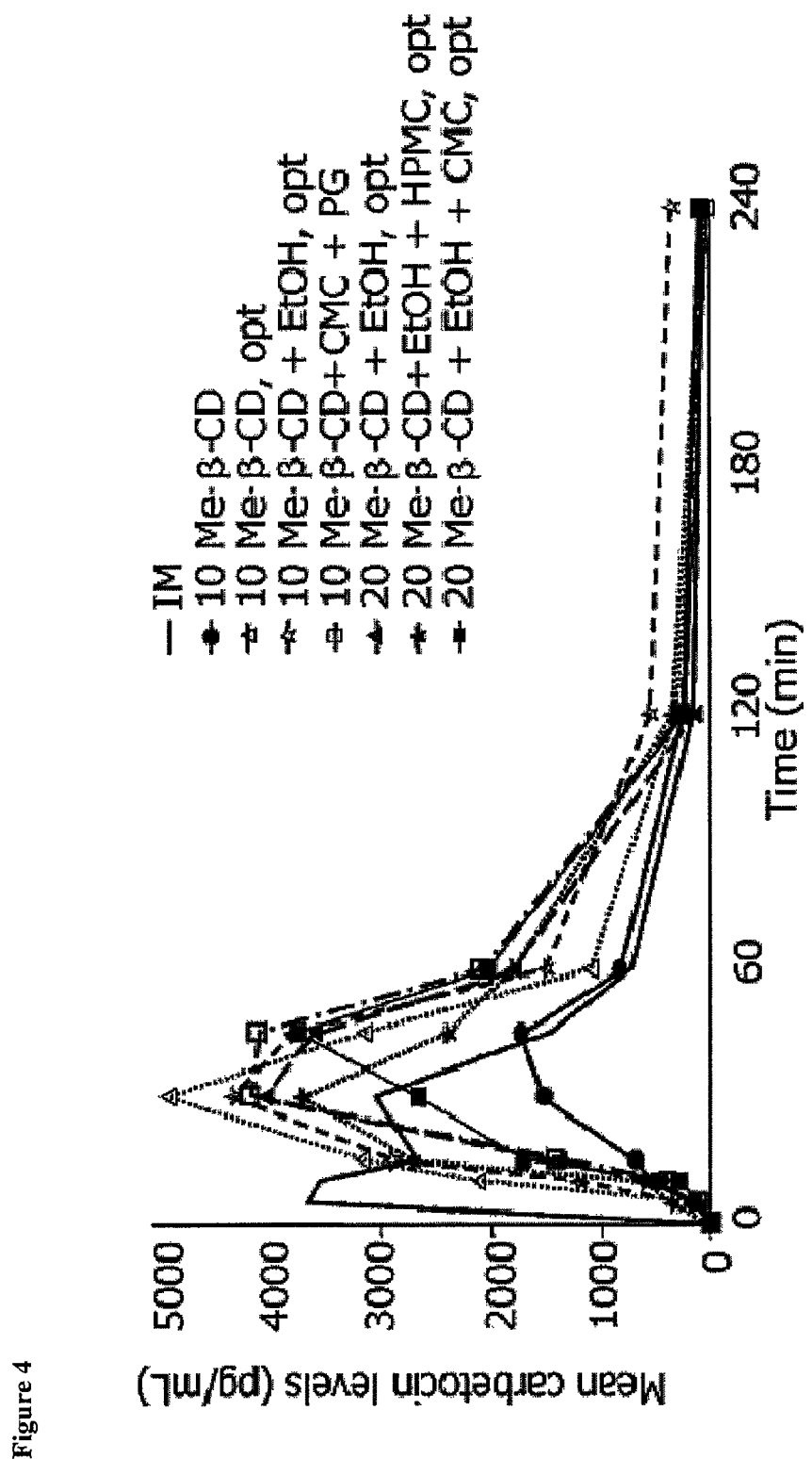
FIG. 4: Is a graph representing carbetocin PK results obtained from rabbit study 3.

In this Example, formulations evaluated for improved storage stability were tested for their ability to improve carbetocin BA in vivo. The results provided here are unexpected, showing increased in vivo bioavailability and chemical stability of carbetocin with increased pH (increasing from pH 4.0 to 4.5±0.3), osmolality (from about 170 mOsm/kg $H_2O$ to about 220 mOsm/kg $H_2O$) and addition of acetate as buffering agent (added to maintain pH at about 4.5±0.3). This change in formulation resulted in >2-fold increase in rabbit plasma (i.e., in vivo) bioavailability (see Table 33 and FIG. 4). This result is unexpected because the presence or absence of buffering agent (i.e., acetate), as well as slight changes in pH (<1-2 pH units) and osmolality (about 50 mOsm/kg $H_2O$) do not typically affect drug absorption across the nasal mucosa. Buffering agents and tonicifiers such as salt are not typically considered to be permeation enhancers.

TABLE 33

Rabbit PK Study 3, Bioavailability of Carbetocin

| # | Formulation | Bioavailability (%) |
|---|---|---|
| 2 | 1% Me-β-CD (1$^{st}$ Clinical formulation) | 2.90 |
| 3 | 1% Me-β-CD + OPT | 5.90 |
| 4 | 1% Me-β-CD + EtOH + OPT | 5.81 |
| 5 | 1% Me-β-CD + 0.1% CMC + OPT | 6.16 |
| 6 | 2% Me-β-CD + EtOH + OPT | 6.90 |
| 7 | 2% Me-β-CD + EtOH + 0.5% HPMC + OPT | 7.97 |
| 8 | 2% Me-β-CD + EtOH + 0.5% CMC + OPT | 6.04 |

OPT = 10 mM acetate buffering control agent

In this Example, eight groups of rabbits were dosed with the formulations presented in Table 34; group 1 received intramuscular (IM) carbetocin injection at 30 μg dose, while the remaining 7 groups received the 60 μg doses of intranasal (IN) carbetocin nasal spray formulations. The osmolality of Group 1 was about 350 mOsm/kg$H_2O$, the osmolality of Group 2 was about 180 mOsm/kg$H_2O$, and the osmolality of Groups 3 to 8 was about 215 mOsm/kg$H_2O$.

Formulations Administered in Rabbit PK Study 3

| # | Carbetocin (mg/ml) | Me-β-CD (mg/ml) | EDTA (mg/ml) | HPMC (mg/ml) | CMC LV (mg/ml) | NaCl (mM) | EtOH (mg/ml) | PG (mg/ml) | pH |
|---|---|---|---|---|---|---|---|---|---|
| 1 | 0.03 | 0 | 0 | 0 | 0 | 1.50 | 0 | 0 | 7.0 |
| 2 | 4 | 10 | 3.5 | 0 | 0 | 52 | 0 | 0 | 4.0 |
| 3 | 4 | 10 | 3.5 | 0 | 0 | 70 | 0 | 0 | 4.5 |
| 4 | 4 | 10 | 3.5 | 0 | 0 | 0 | 6 | 0 | 4.5 |
| 5 | 4 | 10 | 3.5 | 0 | 1 | 0 | 0 | 10 | 4.5 |
| 6 | 4 | 20 | 3.5 | 0 | 0 | 0 | 6 | 0 | 4.5 |
| 7 | 4 | 20 | 3.5 | 5 | 0 | 0 | 6 | 0 | 4.5 |
| 8 | 4 | 20 | 3.5 | 0 | 5 | 0 | 6 | 0 | 4.5 |

All groups contain 10 mM Arginine

Groups 2-8 contain 5 mg/mL chlorobutanol.

Groups 3-8 contain 10 mM Acetate.

Abbreviations:

EDTA = Edetate disodium,

Me-β-CD = Random methyl-β-cyclodextrin,

CB = chlorobutanol,

PG = propylene glycol,

CMC LV = carboxymethylcellulose sodium (low viscosity, 10-50 cps),

HPMC = hydroxypropylmethylcellulose 10 cps,

EtOH = Ethanol,

NaCl = Sodium Chloride

The results from this third rabbit PK study are summarized in Table 35. Briefly, in this rabbit PK study 3, Group 1 represents a control intramuscular injection; Group 2 represents a formulation used for our first human clinical study. Formulations 3-5 each contain 10 mg/ml Me-β-CD, 3.5 mg/ml EDTA, 10 mM arginine, 10 mM acetate buffer, pH 4.5±0.3 and, consequently, may be directly compared one to another, and in context with formulation 3, which may be considered a modified first human clinical formulation, may be viewed as testing the effect of pH, buffer, and osmolality on bioavailability (BA). Briefly, pH was increased to 4.5 and acetate buffer added for increased stability, osmolality was also increased to the target of 200-250 mOsm/kg $H_2O$. Formulation 4 is evaluated in part to confirm the effect of EtOH on BA, as improved permeation was seen in vitro, and as EtOH formulations w/o Me-β-CD were previously shown to produce similar BA relative to a formulation containing Me-β-CD w/o EtOH. In context with formulation #5, the design of this experiment is intended to further confirm the effect of CMC-LV on BA.

Formulation Nos. 6-8 each contain 20 mg/ml Me-β-CD, 3.5 mg/ml EDTA, 10 mM arginine, 10 mM acetate buffer, pH 4.5±0.3 and, consequently, may be directly compared one to another. In context with Formulation No. 6, we are evaluating the effect of increased Me-β-CD on permeation based upon improved permeation seen in vitro and results observed in rabbit PK studies 1 and 2. In this experiment, Formulation No. 6 may also be compared directly to Formulation No. 4. In Formulation No. 7, we are evaluating the effect of HPMC as a viscosity enhancer (as previously tested in vitro). In context with Formulation No. 8, we are testing the effect of CMC-LV as a viscosity enhancer (as previously tested in vitro).

TABLE 35

Rabbit Pharmacokinetic Study 3 results

| Formulation | Dose (μg/kg) | Tmax (min) | % CV | Cmax (pg/mL) | % CV | $AUC_{last}$ (min * pg/mL) | % CV | BA % |
|---|---|---|---|---|---|---|---|---|
| 1 IM dose | 3 | 13 | 75 | 4050 | 29 | 171200 | 20 | |
| 2 10 Me-β-CD | 60 | 29 | 43 | 1970 | 64 | 99300 | 34 | 2.9 |
| 3 10 Me-β-CD, opt | 60 | 33 | 20 | 4140 | 67 | 201900 | 64 | 5.9 |
| 4 10 Me-β-CD + EtOH opt | 60 | 27 | 25 | 4270 | 53 | 198900 | 36 | 5.8 |
| 5 10 Me-β-CD CMC + PG opt | 60 | 33 | 38 | 4250 | 38 | 210800 | 44 | 6.2 |
| 6 20 Me-β-CD + EtOH opt | 60 | 29 | 43 | 5280 | 63 | 236400 | 59 | 6.9 |
| 7 20 Me-β-CD + EtOh + HPMC | 60 | 36 | 23 | 4770 | 66 | 272800 | 59 | 8.0 |
| 8 20 Me-β-CD + EtOH + CMC opt | 60 | 39 | 21 | 4090 | 47 | 206800 | 48 | 6.0 |

As shown in Table 35, improving the formulation for stability alone produced the greatest change in carbetocin exposure, resulting in more than a two fold increase in relative BA (2.9 vs. 5.9%). The two fold increase was also see in $AUC_{last}$ (99300 vs. 201900 min*pg/ml) and $C_{max}$ (1970 vs. 4140 pg/ml). Increasing Me-β-CD from 10 to 20 mg/ml and/or adding EtOH did not further increase relative BA (5.9-6.9%), $AUC_{last}$ (198900-236400 min*pg/ml), or $C_{max}$ (4270-5280 pg/ml) above the levels produced with the stability improvement alone. These results do not correlate with corresponding in vitro permeation results (see Table 36).

TABLE 36

In vitro Permeation Data for Rabbit Pharmacokinetic Study 3 Formulations

| Group | TER T = 0 | TER T = 60 min | Permeation % | Permeation % std dev | MTT % | MTT % std dev | Apical LDII % | Apical LDII % std dev | Basolateral LDH % | Basolateral LDH % std dev |
|---|---|---|---|---|---|---|---|---|---|---|
| 1 | 722.0 | 35.0 | 22.0 | 5.6 | 97.8 | 19.0 | 10.6 | 4.5 | 3.1 | 0.4 |
| 2 | 615.4 | 28.2 | 11.7 | 3.2 | 119.5 | 21.3 | 13.5 | 5.8 | 2.6 | 0.4 |
| 3 | 682.2 | 78.8 | 7.5 | 0.7 | 101.5 | 17.6 | 20.3 | 23.7 | 2.8 | 0.7 |
| 4 | 549.8 | 40.4 | 16.3 | 2.5 | 115.3 | 21.9 | 9.6 | 3.2 | 2.9 | 0.4 |
| 5 | 518.6 | 55.4 | 26.7 | 5.5 | 110.6 | 23.0 | 16.3 | 7.4 | 3.9 | 0.8 |
| 6 | 524.6 | 60.0 | 24.0 | 1.0 | 103.6 | 20.5 | 19.5 | 14.8 | 4.1 | 0.5 |
| 7 | 643.4 | 39.2 | 29.3 | 1.2 | 117.9 | 22.4 | 19.6 | 18.6 | 3.8 | 0.6 |
| 8 | 575.2 | 14.8 | 33.3 | 4.0 | 113.8 | 22.1 | 10.2 | 6.4 | 4.6 | 0.7 |
| 9 | 559.4 | 82.4 | 13.7 | 1.5 | 89.3 | 16.8 | 17.9 | 9.7 | 2.7 | 0.4 |
| 10 | 587.2 | 605.4 | 0.0 | 0.0 | 102.9 | 18.8 | 7.6 | 5.6 | 2.1 | 0.3 |
| Media | 628.6 | 581.0 | | | 100.0 | 21.2 | 10.4 | 5.8 | 2.1 | 0.4 |
| Triton | 504.4 | 0.2 | | | 1.4 | 0.3 | 100.0 | 20.3 | 100.0 | 171. |

TER results are in ohm × cm$^2$

In this study, the effects of viscosity enhancers on carbetocin permeation indicate that the addition of CMC to the "20 Me-β-CD+EtOH, opt" formulation slightly decreased BA (6.0% with CMC vs. 6.9% without), $AUC_{last}$ (206800 vs. 236400 min*pg/mL), and $C_{max}$ (4090 vs. 5280 pg/mL). Similarly, the addition of CMC to the "10 Me-β-CD opt" formulation decreased carbetocin exposure. Conversely, formulations with HPMC produced the highest relative BA and $AUC_{last}$; the $C_{max}$ for "20 Me-β-CD+EtOH+HPMC, opt" was second only to the "Me-β-CD+EtOH opt" formulation.

The formulation (10 Me-β-CD+CMC+PG) was shown to have improved stability and had a 6.7% rel BA. The formulation "20 Me-β-CD+EtOH+HPMC, opt" produced the highest relative BA (8.0%) and $AUC_{last}$ (272800 min*pg/ml). However, "20 Me-β-CD+EtOH, opt" had the highest $C_{max}$ (5280 pg/ml) and comparable relative BA (6.9%) and $AUC_{last}$ (236400 min*pg/ml) to the HPMC containing formulation. This suggested that HPMC does not, at least in this study, provide a large increase in carbetocin exposure.

Statistical analysis of the data was performed to assess the statistical difference of formulation performance. It was determined that all IN formulations were not statistically different from the IM control for $AUC_{last}$, $C_{max}$, and bioavailability (see Table 37).

TABLE 37

P-value Summary of IN Formulation in Rabbit Pharmacokinetic Study 3 Relative to IM Control

|  | Treatment Group | P-value |
|---|---|---|
| $AUC_{last}$ (min*pg/ml) | 2 | 0.8052 |
|  | 3 | 0.9971 |
|  | 4 | 0.9985 |
|  | 5 | 0.9872 |
|  | 6 | 0.8644 |
|  | 7 | 0.4977 |
|  | 8 | 0.9930 |
| Cmax (pg/ml) | 2 | 0.5724 |
|  | 3 | 1.0000 |
|  | 4 | 1.0000 |
|  | 5 | 1.0000 |
|  | 6 | 0.9297 |
|  | 7 | 0.9958 |
|  | 8 | 1.0000 |
| Bioavailiability (%) | 2 | 0.5114 |
|  | 3 | 0.5402 |
|  | 4 | 0.4295 |
|  | 5 | 0.2410 |
|  | 6 | 0.0895 |
|  | 7 | 0.4656 |
|  | 8 | 0.8052 |

For this experiment, 25 ml of each intranasal (IN) formulation was prepared. All IN formulations were stored in 3×1 ml aliquots in 1cc amber glass bottles. Also, 400 ml of the intramuscular (IM) formulation was prepared and stored in 3×3 mL aliquots in 3 cc clear glass bottles. All formulations were stored at 2-8° C.

In summary, the results from this rabbit PK study 3 (see FIG. 4) provide a 2-fold increase in bioavailability with the OPT formulation, and may indicate that the addition of HPMC enhances performance. Data from this rabbit PK study 3 indicate that carbetocin BA is about 9% compared to 5-6% observed in previous rabbit PK studies. Further, based upon statistical analysis, the IN BA in this experiment is not significantly different from that obtained from IM injection.

The data from this third in vivo PK study, summarized in Table 35, and the corresponding in vitro permeation study provided in Table 36, were examined for the possibility of an in vitro—in vivo correlation (IVIVC). No correlation was observed comparing in vivo bioavailability, $AUC_{last}$, or $C_{max}$ with in vitro permeation of carbetocin ($R^2$=0.0188, 0.0203, 0.0042, respectively). The lack of correlation for any of these PK parameters suggests the permeation observed in vitro was not predictive of the in vivo exposure in rabbits When taken together, such data have led us to propose a formulation for a second human clinical study (see Table 38).

TABLE 38

Formulation for Human PK Clinical Study 2

|  |  | Concentration | |
|---|---|---|---|
| Component Carbetocin | Compendial Status | (mg/ml) Depends on formulation potency required | (mM) Depends on formulation potency required |
| Methyl-β-cyclodextrin (Cavasol W7 M Pharma) | NA | 10.0 | ~74-75* |
| Edetate Disodium | USP | 3.5 | 9.4 |
| L-Arginine hydrochloride | USP | 2.1 | 10.0 |
| Sodium Acetate, anhydrous | USP | 0.336 | 10.0 |
| Glacial Acetic Acid | USP | 0.348 | |
| Sodium Chloride | USP | 4.09 | 70 |
| Chlorobutanol (anhydrous) | NF | 5.0 | 28.2 |
| Hydrochloric Acid, 10% diluted[1] | NF | As needed to achieve pH | |
| Sodium hydroxide[1] | NF | As needed to achieve pH | |
| Purified water or Sterile water for irrigation | USP | QS | |

[1]Added for pH adjustment to meet target pH of 4.5 ± 0.3.
*Using an average MW of ~1317-1359 Da.

The proposed design of human PK clinical study 2 (e.g., IM-comparison, dose-ranging) may include 12 healthy human subjects 18-65 years of age; treatment groups such as Duratocin IM, Oxytocin (Syntocin) at 24 IU, carbetocin IN at 150, 250 and 400 pg/dose.

The formulation designated "10 Me-β-CD, opt" was chosen due to the increased $AUC_{last}$ seen in vivo as compared to the previous clinical formulation. More complex formulations were not selected at this time for clinical evaluation because statistical analysis suggested that the effect of additional excipients did not provide significantly different increases in AUC or $C_{max}$. While the in vivo data suggested that the formulation "20 Me-β-CD+EtOH+HPMC opt" may have had a greater BA, due to lack of statistical significance for the in vivo data, this formulation was not pursued at this time, but may very well be tested in subsequent studies.

In this second clinical trial, three concentrations of carbetocin were manufactured based on the formulation disclosed in Table 38 in order to provide a carbetocin dose of 150 µg, 250 µg, and 400 µg. Blood samples for PK analysis of carbetocin and oxytocin levels were collected in EDTA coated blood collection tubes from patients. Aprotinin was immediately added and the samples were centrifuged to obtain plasma samples. Intranasal (IN) formulation of carbetocin were dosed using a 100 µl actuator in 12 healthy, human subjects at three strengths (1.5, 2.5, and 4.0 mg/ml) and compared to intramuscular (IM) dose of Duratocin® (Carbetocin Injection). An additional comparison to the commercially available version of intranasal oxytocin (Syntocinon Spray®) was also conducted. Blood samples were taken periodically between t=0 (predose) and 6 hrs.

The PK profile for IN carbetocin demonstrated a dose response trend; with increasing dose, the $C_{max}$ and $AUC_{last}$ both increased (Table 39). This was previously observed in our first clinical study disclosed herein. The bioavailability of the 150 and 400 µg dose was 7% relative to the IM dose while that of the 250 µg dose was 6%. This bioavailability is similar to that of the previous Carbetocin formulation dosed in our first clinical study.

TABLE 39

PK Parameters for Second Clinical Study

| | $AUC_{last}$ (min*pg/ml) | (Cmax (pg/ml) | Tmax (min) | Bioavailability |
|---|---|---|---|---|
| 50 μg IM | 62049 (23) | 839 (22) | 23 (26) | |
| 150 μg | 13697 (121) | 222 (87) | 15 (47) | 7 |
| 250 μg | 18113 (46) | 377 (32) | 18 (46) | 6 |
| 400 μg | 32500 (95) | 608 (66) | 13 (39) | 7 |

The result of the clinical study described is somewhat unexpected, based on the rabbit PK study which was used to select the formulation evaluated, which showed a greater than 2-fold increase in bioavailability relative to the first clinical formulation evaluated. This result was not duplicated in this second human study, but instead, a comparable bioavailability was observed. It is worthwhile to note that the $AUC_{last}$ values of the IM control doses in both clinical studies compare very well (64000 min*pg/ml in the first study vs. 62049 min*pg/ml in the second) indicating good reliability of the data.

The stability of the formulation evaluated in this second clinical study is being evaluated in an ongoing controlled stability study. Early stability results of carbetocin in the IN formulation indicate that the formulations are very stable after storage for two months even at 40 C, when total impurities did not exceed 2.5% and peptide content did not change by more than 1%.

Further, the improved formulation(s) disclosed, has significantly improved stability relative to the formulation tested in human clinical study 1, as total impurities are decreased by approximately half after storage for 2 months at 40° C. Formulations used in our first human clinical study had about 5% total impurities after 2 months of storage at 40° C., while, in contrast, the improved formulation has about 2.5% total impurities after 2 months of storage at 40° C. For the improved formulation, after 2 months of storage at 40° C., total impurities increased by about 1.25% from what was detected at T=0. The increased stability may be attributed to the increase in pH.

For this stability testing (of an improved formulation), 14 bottles of manufactured formulation were placed on stability. Six bottles were placed at 5° C. (including three extras), four bottles at 25° C. (including one extra), and four bottles at 40° C. (including one extra). The time points for each sample to be removed for testing was defined as the specified date±3 days (see Table 40 for sampling schedule). For each time point, the specified date and the actual pull date was noted. After 3 months for 40° C. samples, and 6 months for 5° C. and 25° C. samples, results were assessed in order to determine if the study will proceed with further time points out to six months for 40° C. samples, and 12 months for 25° C. samples and 12, 18, or 24 months for 5° C. samples.

One bottle was sampled (i.e., pulled) for each condition/time point following the sampling schedule and measured for pH, osmolality, clarity, peptide content and purity by RP-HPLC, and chlorobutanol content. If a sample shows identifiable physical instability (i.e. precipitation) at any time point, it was noted and only clarity, pH, and osmolality testing was performed on the sample for that time point. Such sample is removed from all future time point testing. Placebos of each formulation are also placed on stability following the same sampling schedule. The placebos were examined for visual appearance and may be used for HPLC testing, as necessary. For the time points evaluated, there was no change in appearance, pH, osmolality, carbetocin or CB content. Total impurities remained constant at 5° C. and 25° C.

In this stability test, pH s measured using a Cole Parmer semi-micro NMR tube glass pH probe (cat #05990-30) with an Orion 520Aplus pH meter (Thermo Electron Corp (USA)) or equivalent. Osmolality was measured with an Advanced Multichannel Osmometer, Model 2020 from Advanced Instruments Inc. (Norwood, Mass.) or equivalent. Calibration preceded the measurement of each sample. Clarity was determined by visual inspection.

TABLE 40

Sampling Schedule for Stability Testing

| Time point: | 1 mo | 2 mo | 3 mo | 6 mo |
|---|---|---|---|---|
| 5° C. (# bottles to pull) | 1 | 0 | 1 | 1 |
| 25° C. (# bottles to pull) | 1 | 0 | 1 | 1 |
| 40° C. (# bottles to pull) | 1 | 1 | 1 | 0 |

In more detail, stability data is presented for the formulations evaluated in this second clinical study (see Table 38 as well as our first clinical study (see Table 31)). A zero time sample was completed as part of release testing. The improved stability of the formulation evaluated in the second clinical study is likely to provide a commercial product that can be manufactured which can support room temperature storage for the "as sold" as well as "in use" configuration for up to two years. One non-obvious result reported in multiple experiments is that physical stability at 25° C. is comparable to that at 5° C. This is unexpected because, for peptides, stability is more likely expected to increase with decreasing storage temperatures. The formulations evaluated in this stability study are shown in Table 41.

TABLE 41

Carbetocin Formulations for Stability Testing

| # | Carbetocin (mg/ml) | Me-β-CD (mg/ml) | EDTA (mg/ml) | HPMC (mg/ml) | CMC LV (mg/ml) | NaCl (mM) | EtOH (mg/ml) | PG (mg/ml) | pH |
|---|---|---|---|---|---|---|---|---|---|
| 2* | 4 | 10 | 3.5 | 0 | 0 | 52 | 0 | 0 | 4.0 |
| 3** | 4 | 10 | 3.5 | 0 | 0 | 70 | 0 | 0 | 4.5 |
| 4 | 4 | 10 | 3.5 | 0 | 0 | 0 | 6 | 0 | 4.5 |
| 5 | 4 | 10 | 3.5 | 0 | 1 | 0 | 0 | 10 | 4.5 |
| 6 | 4 | 20 | 3.5 | 0 | 0 | 0 | 6 | 0 | 4.5 |

TABLE 41-continued

Carbetocin Formulations for Stability Testing

| # | Carbetocin (mg/ml) | Me-β-CD (mg/ml) | EDTA (mg/ml) | HPMC (mg/ml) | CMC LV (mg/ml) | NaCl (mM) | EtOH (mg/ml) | PG (mg/ml) | pH |
|---|---|---|---|---|---|---|---|---|---|
| 7 | 4 | 20 | 3.5 | 5 | 0 | 0 | 6 | 0 | 4.5 |
| 8 | 4 | 20 | 3.5 | 0 | 5 | 0 | 6 | 0 | 4.5 |

*Group 2 = Formulation dosed in clinical study #1.
**Group 3 = Formulation dosed in clinical study #2.
All groups contain 10 mM Arginine.
Groups 2-8 contain 5 mg/mL chlorobutanol.
Groups 3-8 contain 10 mM Acetate.
Abbreviations:
EDTA—Edetate disodium,
Me-β-CD—Random methyl-β-cyclodextrin,
CB—chlorobutanol,
PG—propylene glycol,
CMCLV = carboxymethylcellulose sodium (low viscosity, 10-50 cps),
HPMC = hydroxypropylmethylcellulose 10 cps,
EtOH—Ethanol,
NaCl—Sodium Chloride The time point window for each sample removed from storage (based on the schedule provided in Table 40 was defined as the specified date±3 days. For each time point, the specified date and the actual pull date was noted. After 3 months for 40° C. samples, and 6 months for 5° C. and 25° C. samples, results were assessed to determine if the study would proceed with further time points out to six months for 40° C. samples, and 12 months for 25° C. samples and 12, 18, or 24 months for 5° C. samples. For this stability study, sample pH was measured using a Cole Parmer semi-micro NMR tube glass pH probe (Cat NO. 05990-30) with Orion 520Aplus pH meter, Thermo Electron Corp (USA) or equivalent. Osmolality was measured with an Advanced Multichannel Osmometer, Model 2020 from Advanced Instruments Inc. (Norwood, Mass.) or equivalent. Calibration preceded the measurement of sample. Samples was measured for clarity by visual observation. Purity and content was determined by HPLC analysis.

A summary of the chemical testing results for all samples stored at 5° C., 25° C. and 40° C. across all tested time points up to 3 months, as well projected future values predicted by linear regression, where data could produce a sufficient $R^2$ (>0.7), is shown in Tables 42, 43 and 44 respectively.

Sample pH and osmolality remained consistent with t=0 through the three month time point. All formulations, when stored at 5° C. for three months showed an increase in total impurities of about <0.1% when compared to t=0 values indicating excellent stability at refrigerated conditions. Projected total impurities using linear regression could not be predicted due to lack of significant slope based on actual data collected to date.

TABLE 42

HPLC Data Summary for Samples Under 5° C. Storage Conditions

| Testing Parameter | Sample | Time Points (Months) | | | Projected values (utilizing linear regression) | | | |
|---|---|---|---|---|---|---|---|---|
| | | 0 | 1 | 3 | 6 | 12 | 24 | 48 |
| Average Percent Impurities | 2* | 1.1 | 1.3 | 1.2 | — | — | — | — |
| | 3** | 1.1 | 1.3 | 1.1 | — | — | — | — |
| | 4 | 1.1 | 1.3 | 1.1 | — | — | — | — |
| | 5 | 1.1 | 1.3 | 1.2 | — | — | — | — |
| | 6 | 1.1 | 1.3 | 1.2 | — | — | — | — |
| | 7 | 1.2 | 1.3 | 1.1 | — | — | — | — |
| | 8 | 1.1 | 1.3 | 1.2 | — | — | — | — |

TABLE 42-continued

HPLC Data Summary for Samples Under 5° C. Storage Conditions

| Testing Parameter | Sample | Time Points (Months) | | | Projected values (utilizing linear regression) | | | |
|---|---|---|---|---|---|---|---|---|
| | | 0 | 1 | 3 | 6 | 12 | 24 | 48 |
| Average content by % Label Claim | 2* | 105.6 | 103.8 | 101.7 | 97.8 | 90.2 | 75.0 | 44.7 |
| | 3** | 102.6 | 100.8 | 100.7 | 98.8 | 95.5 | 88.9 | 75.7 |
| | 4 | 102.8 | 100.2 | 99.5 | 96.2 | 90.2 | 78.3 | 54.5 |
| | 5 | 103.5 | 100.6 | 100.0 | 96.5 | 90.2 | 77.7 | 52.7 |
| | 6 | 103.6 | 101.4 | 100.6 | 97.6 | 92.1 | 81.1 | 59.2 |
| | 7 | 101.4 | 98.7 | 97.5 | 93.6 | 86.4 | 72.0 | 43.2 |
| | 8 | 101.1 | 100.2 | 98.7 | 96.3 | 91.5 | 82.0 | 63.0 |
| Average % chlorobutanol content | 2* | 95.5 | 94.8 | 95.6 | — | — | — | — |
| | 3** | 97.3 | 97.1 | 98.4 | — | — | — | — |
| | 4 | 95.6 | 95.4 | 96.1 | — | — | — | — |
| | 5 | 96.2 | 94.4 | 95.5 | — | — | — | — |
| | 6 | 98.6 | 98.3 | 98.7 | — | — | — | — |
| | 7 | 94.8 | 93.8 | 94.5 | — | — | — | — |
| | 8 | 95.0 | 96.4 | 96.3 | — | — | — | — |

*Group 2 = Formulation dosed in clinical study #1).
**Group 3 = Formulation dosed in clinical study #2)

The loss in peptide content (by % label claim), relative to t=0, for storage at 5° C. for three months was <4% for all formulations tested in this stability study. More importantly, the loss in peptide content of Formulation No. 3 (the most recent clinical formulation) was half of that seen in Formulation No. 2 (the first clinical formulation) showing the significant improvement in stability of the second clinical formulation over the first clinical formulation. This improvement in stability was further demonstrated in samples stored at 25° C. and 40° C. Furthermore, a typical specification for API content in the finished product would 80-120% label claim. The second clinical formulation (Group 3) is predicted, by linear regression to have 89% carbetocin label claim at 2 years (24 M) at 5° C., which would remain within the specification, while the first clinical formulation (Group 2) would likely not meet this goal of maintaining the specification for 2 years. Chlorobutanol content remained within 1% of initial concentration showing the compound remained stable.

For samples evaluated under 25° C. storage conditions, pH and osmolality remained consistent with t=0 through the three month time point. The corresponding HPLC analysis representing purity and content is shown on in Table 43. The data show that the percent total impurities of samples stored at 25° C. for three months increased by up to about 0.6% in formulations at pH 4.5 (Samples 3-8) while the increase was approximately twice that (1.4% increase) for Formulation No. 2 (the first clinical formulation). Performing linear regression on the 25° C. total impurity data produced $R^2$ values>0.8 for all groups except No. 7. The predicted percent total impurities of Formulation No. 2 after 24 month storage at 25° C. is 11.4%, which is twice the predicted percent total impurities for Formulation No. 3 of 5.8% (the current clinical formulation). This is further evidence of the improved stability of the second clinical formulation over the first one. Furthermore, the total impurities after 2 years at 25° C. are predicted to be well below 10%, which presents a viable option for a commercial product capable of long term storage at room temperature.

For samples stored at 25° C. for three months, there was <4% loss in peptide content (by % label claim) when compared to t=0 values, indicating good stability. Remarkably, this is very similar to the peptide content results for storage at refrigerated conditions, suggesting that physical stability is not significantly improved by refrigeration for these carbetocin formulations. The predicted peptide content values at 2 years storage at 25° C., based on linear regressions with $R^2$ values>0.8 for all but sample 5, suggest that nearly all the formulations in this stability study will come close to having 80% label claim for carbetocin. This similar result for refrigerated and room temperature results is unexpected since the stability of most peptides improves with storage under decreasing temperatures. In these stability studies, 25° C. storage conditions, chlorobutanol content remained within 1% of initial concentration showing the compound remained stable.

TABLE 43

HPLC Data Summary for Samples Under 25° C. Storage Conditions

| HPLC Data | | Time Points (Months) | | | | Projected values (utilizing linear regression) | | | |
|---|---|---|---|---|---|---|---|---|---|
| Field | Sample | 0 | 1 | 3 | 6 | 12 | 24 | 48 |
| Average Percent Impurities | 2* | 1.1 | 1.6 | 2.4 | 3.7 | 6.3 | 11.4 | 21.7 |
| | 3** | 1.1 | 1.4 | 1.7 | 2.3 | 3.5 | 5.8 | 10.4 |
| | 4 | 1.1 | 1.4 | 1.5 | 1.9 | 2.6 | 4.1 | 7.0 |
| | 5 | 1.1 | 1.4 | 1.5 | 1.9 | 2.6 | 4.1 | 7.0 |
| | 6 | 1.1 | 1.4 | 1.5 | 1.9 | 2.6 | 4.1 | 7.0 |
| | 7 | 1.2 | 1.5 | 1.5 | 1.8 | 2.3 | 3.3 | 5.4 |
| | 8 | 1.1 | 1.5 | 1.6 | 2.1 | 3.0 | 4.8 | 8.4 |
| Average content by % Label Claim | 2 | 105.6 | 104.1 | 102.7 | 99.8 | 94.2 | 83.1 | 60.8 |
| | 3 | 102.6 | 100.6 | 99.3 | 96.0 | 89.8 | 77.4 | 52.5 |
| | 4 | 102.8 | 100.4 | 99.1 | 95.4 | 88.5 | 74.7 | 47.1 |
| | 5 | 103.5 | 100.8 | 100.2 | 96.9 | 91.0 | 79.2 | 55.5 |
| | 6 | 103.6 | 102.0 | 100.1 | 96.6 | 89.8 | 76.2 | 48.9 |
| | 7 | 101.4 | 100.8 | 98.4 | 95.4 | 89.2 | 76.9 | 52.2 |
| | 8 | 101.1 | 99.9 | 98.1 | 95.1 | 89.2 | 77.4 | 53.7 |
| Average % chloro-butanol content | 2 | 95.5 | 95.7 | 96.7 | — | — | — | — |
| | 3 | 97.3 | 96.7 | 97.2 | — | — | — | — |
| | 4 | 95.6 | 95.2 | 95.4 | — | — | — | — |
| | 5 | 96.2 | 94.9 | 95.9 | — | — | — | — |
| | 6 | 98.6 | 99.2 | 99.4 | — | — | — | — |
| | 7 | 94.8 | 96.1 | 95.8 | — | — | — | — |
| | 8 | 95.0 | 95.8 | 96.2 | — | — | — | — |

*Group 2 = Formulation dosed in clinical study #1.
**Group 3 = Formulation dosed in clinical study #2)

The stability analysis for samples stored under 40° C. storage conditions (see Table 44), while osmolality remained consistent with t=0 through the three month time point, pH did drop significantly for all formulations stored at 40° C. In this study, sample pH was, for example, observed to drop 0.1-0.3 pH units by the three month time point for all formulations. The 40° C. storage condition may be considered an accelerated temperature condition for room temperature (i.e., 25° C.) storage. The total impurities in Formulation No. 2 (the first clinical formulation) was 6.3% at 40° C. which is twice the 2.9% total impurities observed in Formulation No. 3 (the second clinical formulation). All formulations at pH 4.5 (Samples 3-8) demonstrated markedly improved stability relative to Formulation No. 2, which was made at pH 4.0. Additionally, the predicted total impurities at 12 months (as determined by linear regression) for Formulation No. 2 is almost approximately 2.5 times that predicted for Formulation No. 3 (22% vs. 9% total impurities, respectively).

When stored at 40° C. over three months, there was an about 8% loss in peptide content of Formulation No. 2 compared to its t=0 value. The loss in Formulation No. 3 was significantly less at about 4%. Note that Formulation Nos. 6 and 7 actually demonstrated significant increases in concentration. This effect is most likely a consequence of evaporation due to loose caps when the samples were stored at 40° C.

TABLE 44

HPLC Data Summary for Samples Under 40° C. Storage Conditions

| HPLC Data | | Time Points (Months) | | | | Projected values (utilizing linear regression) | |
|---|---|---|---|---|---|---|---|
| Field | Sample | 0 | 1 | 2 | 3 | 6 | 12 |
| Average Percent Impurities | 2* | 1.1 | 3.1 | 5.0 | 6.3 | 11.8 | 22.3 |
| | 3** | 1.1 | 1.9 | 2.7 | 2.9 | 4.9 | 8.7 |
| | 4 | 1.1 | 1.8 | 2.6 | 3.1 | 5.2 | 9.3 |
| | 5 | 1.1 | 2.0 | 2.9 | 3.7 | 6.3 | 11.6 |
| | 6 | 1.1 | 1.9 | 2.8 | 3.6 | 6.1 | 11.2 |
| | 7 | 1.2 | 2.0 | 2.9 | 3.9 | 6.6 | 12.0 |
| | 8 | 1.1 | 2.2 | 3.4 | 4.8 | 8.4 | 15.8 |
| Average content by % Label Claim | 2* | 105.6 | 101.0 | 98.9 | 97.2 | — | — |
| | 3** | 102.6 | 100.8 | 99.4 | 98.8 | — | — |
| | 4 | 102.8 | 100.4 | 102.9 | 101.5 | — | — |
| | 5 | 103.5 | 101.6 | 100.9 | 102.1 | — | — |
| | 6 | 103.6 | 102.2 | 105.4 | 111 | — | — |
| | 7 | 101.4 | 101.5 | 101.2 | 122.9 | — | — |
| | 8 | 101.1 | 103.3 | 100.2 | 100.5 | — | — |
| Average % chlorobutanol content | 2* | 95.5 | 94.3 | 96.0 | 96.7 | — | — |
| | 3** | 97.3 | 96.3 | 98.0 | 97.2 | — | — |
| | 4 | 95.6 | 94.7 | 98.6 | 95.4 | — | — |
| | 5 | 96.2 | 94.4 | 95.8 | 95.9 | — | — |
| | 6 | 98.6 | 99.3 | 103.1 | 99.4 | — | — |
| | 7 | 94.8 | 96.7 | 97.2 | 95.8 | — | — |
| | 8 | 95.0 | 99.1 | 96.7 | 96.2 | — | — |

*Group 2 = Formulation dosed in clinical study #1.
**Group 3 = Formulation dosed in clinical study #2.

A subsequent "long term" stability study (stability study two in this Example) was performed on non-clinical formulations consistent with the formulation disclosed in Table 38, as used in our 14 day non-clinical toxicity studies, at two carbetocin concentrations (see table 45). Samples were evaluated at t=0, and t=1, 2 and 3 months of storage. For each formulation, time zero testing was completed as a part of release testing. For this study, 14 bottles were put on stability: Six bottles at 5° C. (includes three extras), four bottles at 25° C. (includes one extra), and four bottles at 40° C. (includes one extra). The time point window for each sample removed from storage was defined as the specified date±3 days. For each time point, the specified date and the actual pull date were noted.

One bottle was pulled for each condition/time point following the pull schedule and measured for pH, osmolality, clarity, peptide content and purity by RP-HPLC, and chlorobutanol content. If a sample showed identifiable physical instability (i.e. precipitation) at any time point, it was noted in analyst's notebook and only clarity, pH, and osmolality testing was performed on the sample for that time point. The sample was removed from all future time point testing. Stability of any sample could be terminated at any point during the study. An explanation for termination would be recorded in the notebook. Placebos from STAB07072 were used as comparators for these studies. The placebos were examined for visual appearance and may be used for HPLC testing if it was determined necessary.

TABLE 45

Formulations for Long Term Stability Study

| Formulation # | Lot # | Carbetocin (mg/ml) | Me-β-CD (mg/ml) | EDTA (mg/ml) | Arginine (mM) | Acetate (mM) | NaCl (mM) | CB (mg/ml) | pH |
|---|---|---|---|---|---|---|---|---|---|
| NF-CARB07001-2.0 | CTM07048 | 2 | 10 | 3.5 | 10 | 10 | 70 | 5 | 4.5 |
| NF-CARB07001-4.0 | CTM07050 | 4 | 10 | 3.5 | 10 | 10 | 70 | 5 | 4.5 |

Abbreviations:
EDTA = Edetate disodium,
Me-β-CD = Random methyl-β-cyclodextrin,
CB = chlorobutanol,
NaCl = Sodium Chloride The data from this study indicated that all samples remained clear and colorless at the three month time point. In addition, formulation pH and osmolality values remained stable at t 3 months as compared to t=0, across all storage conditions. These data are summarized in Tables 46 and 47, respectively.

TABLE 46

Formulation pH Determination Under Long Term Storage Conditions

| Sample | Temp | t = 0 | t = 1 month | t = 2 month | t = 3 month |
|---|---|---|---|---|---|
| NF-CARB07001-2.0 | 5 | 4.50 | 4.50 | 4.61 | 4.46 |
|  | 25 | 4.50 | 4.49 | 4.57 | 4.44 |
|  | 40 | 4.50 | 4.47 | 4.49 | 4.35 |
| NF-CARB07001-4.0 | 5 | 4.60 | 4.57 | 4.64 | 4.52 |
|  | 25 | 4.60 | 4.57 | 4.63 | 4.51 |
|  | 40 | 4.60 | 4.55 | 4.56 | 4.43 |

TABLE 47

Formulation Osmolality Determination Under Long Term Storage Conditions

| Sample | Temp | t = 0 | t = 1 month | t = 2 month | t = 3 month |
|---|---|---|---|---|---|
| NF-CARB07001-2.0 | 5 | 212 | 218 | 216 | 211 |
|  | 25 | 212 | 219 | 216 | 214 |
|  | 40 | 212 | 219 | 218 | 215 |
| NF-CARB07001-4.0 | 5 | 223 | 225 | 221 | 219 |
|  | 25 | 223 | 223 | 222 | 219 |
|  | 40 | 223 | 224 | 222 | 221 |

Summaries of HPLC testing for content and purity of both samples in this study up to the two month time point for all storage conditions can be found in Tables 48, 49 and 50, under storage at 5, 25 and 40° C., respectively.

TABLE 48

Summary of HPLC Results for Samples Under 5° C. Storage Conditions

| HPLC Data Field | Sample | Time Points (Months) 0 | 1 | 2 |
|---|---|---|---|---|
| Average Total % Impurities | NF-CARB07001-2.0 | 1.2 | 1.1 | 1.1 |
|  | NF-CARB07001-4.0 | 1.3 | 1.2 | 1.1 |

TABLE 48-continued

Summary of HPLC Results for Samples Under 5° C. Storage Conditions

| HPLC Data Field | Sample | Time Points (Months) 0 | 1 | 2 |
|---|---|---|---|---|
| Average Carbetocin content by % Label Claim | NF-CARB07001-2.0 | 101.2 | 101.5 | 100.6 |
|  | NF-CARB07001-4.0 | 99.7 | 99.5 | 99.3 |
| Average Chlorobutanol content | NF-CARB07001-2.0 | 97.6 | 98.9 | 96.9 |
|  | NF-CARB07001-4.0 | 96.9 | 96.1 | 95.6 |

TABLE 49

Summary of HPLC Results for Samples Under 25° C. Storage Conditions

| HPLC Data Field | Sample | Time Points (Months) 0 | 1 | 2 |
|---|---|---|---|---|
| Average Total % Impurities | NF-CARB07001-2.0 | 1.2 | 1.3 | 1.3 |
|  | NF-CARB07001-4.0 | 1.3 | 1.3 | 1.3 |
| Average Carbetocin content by % Label Claim | NF-CARB07001-2.0 | 101.2 | 101.0 | 101.1 |
|  | NF-CARB07001-4.0 | 99.7 | 99.1 | 99.7 |
| Average Chlorobutanol content | NF-CARB07001-2.0 | 97.6 | 98.3 | 97.3 |
|  | NF-CARB07001-4.0 | 96.9 | 96.3 | 96.3 |

TABLE 50

Summary of HPLC Results for samples Under 40° C. Storage Conditions

| HPLC Data Field | Sample | Time Points (Months) | | |
|---|---|---|---|---|
| | | 0 | 1 | 2 |
| Average Total % Impurities | NF-CARB07001-2.0 | 1.2 | 1.8 | 2.3 |
| | NF-CARB07001-4.0 | 1.3 | 1.7 | 2.2 |
| Average Carbetocin content by % Label Claim | NF-CARB07001-2.0 | 101.2 | 100.5 | 99.9 |
| | NF-CARB07001-4.0 | 99.7 | 99.0 | 98.6 |
| Average Chlorobutanol content | NF-CARB07001-2.0 | 97.6 | 97.6 | 97.1 |
| | NF-CARB07001-4.0 | 96.9 | 95.7 | 95.5 |

The increase in total impurities for samples stored at 25° C. for two months was <0.1% and at 40° C. was ~1% indicating excellent chemical stability of the formulation at both strengths. Peptide content (by percent label claim) reduced by <1.5% even in samples stored at 40° C. over two months, adding further support to the unexpected observation in stability studies shown for formulations evaluated in clinical study #2 that the physical stability is not greatly effected by storage temperature, at least at early time points.

Example 10

Nine Month Stability Study for Formulations Evaluated in the First Clinical Study In this Example, the formulations presented in Table 22 were evaluated for stability at 5, 25 and 40° C.; the data presented is in respect of the nine month stability time point. The acceptance criteria for this study is provided in Table 51. Briefly, fifty-one bottles of each formulation were used for initial (release) testing and this stability study. For each formulation, 5 bottles were used for initial (release) testing, 24 bottles were stored upright (which includes 4 extra bottles) at 5° C./ambient humidity which is long-term storage condition, 14 bottles were stored upright (which includes 4 extra bottles) at 25° C./60% RH which is an accelerated stability storage condition, and 8 bottles were stored upright (which includes 2 extra bottles) at 40° C./75% RH, which is also an accelerated stability storage condition.

TABLE 51

Test Method and Acceptance Criteria for Stability Evaluation of First Clinical Formulations

| Test | Method | Acceptance Criteria for Active Batches | Acceptance Criteria for Placebo Batch |
|---|---|---|---|
| Appearance | Visual | A clear to slightly turbid, colorless solution | A clear to slightly turbid, colorless solution |
| pH | USP <791> OP 403 | pH 3.5-4.5 | pH 3.5-4.5 |
| Osmolality | SOP 437 or SOP 4000 | 140-240 mOsm/kg $H_2O$ | 140-240 mOsm/kg $H_2O$ |
| Carbetocin Identity by HPLC | TM-0027 | The retention time of the designated active peak corresponds to that of the reference standard | ≤10 μg/mL with the same retention time as carbetocin standard |
| Carbetocin Purity by HPLC | TM-0027 | Report result to the tenth decimal place | Not tested |
| Carbetocin Individual Impurities by HPLC | TM-0027 | Report result to the tenth decimal place | Not tested |
| Carbetocin Content by HPLC | TM-0027 | 80.0 to 120.0% of label claim for carbetocin | Not tested |
| Chlorobutanol Content by HPLC | TM-0027 | 80.0 to 120.0% of label claim for chlorobutanol | 80.0 to 120.0% of label claim for chlorobutanol |
| Microbial Limits | USP, 61> | Total aerobic count: ≤100 cfu/mL Total combined mold and yeast count: ≤50 cfu/mL Absence of: *Staphylococcus aureus* *Pseudomonas aeruginosa* *Escherichia coli* *Salmonella* | Total aerobic count: ≤100 cfu/mL Total combined mold and yeast count:≤50 cfu/mL Absence of: *Staphylococcus aureus* *Pseudomonas aeruginosa* *Escherichia coli* *Salmonella* |

The nine month HPLC stability data for samples evaluated in our first clinical study (see Example 6, Table 23 for 6 month time points) are presented in Table 52.

TABLE 52

Summary of Nine Month Stability Samples for First Clinical Study

| Formulation # | Batch # | Nominal Carbetocin (mg/ml) | Storage Condition | Storage Period (Months) | Peptide Recovery (%) | Total Unknown Impurities (%) | Chlorobutanol Recovery (%) |
|---|---|---|---|---|---|---|---|
| CARB-011-3-1.5 | CTM06076 | 1.5 | Initial | — | 102.3 | 1.3 | 99.7 |
|  |  |  | 5° C. | 9 | 99.8 | 1.4 | 99.2 |
| CARB-011-3-3.0 | CTM06078 | 3.0 | Initial | — | 103.2 | 1.3 | 99.8 |
|  |  |  | 5° C. | 9 | 100.8 | 1.4 | 97.3 |
| CARB-011-3-5.0 | CTM06080 | 5.0 | Initial | — | 102.5 | 1.4 | 98.8 |
|  |  |  | 5° C. | 9 | 100.3 | 1.3 | 96.1 |
| Current Specifications: |  |  |  |  | 80.0-120.0 | ≤3.5 | 80.0-120.0 |

Briefly, the data presented in Table 52 show less than 0.1% increase in total impurities from t=0 values was observed when formulations were stored at 5° C. for nine months. This data agree well with the predicted values for the same formulation shown at 6 months of storage. However, peptide content was remarkably improved. As shown in this Example, peptide content, at nine months of storage, was only 3% less than at t=0, suggesting that chemical stability over long-term storage at 5° C. is even better than the early time points (e.g., 6 months).

Example 11

Two Month Stability Time Points for Formulations Evaluated in the Second Clinical Study In this Example, the two month stability data respecting the clinical formulations (second clinical study) as shown in Table 38, at the four concentrations presented in Table 39, are shown in below Table 53.

TABLE 53

Sample Groups for Nine Month Stability Time Points From Clinical Study 2

| # | Formulation Description | Formulation Number | Lot Number | Batch Size |
|---|---|---|---|---|
| 1 | 1.5 mg/mL Carbetocin | NF-CARB07001-1.5 | CTM07056 | 92 bottles |
| 2 | 2.5 mg/mL Carbetocin | NF-CARB07001-2.5 | CTM07058 | 92 bottles |
| 3 | 4.0 mg/mL Carbetocin | NF-CARB07001-4.0 | CTM07061 | 92 bottles |
| 4 | 8.0 mg/mL Carbetocin | NF-CARB07001-8.0 | CTM07053 | 66 bottles |
| 5 | Placebo | NF-CARB07001-PL | CTM07062 | 75 bottles |

Formulations were prepared as previously described. Bottles were filled with 2.0 ml of Carbetocin Nasal Spray—Formulation Nos. 1, 2, 3, 4, and 5—into at least fifty-five 3-cc non-silanized screw cap type 1 clear glass bottles per formulation for stability purposes. Cap the bottles with trifoil lined polypropylene caps. A summary of the physical and chemical stability results is shown in Table 54.

TABLE 54

Physical and Chemical Testing of Clinical Study 2 Samples at t = 2 Month

| Sample | Temp | Time Point | pH | Osmolality (mOsm/KgH$_2$0) | Carbetocin Content (% label claim) | % CB Content | % Total Impurities |
|---|---|---|---|---|---|---|---|
| Nf-carb07001-8.0 | Initial | Initial | 4.5 | 233 | 100.3 | 95.4 | 1.4 |
| Nf-carb07001-1.5 |  |  | 4.5 | 214 | 105.1 | 99.6 | 1.2 |
| Nf-carb07001-2.5 |  |  | 4.6 | 217 | 100.8 | 98.5 | 1.3 |
| Nf-carb07001-4.0 |  |  | 4.5 | 221 | 100.5 | 96.6 | 1.3 |
| Nf-carb07001-1.5 | 25° C. | 2 week | 4.5 | 214 | 106.3 | 98.8 | 1.4 |
| Nf-carb07001-2.5 |  |  | 4.5 | 217 | 101.0 | 98.2 | 1.5 |
| Nf-carb07001-1.5 | 25° C. | 3 week | 4.5 | 218 | 105.0 | 99.1 | 1.1 |
| Nf-carb07001-2.5 |  |  | 4.5 | 222 | 100.7 | 98.1 | 1.1 |
| Nf-carb07001-8.0 | 5° C. | 1 month | 4.5 | 229 | 100.1 | 93.1 | 1.2 |
| Nf-carb07001-1.5 |  |  | 4.5 | 215 | 104.2 | 98.7 | 1.2 |
| Nf-carb07001-2.5 |  |  | 4.6 | 216 | 100.0 | 97.3 | 1.2 |
| Nf-carb07001-4.0 |  |  | 4.5 | 220 | 100.6 | 95.3 | 1.2 |
| Nf-carb07001-8.0 | 25° C. |  | 4.5 | 234 | 99.8 | 96.6 | 1.3 |
| Nf-carb07001-1.5 |  |  | 4.5 | 220 | 104.3 | 98.9 | 1.3 |
| Nf-carb07001-2.5 |  |  | 4.5 | 222 | 99.7 | 97.0 | 1.3 |
| Nf-carb07001-4.0 |  |  | 4.5 | 220 | 100.0 | 95.1 | 1.3 |
| Nf-carb07001-8.0 | 40° C. |  | 4.4 | 235 | 99.4 | 92.9 | 1.9 |
| Nf-carb07001-1.5 |  |  | 4.4 | 216 | 103.6 | 98.6 | 1.8 |
| Nf-carb07001-2.5 |  |  | 4.5 | 216 | 99.0 | 96.3 | 1.7 |
| Nf-carb07001-4.0 |  |  | 4.4 | 218 | 99.3 | 95.0 | 1.3 |
| Nf-carb07001-8.0 | 25° C. | 2-month | 4.4 | 231 | 100.7 | 95.1 | 1.3 |
| Nf-carb07001-1.5 |  |  | 4.5 | 216 | 104.1 | 97.7 | 1.3 |
| Nf-carb07001-2.5 |  |  | 4.5 | 219 | 100.2 | 97.3 | 1.3 |
| Nf-carb07001-4.0 |  |  | 4.5 | 223 | 100.1 | 95.3 | 1.3 |

TABLE 54-continued

Physical and Chemical Testing of Clinical Study 2 Samples at t = 2 Month

| Sample | Temp | Time Point | pH | Osmolality (mOsm/KgH$_2$0) | Carbetocin Content (% label claim) | % CB Content | % Total Impurities |
|---|---|---|---|---|---|---|---|
| Nf-carb07001-8.0 | 40° C. | | 4.4 | 239 | 98.9 | 93.3 | 2.4 |
| Nf-carb07001-1.5 | | | 4.4 | 219 | 103.3 | 97.8 | 2.4 |
| Nf-carb07001-2.5 | | | 4.5 | 229 | 99.2 | 96.3 | 2.3 |
| Nf-carb07001-4.0 | | | 4.4 | 228 | 99.1 | 94.8 | 2.4 |

These data show that loss of peptide content (by % label claim) did not exceed 1% for samples stored at 25° C. for two months when compared to their t=0 values. Total impurities increased by <0.1% for all samples, confirming the stability data obtained previously obtained for the same formulation, suggesting that stability may be better than anticipated.

Example 12

Thermal Stress Induced Carbetocin Degradation Products Identified by LC-Ms Analysis In this Example, formulations for intranasal delivery of carbetocin were analyzed by LC-MS analysis for the presence of thermal stressed induced degradation products produced under accelerated conditions (e.g., 40-50° C.). This information can be used to predict the commercial shelf-life of Carbetocin Nasal Spray Formulation and understand the degradation products and pathways that occur under normal conditions (e.g., 5-25° C.).

Accordingly, this Example provides a list of carbetocin degradants identified by molecular weight and corresponding HPLC relative retention time (RRT) that will be used in classifying carbetocin HPLC sample impurities. Specifically, this information will aid in identifying degradation products present in stability testing of Carbetocin Nasal Spray Formulations evaluated in clinical and pre-clinical studies. The formulations analyzed are provided in Tables 55, 56 and 57.

TABLE 55

CARB-006 Samples Analyzed

| CARB-006 # | Carbetocin (mg/ml) | Me-β-CD (mg/ml) | EDTA (mg/ml) | DDPC (mg/ml) | Arginine (mM) | Sorbitol (mM) | NaCl (mM) | CB (mg/ml) | pH | Storage Temp/Duration |
|---|---|---|---|---|---|---|---|---|---|---|
| 1 | 10 | 40 | 5.0 | 0 | 10 | 0 | 40 | 5 | 4.5 | 40'C./6 M |
| 2 | 10 | 0 | 2.5 | 0 | 0 | 131 | 0 | 5 | 4.0 | 40'C./6 M |
| 3 | 10 | 30 | 2.0 | 1.0 | 10 | 0 | 70 | 0 | 4.0 | 40'C./6 M |

TABLE 56

CARB-013 Samples Analyzed

| CARB-013 | Formulation pH | Buffer | Buffer pK$_a$ | Storage Temp./Duration |
|---|---|---|---|---|
| 2* | 3.0 | tartrate | 2.96 (pK$_1$) | 25' C./3M |
| 3* | 3.5 | citrate | 3.12 (pK$_1$) | 25' C./3M |
| 4* | 3.5 | tartrate | 2.96 (pK$_1$) | 25' C./3M |
| 5* | 4.0 | acetate | 4.74 | 40' C./3M |
| 6* | 4.0 | citrate | 4.76 (pK$_2$) | 40' C./3M |
| 13* | 7.0 | citrate | 6.40 (pK$_3$) | 40' C./3M |
| 14* | 7.0 | phosphate | 7.10 (pK$_2$) | 40' C./3M |
| 15* | 8.0 | phosphate | 7.10 (pK$_2$) | 25' C./3M |

TABLE 57

CARB-052 Samples Analyzed

| Reagent | Grade | Vendor | Cat # | Lot # |
|---|---|---|---|---|
| Carbetocin | Research | ppl | 41004 | 105005-01 |
| Sodium chloride | usp | Spectrum | SO155 | QJ1142, UC0016 |
| Glacial acetic acid | USP | Spectrum | AC110 | RF0177, TA0912 |
| Sodium Acetate, anhydrous | usp | Spectrum | SO104 | UB1152 |

HPLC analysis was performed per using a Cl 8 reverse phase column on a HPLC instrument. MS analysis parameters: pos., scan mode 100-1100 amu range, 1.2 sec/scan. 12 carbetocin degradants were identified and categorized into four degradation classes: oxidation, deamidation, hydrolysis, and API isomer. Additionally, two unclassified degradation products were observed.

Deamidation products at 1.16 and 1.23 RRT had a +1 amu difference (Δ amu) from native carbetocin and occurred in greatest abundance. The proposed possible sites of carbetocin deamidation include asparagine, glutamine residues and C-terminal amine. Detectable levels of other degradants were observed at RRT 0.22, 0.24-0.25 (hydrolysis product, +18 Δ amu, FIG. 2), 0.57-0.59, 0.73-0.74 (oxidation product, +16 Δamu), 0.92, 0.95-0.96, 1.08-1.09 (API isomer, 0 Δ amu), 0.78, 1.18, 1.26 (deamidation product, +1 Δ amu), and 0.29, 0.53 (unclassified product, +19 Δ amu). Table VII summarizes RRT and Δ amu results discussed in this section. The observed degradation products are summarized in Table 59.

TABLE 59

Summary of Carbetocin Formulation Related Degradation Products

| | Deamidation | oxidation | Hydrolysis | API Isomers | Unclassified |
|---|---|---|---|---|---|
| RRT | 0.78, 1.16, 1.18, 1.23, 1.26 | 0.57-0.59, 0.73-0.74 | 0.2, 0.24-0.25 | 0.92, 0.95-0.96, 1.08-1.09 | 0.29, 0.53 |
| Mass Diff. (Δ am μ) | +1 | +16 | +18 | 0 | +19 |

The effects of thermal stress were examined in concert with various pH and buffer conditions in CARB-052. Comparing citrate vs. acetate containing samples, neither buffer resulted in occurrence of different degradation products. However, incubation at 50° C., t=1M (CARB-052-3 and 4) vs. 40° C., t=1M (CARB-052-1 and 2) resulted in unclassified 0.29 RRT degradant and elevated levels of deamidation products. Oxidation as well as additional deamidation and hydrolysis products were present in 40° C., t=11M samples (CARB-052-5 and 6) that were not found in 40° C. and 50° C., t=1M samples. Furthermore, at t=1, 2, and 3M stability time points in CARB-033, Phase I clinical study Carbetocin Nasal Spray Formulations CARB-011-3-XX and NF-CARB07001-XX were shown to have predominant levels of 1.18 RRT carbetocin deamidation product present in all samples.

Although the foregoing disclosure has been described in detail by way of example for purposes of clarity of understanding, it will be apparent to the artisan that certain changes and modifications may be practiced within the scope of the appended claims which are presented by way of illustration not limitation. All U.S. patents, U.S. patent application publications, U.S. patent applications, foreign patents, foreign patent applications, non-patent publications, figures, tables, and websites referred to in this specification are expressly incorporated herein by reference, in their entirety.

It is noted, however, that the various publications discussed herein are incorporated solely for their disclosure prior to the filing date of the present application, and the inventors reserve the right to antedate such disclosure by virtue of prior disclosure.

We claim:

1. A pharmaceutical formulation for intranasal delivery of carbetocin, comprising:
   a) carbetocin in a concentration of from about 1.5 mg/ml to about 10 mg/ml;
   b) methyl-β-cyclodextrin in a concentration of from about 10 mg/ml to about 40 mg/ml;
   c) EDTA in a concentration of from about 2 mg/ml to about 5 mg/ml;
   d) sodium chloride in a concentration of from about 40 mM to about 70 mM;
   e) arginine, or a salt thereof, in a concentration of about 10 mM;
   f) acetate in a concentration of about 10 mM; and
   g) chlorobutanol in a concentration of from about 2.5 mg/ml to about 5 mg/ml, wherein the formulation has a pH from about 4 to about 6.

2. The pharmaceutical formulation of claim 1, which has an osmolality from about 200 to about 250 mOsm/kgH$_2$O.

3. The pharmaceutical formulation of claim 1, further comprising one or more adjunctive therapeutic agents.

4. The pharmaceutical formulation of claim 3, wherein the adjunctive therapeutic agent is selected from a serotonin reuptake inhibitor, a selective serotonin reuptake inhibitor, an antipsychotic medication, an anti-convulsant, a stimulant medication, an anti-viral medication, an axiolytic medication, a vitamin, an immunotherapeutic agent, and a combination thereof.

5. A method for treating autism, in a mammalian subject in need thereof, comprising:
   administering a therapeutically effective amount of the pharmaceutical formulation of claim 1 to the subject.

6. A method for treating autism, in a mammalian subject in need thereof, comprising:
   co-administering a therapeutically effective amount of the pharmaceutical formulation of claim 1 and one or more adjunctive therapeutic agents to the subject.

7. The method of claim 6, wherein the adjunctive therapeutic agent is selected from a group consisting of a serotonin reuptake inhibitor, a selective serotonin reuptake inhibitor, an antipsychotic medication, an anti-convulsant, a stimulant medication, an anti-viral medication, an axiolytic medication, a vitamin, an immunotherapeutic agent, and a combination thereof.

8. The method of claim 5, further comprising a treatment of a therapy of behavioral modification or diet modification.

9. The method of claim 6, further comprising a treatment of a therapy of behavioral modification or diet modification.

10. The pharmaceutical formulation of claim 1, wherein the pH is about 4.5±0.3.

11. The pharmaceutical formulation of claim 1, wherein the carbetocin is present in a concentration of from about 1.5 mg/ml to about 8.0 mg/ml.

12. The pharmaceutical formulation of claim 1, wherein the carbetocin is present in a concentration of from about 1.5 mg/ml to about 5.0 mg/ml.

13. The pharmaceutical formulation of claim 1, wherein the carbetocin is present in a concentration of about 4 mg/ml.

14. The pharmaceutical formulation of claim 1, wherein the carbetocin is present in a concentration of about 10 mg/ml.

15. The pharmaceutical formulation of claim 1, wherein the methyl-β-cyclodextrin is present in a concentration of from about 10 mg/ml to about 20 mg/ml.

16. The pharmaceutical formulation of claim 1, wherein the methyl-β-cyclodextrin is present in a concentration of about 10 mg/ml.

17. The pharmaceutical formulation of claim 1, wherein the EDTA is present in a concentration of from about 2.5 mg/ml to about 3.5 mg/ml.

18. The pharmaceutical formulation of claim 1, wherein the EDTA is present in a concentration of about 3.5 mg/ml.

19. The pharmaceutical formulation of claim 1, wherein the sodium chloride is present in a concentration of about 52 mM.

20. The pharmaceutical formulation of claim 1, wherein the sodium chloride is present in a concentration of about 70 mM.

21. The pharmaceutical formulation of claim 1, wherein the chlorobutanol is present in a concentration of about 5 mg/ml.

22. A pharmaceutical formulation for intranasal delivery of carbetocin, comprising:
   a) carbetocin in a concentration of from about 1.5 mg/ml to about 10 mg/ml;
   b) methyl-β-cyclodextrin in a concentration of from about 10 mg/ml to about 40 mg/ml;
   c) EDTA in a concentration of from about 2 mg/ml to about 5 mg/ml;
   d) sodium chloride in a concentration of from about 40 mM to about 70 mM;
   e) arginine, or a salt thereof;
   f) acetate; and
   g) chlorobutanol in a concentration of from about 2.5 mg/ml to about 5 mg/ml, wherein the formulation has a pH from about 4 to about 6.

23. A pharmaceutical formulation for intranasal delivery of carbetocin, comprising:
   a) carbetocin in a concentration of from about 1.5 mg/ml to about 10 mg/ml;
   b) methyl-β-cyclodextrin in a concentration of about 7.4 to about 7.5 mM;
   c) EDTA in a concentration of about 9.4 mM;

d) sodium chloride in a concentration of from about 52 mM to about 70 mM;
e) arginine, or a salt thereof, in a concentration of about 10 mM;
f) acetate in a concentration of about 10 mM; and
g) chlorobutanol in a concentration of about 28.2 mM,
wherein the formulation has a pH from about 4 to about 6 and an osmolality from about 200 to about 250 mOsm/kgH$_2$O.

* * * * *